US008163499B2

(12) United States Patent
Singh et al.

(10) Patent No.: US 8,163,499 B2
(45) Date of Patent: Apr. 24, 2012

(54) DRUG SELECTION FOR BREAST CANCER THERAPY USING ANTIBODY-BASED ARRAYS

(75) Inventors: Sharat Singh, Rancho Santa Fe, CA (US); Jeanne Harvey, Livermore, CA (US); Phillip Kim, Irvine, CA (US); Xinjun Liu, San Diego, CA (US); Limin Liu, San Diego, CA (US); Robert Barham, San Marcos, CA (US); Bruce Neri, Carlsbad, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 290 days.

(21) Appl. No.: 12/511,017

(22) Filed: Jul. 28, 2009

(65) Prior Publication Data

US 2010/0167945 A1  Jul. 1, 2010

Related U.S. Application Data

(63) Continuation of application No. PCT/US2009/035013, filed on Feb. 24, 2009.

(60) Provisional application No. 61/140,558, filed on Dec. 23, 2008, provisional application No. 60/117,908, filed on Nov. 25, 2008, provisional application No. 60/108,384, filed on Oct. 24, 2008, provisional application No. 60/106,404, filed on Oct. 17, 2008, provisional application No. 61/031,319, filed on Feb. 25, 2008.

(51) Int. Cl.
*G01N 33/53* (2006.01)
*G01N 33/58* (2006.01)
*G01N 33/68* (2006.01)
*G01N 33/545* (2006.01)
*G01N 33/574* (2006.01)

(52) U.S. Cl. ........ 435/7.1; 435/7.21; 435/7.23; 435/7.8; 435/25; 436/64; 436/501

(58) Field of Classification Search .................. None
See application file for complete search history.

(56) References Cited

U.S. PATENT DOCUMENTS

| 4,233,402 | A | 11/1980 | Maggio et al. |
| 5,089,419 | A | 2/1992 | Kuniyuki |
| 5,120,660 | A | 6/1992 | Kuniyuki |
| 5,445,944 | A | 8/1995 | Ullman |
| 5,516,931 | A * | 5/1996 | Giese et al. .................. 560/59 |
| 5,527,684 | A | 6/1996 | Mabile et al. |
| 5,876,944 | A | 3/1999 | Kuo |
| 6,201,109 | B1 | 3/2001 | Avnur et al. |
| 6,627,400 | B1 | 9/2003 | Singh et al. |
| 6,659,351 | B1 | 12/2003 | Bailleu et al. |
| 6,770,439 | B2 | 8/2004 | Singh et al. |
| 6,818,399 | B2 | 11/2004 | Singh et al. |
| 6,949,347 | B2 | 9/2005 | Singh et al. |
| 6,972,198 | B2 | 12/2005 | Craig et al. |
| 7,101,682 | B2 | 9/2006 | Ullman et al. |
| 7,279,286 | B2 | 10/2007 | Kannt et al. |
| 7,402,399 | B2 | 7/2008 | Mukherjeei et al. |
| 7,537,938 | B2 * | 5/2009 | Kirakossian et al. ......... 436/526 |
| 7,695,924 | B2 | 4/2010 | Perez et al. |
| 7,695,926 | B2 | 4/2010 | Perez et al. |
| 2002/0142361 | A1 | 10/2002 | Emmert-Buck |
| 2002/0168641 | A1 | 11/2002 | Mortensen et al. |
| 2003/0059811 | A1 | 3/2003 | Djaballah et al. |
| 2003/0087311 | A1 | 5/2003 | Wolf |
| 2003/0153013 | A1 | 8/2003 | Huang |
| 2003/0153014 | A1 | 8/2003 | Shen et al. |
| 2004/0077090 | A1 * | 4/2004 | Short ........................... 435/471 |
| 2004/0106161 | A1 | 6/2004 | Bossenmaier et al. |
| 2004/0157271 | A1 | 8/2004 | Kirakossian et al. |
| 2004/0175696 | A1 | 9/2004 | Ullman et al. |
| 2006/0024723 | A1 | 2/2006 | Hussa et al. |
| 2006/0024846 | A1 | 2/2006 | Singh et al. |
| 2006/0127945 | A1 | 6/2006 | Preaudat et al. |
| 2008/0187948 | A1 | 8/2008 | Chan-Hui et al. |
| 2008/0261829 | A1 | 10/2008 | Harvey et al. |
| 2009/0035792 | A1 | 2/2009 | Singh et al. |
| 2009/0124511 | A1 | 5/2009 | Archer et al. |
| 2010/0021457 | A1 | 1/2010 | Pfleger et al. |

FOREIGN PATENT DOCUMENTS

| EP | 0 310 132 A2 | 4/1989 |
| EP | 1 145 004 B1 | 4/2004 |
| EP | 1 673 635 B1 | 4/2009 |
| WO | WO 01/27611 A2 | 4/2001 |
| WO | WO 02/090964 A | 11/2002 |
| WO | WO 03/087761 A2 | 10/2003 |
| WO | WO2006/044748 * | 4/2006 |
| WO | WO 2006/054991 A | 5/2006 |
| WO | WO 2006/055739 A2 | 5/2006 |
| WO | WO 2006/105642 A1 | 10/2006 |
| WO | WO 2006/119980 A1 | 11/2006 |
| WO | WO 2008/019375 A3 | 2/2008 |

(Continued)

OTHER PUBLICATIONS

Sanchez-Carbayo (Clinical Chemistry, 2006, vol. 52, pp. 1651-1659).*
Lu et al (Electrophoresis, 2007, vol. 28, pp. 406-413).*
Arpino et al (Breast Cancer Research, 2003, vol. 6, pp. R149-R156).*
Mouridsen et al (Journal of Clinical Oncology, 2003, vol. 21, pp. 2101-2109).*
Pearce et al (Journal of Biological chemistry, 2003, vol. 278, pp. 7630-7638).*
Blume-Jensen, Peter et al. "Oncogenic kinase signalling," Nature, 2001, vol. 411, pp. 355-365.
Gembitsky, Dmitry "A Prototype Antibody Microarray Platform to Monitor Changes in Protein Tyrosine Phosphorylation," Molecular & Cellular Proteomics 3.11, 2004, pp. 1102-1118.

(Continued)

*Primary Examiner* — Karen Canella
(74) *Attorney, Agent, or Firm* — Kilpatrick Townsend & Stockton LLP

(57) ABSTRACT

The present invention provides compositions and methods for detecting the activation states of components of signal transduction pathways in tumor cells. Information on the activation states of components of signal transduction pathways derived from use of the invention can be used for cancer diagnosis, prognosis, and in the design of cancer treatments.

88 Claims, 23 Drawing Sheets

FOREIGN PATENT DOCUMENTS

| WO | WO2008/036802 | * | 3/2008 |
|---|---|---|---|
| WO | WO 2008/036802 A | | 3/2008 |
| WO | WO 2009/012140 A2 | | 1/2009 |

OTHER PUBLICATIONS

Hudelist, Gernot et al. "Use of high-throughput protein array for profiling of differentially expressed proteins in normal and malignant breast tissue," Breast Cancer Research and Treatment, 2004, vol. 86: 281-291.

Kopf, Eliezer et al. "Antibody arrays—An emerging tool in cancer proteomics," The International Journal of Biochemistry & Cell Biology 39 (2007) pp. 1305-1317.

Nielsen, Ulrik B. et al. "Profiling receptor tyrosine kinase activation by using Ab microarrays," PNAS, 2003, vol. 100, No. 16, pp. 9330-9335.

Nielsen, Ulrik et al. "Multiplexed sandwich assays in microarray format," Journal of Immunological Methods, 2004, vol. 290, pp. 107-120.

Angenendt et al. "3D Protein Microarrays: Performing Multiplex Immunoassays on a Single Chip," Anal. Chem., 2003, vol. 75, pp. 4368-4372.

Bartling et al., "Comparative application of antibody and gene array for expression profiling in human squamous cell lung carcinoma," Lung Cancer, 2005, vol. 49, No. 2, pp. 145-154.

Dorland's Medical Dictionary for Healthcare Consumers (non-small cell carcinoma, Merch Sharp & Dohme Corp.) 2007, 1 page.

Haab, Brian "Antibody Arrays in Cancer Research," Molecular & Cellular Proteomics, 2005, vol. 4, No. 4, pp. 377-383.

Haab, Brian "Applications of Antibody array platforms," Current Opinion in Biotechnology, 2006, vol. 17, pp. 415-421.

Langry et al., U.S. Dept. of Energy Report No. UCRL-ID-136797, Nov. 5, 1999, 30 pages.

* cited by examiner

A431: HER-1 & HER-2-Positive; MD-MBA 468: Only HER-1-Positive

RTK Pathway Chip

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|----|----|----|----|----|----|----|----|----|----|----|
| A | | ER (det w/ Ser118) | | | ER (SER 167) | | | AIB1 | | | N-CoR | | | PR | | | IGF1R | | | |
| B | | | | | | | | | | | | | | | | | | | | |
| C | | | | | | | | | | | | | | | | | | | | |
| D | | | | | | | | | | | | | | | | | | | | |
| E | | cMET | | | ErbB1 | | | ErbB2 | | | P95ErbB2 | | | ErbB3 | | | ErbB4 | | | |
| F | | | | | | | | | | | | | | | | | | | | |
| G | | | | | | | | | | | | | | | | | | | | |
| H | | | | | | | | | | | | | | | | | | | | |
| I | | Shc | | | PI3K | | | Erk | | | Rsk | | | Akt | | | P70S6K | | | |
| J | | | | | | | | | | | | | | | | | | | | |
| K | | | | | | | | | | | | | | | | | | | | |
| L | | | | | | | | | | | | | | | | | | | | |
| M | | Ki67 | | | TOPO II | | | | | | | | | | | | | | | |
| N | | | | | | | | | | | | | | | | | | | | |
| O | | | | | | | | | | | | | | | | | | | | |
| P | | | | | | | | | | | | | | | | | | | | |
| Q | | | | | | | | | | | CK Cont | | | Assay Cont | | | Printing Cont | | | |
| R | | | | | | | | | | | | | | | | | | | | |
| S | | | | | | | | | | | | | | | | | | | | |
| T | | | | | | | | | | | | | | | | | | | | |

*FIG. 5*

Angiogenesis Chip

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|----|----|----|----|----|----|----|----|----|----|----|
| A | | | | | | | | | | | | | | | | | | | | |
| B | | | | | | | | | | | | | | | | | | | | |
| C | | | | | | | | | | | | | | | | | | | | |
| D | | | | | | | | | | | | | | | | | | | | |
| E | | | | | | | | | | | | | | | | | | | | |
| F | | | | | | | | | | | | | | | | | | | | |
| G | | | | | | | | | | | | | | | | | | | | |
| H | | | | | | | | | | | | | | | | | | | | |
| I | | | Shc | | | PI3K | | | Erk | | | Rsk | | | Akt | | | P70S6K | | |
| J | | | | | | | | | | | | | | | | | | | | |
| K | | | | | | | | | | | | | | | | | | | | |
| L | | | | | | | | | | | | | | | | | | | | |
| M | | | Ki67 | | | TOPO II | | | VEGFR1 | | | VEGFR2 | | | Tie2 | | | V-Cadherin-R2 | | |
| N | | | | | | | | | | | | | | | | | | | | |
| O | | | | | | | | | | | | | | | | | | | | |
| P | | | | | | | | | | | | | | | | | | | | |
| Q | | | PDGFRa | | | PDGFRb | | | | | | CK Cont | | | Assay Cont | | | Printing Cont | | |
| R | | | | | | | | | | | | | | | | | | | | |
| S | | | | | | | | | | | | | | | | | | | | |
| T | | | | | | | | | | | | | | | | | | | | |

*FIG. 6*

Combined Chip

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| A | | ER | | | ER (SER 167) | | | AIB1 | | | N-CoR | | | PR | | | IGF1R | | | |
| B | | (det w/ Ser118) | | | | | | | | | | | | | | | | | | |
| C | | | | | | | | | | | | | | | | | | | | |
| D | | | | | | | | | | | | | | | | | | | | |
| E | | cMET | | | ErbB1 | | | ErbB2 | | | P95ErbB2 | | | ErbB3 | | | ErbB4 | | | |
| F | | | | | | | | | | | | | | | | | | | | |
| G | | | | | | | | | | | | | | | | | | | | |
| H | | | | | | | | | | | | | | | | | | | | |
| I | | Shc | | | PI3K | | | Erk | | | Rsk | | | Akt | | | P70S6K | | | |
| J | | | | | | | | | | | | | | | | | | | | |
| K | | | | | | | | | | | | | | | | | | | | |
| L | | | | | | | | | | | | | | | | | | | | |
| M | | Ki67 | | | TOPO II | | | VEGFR1 | | | VEGFR2 | | | Tie2 | | | V-Cadherin-R2 | | | |
| N | | | | | | | | | | | | | | | | | | | | |
| O | | | | | | | | | | | | | | | | | | | | |
| P | | | | | | | | | | | | | | | | | | | | |
| Q | | PDGFRa | | | PDGFRb | | | | | | CK Cont | | | Assay Cont | | | Printing Cont | | | |
| R | | | | | | | | | | | | | | | | | | | | |
| S | | | | | | | | | | | | | | | | | | | | |
| T | | | | | | | | | | | | | | | | | | | | |

*FIG. 8*

|   | 1 | 2 3 4 | 5 6 7 | 8 9 10 | 11 12 13 | 14 15 16 | 17 18 19 | 20 |
|---|---|---|---|---|---|---|---|---|
| A |   | ER | ER (SER 118) | ER (SER 167) | ER-AIB1 | ER-N-CoR | EGFR |   |
| B |   |   |   |   |   |   |   |   |
| C |   |   |   |   |   |   |   |   |
| D |   |   |   |   |   |   |   |   |
| E |   | PR | IGF1R | Shc | PI3K | Erk | ErbB2 |   |
| F |   |   |   |   |   |   |   |   |
| G |   |   |   |   |   |   |   |   |
| H |   |   |   |   |   |   |   |   |
| I |   | Rsk | Akt | P70S6K | Ki67 | TOPO II | P95ErbB2 |   |
| J |   |   |   |   |   |   |   |   |
| K |   |   |   |   |   |   |   |   |
| L |   |   |   |   |   |   |   |   |
| M |   | VEGFR1 | VEGFR2 | Tie2 | V-Cadherin-R2 | PDGFRa | ErbB3 |   |
| N |   |   |   |   |   |   |   |   |
| O |   |   |   |   |   |   |   |   |
| P |   |   |   |   |   |   |   |   |
| Q |   | PDGFRb | CK Cont | Assay Cont |   | Printing Cont | ErbB4 |   |
| R |   |   |   |   |   |   |   |   |
| S |   |   |   |   |   |   |   |   |
| T |   |   |   |   |   |   |   |   |

*FIG. 9*

|  | SKBR3 | T47D | BT-474 | MDA-MB-468 |
|---|---|---|---|---|
| pHER2 | — ≡ |  | ≡ ≡ | pHER1 — |
| HER2 | — ≡ | — — | ≡ ≡ | HER1 — — |
| EGF | −  + | −  + | −  + | EGF −  + |
| pHER2 | ≡ ≡ | ≡ | ≡ ≡ | pHER1 |
| HER2 | ≡ ≡ | — — | ≡ ≡ | HER1 — — |
| HRGβ | −  + | −  + | −  + | HRGβ −  + |

FIG. 21

DRUG SELECTION FOR BREAST CANCER THERAPY USING ANTIBODY-BASED ARRAYS

CROSS-REFERENCES TO RELATED APPLICATIONS

The present application is a continuation of PCT Application No. PCT/US2009/035013, filed Feb. 24, 2009, which application claims priority to U.S. Provisional Application No. 61/031,319, filed Feb. 25, 2008, U.S. Provisional Application No. 61/106,404, filed Oct. 17, 2008, U.S. Provisional Application No. 61/108,384, filed Oct. 24, 2008, U.S. Provisional Application No. 61/117,908, filed Nov. 25, 2008, and U.S. Provisional Application No. 61/140,558, filed Dec. 23, 2008, the disclosures of which are herein incorporated by reference in their entirety for all purposes.

BACKGROUND OF THE INVENTION

The process of signal transduction in cells is responsible for a variety of biological functions including cell division and death, metabolism, immune cell activation, neurotransmission, and sensory perception to name but a few. Accordingly, derangements in normal signal transduction in cells can lead to a number of disease states such as diabetes, heart disease, autoimmunity, and cancer.

One well characterized signal transduction pathway is the MAP kinase pathway, which is responsible for transducing the signal from epidermal growth factor (EGF) to the promotion of cell proliferation in cells (see, FIG. 1). EGF binds to a transmembrane receptor-linked tyrosine kinase, the epidermal growth factor receptor (EGFR), which is activated by the binding of EGF. The binding of EGF to EGFR activates the tyrosine kinase activity of the cytoplasmic domain of the receptor. One consequence of this kinase activation is the autophosphorylation of EGFR on tyrosine residues. The phosphorylated tyrosine residues on the activated EGFR provide a docking site for the binding of SH2 domain containing adaptor proteins such as GRB2. In its function as an adaptor, GRB2 further binds to a guanine nucleotide exchange factor, SOS, by way of an SH3 domain on GRB2. The formation of the complex of EGFR-GRB2-SOS leads to SOS activation of a guanine nucleotide exchange factor that promotes the removal of GDP from Ras. Upon removal of GDP, Ras binds GTP and becomes activated.

Following activation, Ras binds to and activates the protein kinase activity of RAF kinase, a serine/threonine-specific protein kinase. What follows is the activation of a protein kinase cascade that leads to cell proliferation. In outline, RAF kinase then phosphorylates and activates MEK, another serine/threonine kinase. Activated MEK phosphorylates and activates mitogen-activated protein kinase (MAPK). Among the targets for further phosphorylation by MAPK are 40S ribosomal protein S6 kinase (RSK). The phosphorylation of RSK by MAPK results in activation of RSK, which in turn phosphorylates ribosomal protein S6. Another known target of MAPK is the proto-oncogene, c-Myc, a gene important for cell proliferation, which is mutated in a variety of cancers. MAPK also phosphorylates and activates another protein kinase, MNK, which in turn phosphorylates the transcription factor, CREB. Indirectly, MAPK also regulates the transcription of the Fos gene, which encodes yet another transcription factor involved in cell proliferation. By altering the levels and activities of such transcription factors, MAPK transduces the original extracellular signal from EGF into altered transcription of genes that are important for cell cycle progression.

Given the central role that signal transduction pathways play in cell growth, it is not surprising that many cancers arise as a result of mutations and other alterations in signal transduction components that result in aberrant activation of cell proliferation pathways. For example, overexpression or hyperactivity of EGFR has been associated with a number of cancers, including glioblastoma multiforme, colon cancer, and lung cancer. This has prompted the development of anticancer therapeutics directed against EGFR, including gefitinib and erlotinib for lung cancer, and cetuximab for colon cancer.

Cetuximab is an example of a monoclonal antibody inhibitor, which binds to the extracellular ligand-binding domain of EGFR, thus preventing the binding of ligands which activate the EGFR tyrosine kinase. In contrast, gefitinib and erlotinib are small molecules which inhibit the intracellularly-located EGFR tyrosine kinase. In the absence of kinase activity, EGFR is unable to undergo autophosphorylation at tyrosine residues, which is a prerequisite for binding of downstream adaptor proteins, such as GRB2. By halting the signaling cascade in cells that rely on this pathway for growth, tumor proliferation and migration is diminished.

Additionally, other studies have shown that about 70% of human melanomas and a smaller fraction of other tumors have a point mutation (V599E) in the Raf gene which leads to persistent activation of the MAPK pathway (see, e.g., Davies et al., *Nature*, 417:949-954 (2002)). Such results suggest that mutations in particular signal transduction pathways may be characteristic of particular types of tumors and that such specific, altered signal transduction pathways may be a promising target for chemotherapeutic intervention.

Given that different cancer treatments, particularly cancer chemotherapy, may function either directly or indirectly by means of either blocking or activating cellular signal transduction pathways that are involved in cell proliferation or death, respectively, the activity of a given signal transduction pathway in a particular form of cancer may serve as a good indicator of the efficacy of various cancer treatments. Accordingly, in addition to fulfilling other needs, the present invention provides a method for evaluating the effectiveness of potential anticancer therapies for an individual patient. As such, the present invention provides methods for assisting a physician in selecting a suitable cancer therapy at the right dose and at the right time for every patient.

BRIEF SUMMARY OF THE INVENTION

The present invention provides compositions and methods for detecting the activation states of components of signal transduction pathways in tumor cells (e.g., circulating cells of a breast tumor). Information on the activation states of components of signal transduction pathways derived from practice of the present invention can be used for cancer diagnosis, prognosis, and in the design of cancer treatments.

In one aspect, the present invention provides a method for selecting a suitable anticancer drug for the treatment of a breast tumor, the method comprising:

(a) isolating cells of a breast tumor after administration of an anticancer drug, or prior to incubation with an anticancer drug;

(b) lysing the isolated cells to produce a cellular extract;

(c) detecting an activation state of one or more analytes in the cellular extract using an assay comprising a plurality of dilution series of capture antibodies specific for the one or more analytes, wherein the capture antibodies are restrained on a solid support; and (d) determining whether the anticancer drug is suitable or unsuitable for the treatment of the breast tumor by comparing the activation state detected for the one or more analytes with a reference activation profile generated in the absence of the anticancer drug.

In a preferred embodiment, the method for selecting a suitable anticancer drug for the treatment of a breast tumor comprises:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support;
(d) comparing the activation state detected for the one or more analytes with a reference activation profile generated in the absence of the anticancer drug; and
(e) indicating that the anticancer drug is suitable for the treatment of the breast tumor when the activation state detected for the one or more analytes is substantially decreased compared to the reference activation profile.

In some embodiments, the methods of the present invention may be useful to aid or assist in the selection of a suitable anticancer drug for the treatment of a breast tumor. In other embodiments, the methods of the present invention may be useful for improving the selection of a suitable anticancer drug for the treatment of a breast tumor.

In another aspect, the present invention provides a method for identifying the response of a breast tumor to treatment with an anticancer drug, the method comprising:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) identifying the breast tumor as responsive or non-responsive to treatment with the anticancer drug by comparing the activation state detected for the one or more analytes with a reference activation profile generated in the absence of the anticancer drug.

In a preferred embodiment, the method for identifying the response of a breast tumor to treatment with an anticancer drug comprises:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support;
(d) comparing the activation state detected for the one or more analytes with a reference activation profile generated in the absence of the anticancer drug; and
(e) indicating that the breast tumor is responsive to treatment with the anticancer drug when the activation state detected for the one or more analytes is substantially decreased compared to the reference activation profile.

In some embodiments, the methods of the present invention may be useful to aid or assist in the identification of a breast tumor's response to treatment with an anticancer drug. In other embodiments, the methods of the present invention may be useful for improving the identification of a breast tumor's response to treatment with an anticancer drug.

In yet another aspect, the present invention provides a method for predicting the response of a subject having a breast tumor to treatment with an anticancer drug, the method comprising:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) predicting the likelihood that the subject will respond to treatment with the anticancer drug by comparing the activation state detected for the one or more analytes with a reference activation profile generated in the absence of the anticancer drug.

In a preferred embodiment, the method for predicting the response of a subject having a breast tumor to treatment with an anticancer drug comprises:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support;
(d) comparing the activation state detected for the one or more analytes with a reference activation profile generated in the absence of the anticancer drug; and
(e) indicating that the subject will likely respond to treatment with the anticancer drug when the activation state detected for the one or more analytes is substantially decreased compared to the reference activation profile.

In some embodiments, the methods of the present invention may be useful to aid or assist in the prediction of a subject's likelihood of responding to treatment with an anticancer drug. In other embodiments, the methods of the present invention may be useful for improving the prediction of a subject's likelihood of responding to treatment with an anticancer drug.

In a further aspect, the present invention provides an array having superior dynamic range comprising a plurality of dilution series of capture antibodies restrained on a solid support, wherein the capture antibodies in each dilution series are specific for one or more analytes corresponding to a component of a signal transduction pathway or other protein (e.g., nuclear hormone receptor) in a cellular extract. The addressable arrays described herein are particularly useful for determining the expression and/or activation state of signal transduction molecules and other proteins involved in breast cancer.

In an additional aspect, the present invention provides a method for detecting the presence (or absence) of a truncated receptor, the method comprising:
(a) incubating a cellular extract with a plurality of beads specific for an extracellular domain (ECD) binding region of a full-length receptor;

(b) removing the plurality of beads from the cellular extract, thereby removing the full-length receptor to form a cellular extract devoid of the full-length receptor;

(c) incubating the cellular extract devoid of the full-length receptor with a plurality of capture antibodies, wherein the plurality of capture antibodies is specific for an intracellular domain (ICD) binding region of a truncated receptor and wherein the plurality of capture antibodies is restrained on a solid support to form a plurality of captured truncated receptors;

(d) incubating the plurality of captured truncated receptors with detection antibodies specific for the corresponding truncated receptors to form a plurality of detectable captured truncated receptors;

(e) incubating the plurality of detectable captured truncated receptors with first and second members of a signal amplification pair to generate an amplified signal; and (f) detecting an amplified signal generated from the first and second members of the signal amplification pair.

In a related aspect, the present invention provides a method for detecting the presence (or absence) of a truncated receptor, the method comprising:

(a) incubating a cellular extract with a plurality of beads specific for an extracellular domain (ECD) binding region of a full-length receptor;

(b) removing the plurality of beads from the cellular extract, thereby removing the full-length receptor to form a cellular extract devoid of the full-length receptor;

(c) incubating the cellular extract devoid of the full-length receptor with a plurality of capture antibodies, wherein the plurality of capture antibodies is specific for an intracellular domain (ICD) binding region of the truncated receptor and wherein the plurality of capture antibodies is restrained on a solid support to form a plurality of captured truncated receptors;

(d) incubating the plurality of captured truncated receptors with detection antibodies comprising a plurality of activation state-independent antibodies and a plurality of activation state-dependent antibodies specific for the corresponding truncated receptors to form a plurality of detectable captured truncated receptors, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(e) incubating the plurality of detectable captured truncated receptors with a second member of the signal amplification pair to generate an amplified signal; and (f) detecting the amplified signal generated from the first and second members of the signal amplification pair.

Other objects, features, and advantages of the present invention will be apparent to one of skill in the art from the following detailed description and figures.

BRIEF DESCRIPTION OF THE DRAWINGS

FIG. 5 shows a schematic example of an addressable array comprising dilutions of antibodies to components of a receptor tyrosine kinase pathway, such as those in the EGFR/MAPK/ERK pathway. Antibodies are plated in triplicate in four different dilutions on the addressable array.

FIG. 6 shows a schematic example of an addressable array comprising dilutions of antibodies to components of signal transduction pathways activated in tumor angiogenesis. Antibodies are plated in triplicate in four different dilutions on the addressable array.

FIG. 8 shows a schematic example of an addressable array comprising dilutions of antibodies to components of a receptor tyrosine kinase pathway and signal transduction pathways activated in tumor angiogenesis. Antibodies are plated in triplicate in four different dilutions on the addressable array.

FIG. 9 shows a schematic example of an alternative addressable array comprising dilutions of antibodies to components of a receptor tyrosine kinase pathway and signal transduction pathways activated in tumor angiogenesis. Antibodies may be plated in triplicate in a dilution series on the addressable array.

FIG. 21 shows ErbB expression/activation with EGF or HRG β treatment in various cell lines.

DETAILED DESCRIPTION OF THE INVENTION

I. Introduction

Figure 1:
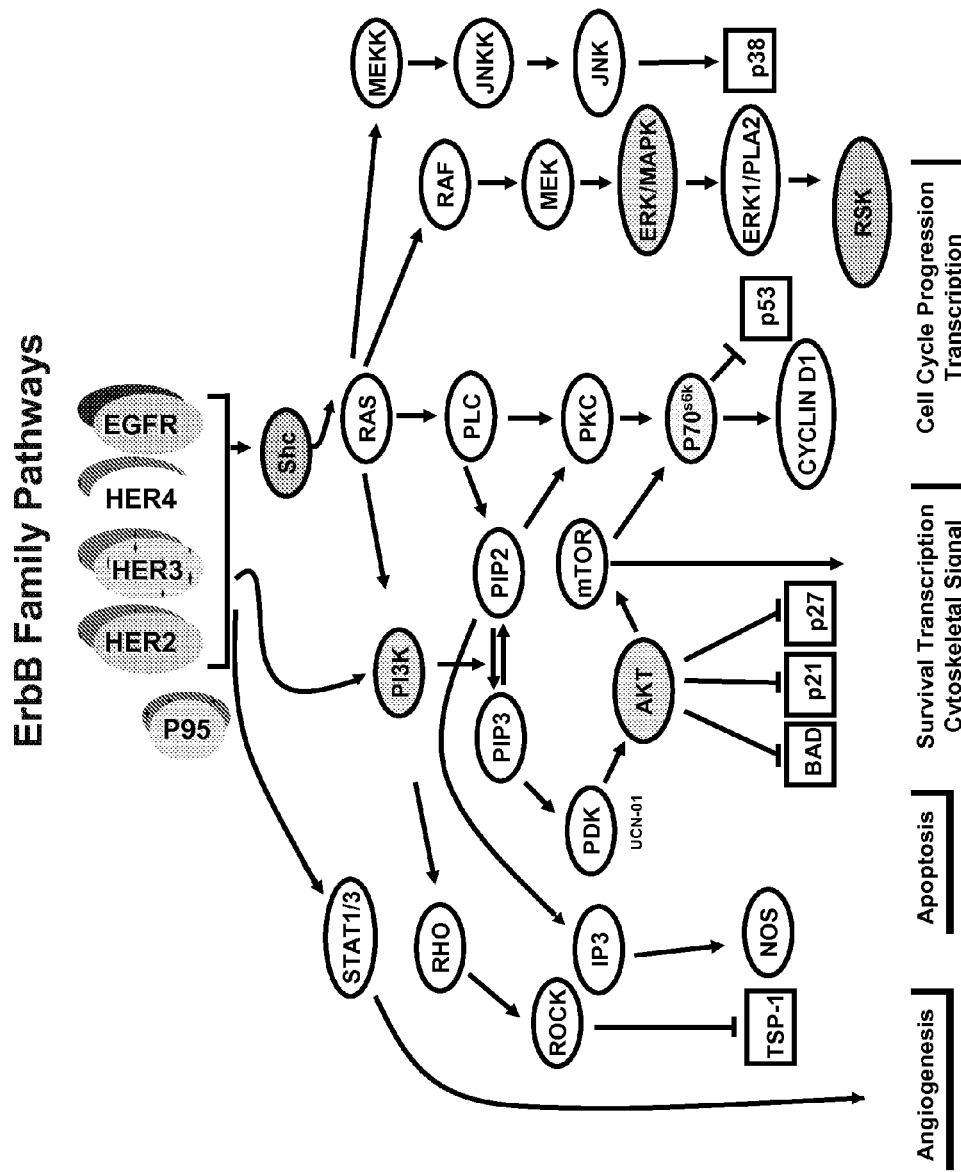
FIG. 1 shows an example of a signal transduction pathway involved in cell proliferation that may be used in the practice of the invention. Depicted are components of the EGFR/MAPK/ERK pathway that is used by cells to convert a mitogenic signal into cell proliferation.

As described above, the activation of signal transduction pathways that are involved in cell proliferation and the deactivation of pathways that are involved in cell death are non-limiting examples of molecular features that characterize many different types of cancer. In many cases, the activity of particular signal transduction pathways, and components thereof, may serve as molecular signatures for a given type of cancer. Such activated components may further provide useful targets for therapeutic intervention. Accordingly, knowledge of the activity level of a particular signal transduction system within a cancer cell prior to, during, and after treatment provides a physician with highly relevant information that may be used to select an appropriate course of treatment to adopt. Furthermore, the continued monitoring of signal transduction pathways that are active in cancer cells as treatment progresses can provide the physician with additional information on the efficacy of treatment, prompting the physician to either continue a particular course of treatment or to switch to another line of treatment, when, for example, cancer cells have become resistant to treatment through further aberrations that activate either the same or another signal transduction pathway.

Accordingly, the present invention provides methods and compositions for detecting the expression and activation states of a plurality of deregulated signal transduction molecules in tumor tissue or extratumoral cells such as rare circulating cells of a solid tumor in a specific, multiplex, high-throughput assay. The invention also provides methods and compositions for the selection of appropriate therapy (single drugs or combinations of drugs) to down-regulate or shut down a deregulated signaling pathway. Thus, the invention may be used to facilitate the design of personalized therapies for cancer patients.

The ability to detect and identify tumor cells in the circulation through the determination of the activity of signal transduction pathways at the level of single cells is an important advantage of the present invention. Tumor cells are often found in the blood of patients with various early stages of cancer as "micrometastases" (disseminated tumor cells) and are also found in metastatic cancers. The number of tumor cells in blood will depend on the stage and type of tumor. While biopsies are typically obtained on primary tumors, most metastatic tumors are not biopsied, making molecular analysis of such tumor samples very difficult. During tumor metastasis, the most aggressive tumor cells leave the primary tumor and travel through the blood and lymphatic system to reach a distant location. Thus, circulating tumor cells from blood represent the most aggressive and homogenous population of tumor cells. However, the number of metastatic tumor cells in blood is frequently very low, varying from one to several thousand cells per milliliter of blood. The ability to isolate and assay signal transduction pathways in such rare cells and to apply this information toward more effective cancer treatments is one object of the present invention.

In some embodiments, the multiplex, high-throughput immunoassays of the present invention can detect the activation state of one or more signal transduction molecules in circulating cells of a solid tumor at the single cell level. In fact, signal transduction molecules such as EGFR can be detected with a sensitivity of about 100 zeptomoles and a linear dynamic range of from about 100 zeptomoles to about 100 femtomoles. As such, single-cell detection of the activation state of multiple signal transducers in rare circulating cells facilitates cancer prognosis and diagnosis as well as the design of personalized, targeted therapies.

Rare circulating cells include circulating cells of a solid tumor that have either metastasized or micrometastasized from a solid tumor. Circulating tumor cells, cancer stem cells, and cells that are migrating to a tumor (e.g., due to chemoattraction) such as circulating endothelial progenitor cells, circulating endothelial cells, circulating pro-angiogenic myeloid cells, and circulating dendritic cells are some examples of circulating cells associated with a solid tumor.

Signal transduction molecules of interest are typically extracted shortly after the circulating cells are isolated to preserve their in situ activation state, preferably within about 24, 6, or 1 hr, and more preferably within about 30, 15, or 5 minutes. The isolated cells may also be incubated with one or more growth factors, usually at nanomolar to micromolar concentrations, for about 1-30 minutes to resuscitate or stimulate activation of the signal transduction molecules (see, e.g., Irish et al., *Cell,* 118:217-228 (2004)).

As explained in greater detail herein, to evaluate potential anticancer therapies for an individual patient, the isolated cells can be incubated with one or more anticancer drugs at varying doses. Growth factor stimulation can then be performed for a few minutes (e.g., about 1-5 minutes) or for several hours (e.g., about 1-6 hours). The differential activation of signaling pathways with and without anticancer drugs can aid in the selection of a suitable cancer therapy at the proper dose for each individual patent. Circulating cells can also be isolated from a patient sample during anticancer drug treatment and stimulated with one or more growth factors to determine whether a change in therapy should be implemented. As such, the methods of the present invention advantageously assist the clinician in providing the right anticancer drug at the right dose at the right time for every patient.

With regard to breast cancer, current testing options are unsatisfactory because treatment of both primary and metastatic tumors in a breast cancer patient is based on a one-time diagnosis from a biopsy sample taken during an early stage of the disease. In particular, therapeutic intervention for both the early and metastatic stages of breast cancer is based solely on the initial diagnosis from the biopsy sample taken during an early stage of the disease because of the impracticality of obtaining a biopsy sample from a metastatic cancer patient. However, breast tumors are evolving as a function of time and treatment such that temporal monitoring of breast tumors is critical for optimal management of breast cancer patients. For example, a change in the activation state of one or more of the ErbB (HER) family of receptor tyrosine kinases may affect therapy selection at recurrence. Indeed, discordance in HER-2 status between primary and metastatic cancer is common because up to 37% of all breast cancer patients change from a HER-2-negative primary tumor to HER-2-positive metastatic cancer. In addition, patients may have de novo resistance or develop acquired resistance to hormonal therapy due to HER-1/2 activation. In some instances, patients may have de novo resistance or develop acquired resistance to ErbB-targeted therapies due to the presence of tumor cells expressing p95HER-2. As a result, there is an unmet clinical need for assays to assist the clinician in prescribing the appropriate cancer therapy at the appropriate time because current technology lacks sensitivity and specificity, cannot be used to monitor patients on therapy, and do not utilize pathway profiling to guide individualized treatment decisions.

In contrast to currently available breast cancer testing options, the methods of the present invention enable the monitoring of breast cancer patients through all stages of the disease by providing a "real-time biopsy" of solid breast tumors using samples such as circulating tumor cells (CTCs) from blood and/or fine needle aspirates (FNAs). As a non-limiting example, the breast cancer assays described herein can be used in the initial diagnosis of breast cancer in a patient at an early stage of the disease. Selection of a suitable cancer therapy is guided by profiling the activation states of specific signaling pathways with and without anticancer drugs using the single detection and proximity dual detection assays described herein. Advantageously, the methods of the present invention can also be used to monitor the progression or regression of the disease because therapeutic intervention may be based on samples taken at any stage of the disease and analyzed using the single detection and proximity dual detection assays described herein. As such, selection of suitable cancer therapies for the early and metastatic stages of breast cancer is guided by real-time diagnosis and an analysis of the activation status of specific signaling pathway molecules.

The methods of the present invention are beneficially tailored to address key issues in cancer management and provide a higher standard of care for breast cancer patients because they (1) provide increased sensitivity (e.g., single cell detection can be achieved for detecting total and phosphorylated signal transduction molecules such as EGFR and HER-2), (2) provide increased specificity (e.g., three-antibody proximity assays enhance specificity for detecting phosphorylated signal transduction molecules), (3) enable pathway profiling (e.g., activation status of specific signal transduction molecules can be detected in CTCs or FNA from patients), and (4) eliminate any issues with obtaining patient samples (e.g., assays can be performed on a few tumor cells). Although any sample may be used in the novel assays described herein, CTCs are particularly useful because they represent the most aggressive tumor cells, every tumor is known to shed CTCs, they can be the only source of residual tumors or hard-to-access metastatic tumors, and they are found in blood. As such, the methods of the present invention enable the serial sampling of breast tumor tissues, resulting in valuable information on changes occurring in tumor cells as a function of time and therapy and providing clinicians with a means to monitor rapidly evolving cancer pathway signatures.

In sum, the methods of the present invention advantageously provide accurate selection and monitoring of cancer patients (e.g., breast cancer patients) most likely to benefit from targeted therapy by performing pathway profiling on easily accessible tumor cells using multiplexed, antibody-based single detection or proximity assays.

II. Definitions

As used herein, the following terms have the meanings ascribed to them unless specified otherwise.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, breast cancer; lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells. In one preferred embodiment, the breast tumor is derived from a subject with an invasive or in situ form of ductal carcinoma or lobular carcinoma. In another preferred embodiment, the breast tumor is derived from a subject with recurrent or metastatic breast cancer.

The term "analyte" includes any molecule of interest, typically a macromolecule such as a polypeptide, whose presence, amount, and/or identity is determined. In certain instances, the analyte is a cellular component of circulating cells of a solid tumor, preferably a signal transduction molecule.

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "superior dynamic range" as used herein refers to the ability of an assay to detect a specific analyte in as few as one cell or in as many as thousands of cells. For example, the immunoassays described herein possess superior dynamic range because they advantageously detect a particular signal transduction molecule of interest in about 1-10,000 cells (e.g., about 1, 5, 10, 25, 50, 75, 100, 250, 500, 750, 1000, 2500, 5000, 7500, or 10,000 cells) using a dilution series of capture antibody concentrations.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER-1/ErbB1, HER-2/Neu/ErbB2, HER-3/ErbB3, HER-4/ErbB4), VEGFR-1/FLT-1, VEGFR-2/FLK-1/KDR, VEGFR-3/FLT-4, FLT-3/FLK-2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR 1-2, MUSK, AATYK 1-3, RTK 106, and truncated forms of the receptor tyrosine kinases such as p95ErbB2; non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as Akt, MAPK/ERK, MEK, RAF, PLA2, MEKK, JNKK, JNK, p38, Shc (p66), PI3K, Ras (e.g., K-Ras, N-Ras, H-Ras), Rho, Rac1, Cdc42, PLC, PKC, p70 S6 kinase, p53, cyclin D1, STAT1, STAT3, PIP2, PIP3, PDK, mTOR, BAD, p21, p27, ROCK, IP3, TSP-1, NOS, PTEN, RSK 1-3, JNK, c-Jun, Rb, CREB, Ki67, and paxillin; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors such as amplified in breast cancer-1 (AIB1) and nuclear receptor corepressor 1 (NCOR), respectively; and combinations thereof.

As used herein, the term "circulating cells" comprises extratumoral cells that have either metastasized or micrometastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.).

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), and cellular extracts thereof. In some embodiments, the sample is whole blood or a fractional component thereof such as plasma, serum, or a cell pellet. In preferred embodiments, the sample is obtained by isolating circulating cells of a solid tumor from whole blood or a cellular fraction thereof using any technique known in the art. In other embodiments, the sample is a formalin fixed paraffin embedded (FFPE) tumor tissue sample, e.g., from a solid tumor of the breast.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

The term "subject" or "patient" or "individual" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays of the present invention typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract of circulating cells of a solid tumor. In preferred embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, Akt, MAPK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. Non-limiting examples of activation states (listed in parentheses) that are suitable for detection with activation state-dependent antibodies include: EGFR (EGFRvIII, phosphorylated (p-) EGFR, EGFR:Shc, ubiquitinated (u-) EGFR, p-EGFRvIII); ErbB2 (p95:truncated (Tr)-ErbB2, p-ErbB2, p95:Tr-p-ErbB2, HER-2:Shc, ErbB2:PI3K, ErbB2:EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); ER (p-ER (S118, S167); IGF-1R (p-IGF-1R, IGF-1R:IRS, IRS:PI3K, p-IRS, IGF-1R:PI3K); INSR (p-INSR); KIT (p-KIT); FLT3 (p-FLT3); HGFR1 (p-HGFR1); HGFR2 (p-HGFR2); RET (p-RET); PDGFRa (p-PDGFRa); PDGFRP (p-PDGFRP); VEGFR1 (p-VEGFR1, VEGFR1:PLCg, VEGFR1:Src); VEGFR2 (p-VEGFR2, VEGFR2:PLCy, VEGFR2:Src, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); Tie1 (p-Tie1); Tie2 (p-Tie2); EphA (p-EphA); EphB (p-EphB); NFKB and/or IKB (p-IK (S32), p-NFKB (S536), p-P65:IKBa); Akt (p-Akt (T308, S473)); PTEN (p-PTEN); Bad (p-Bad (S112, S136), Bad:14-3-3); mTor (p-mTor (S2448)); p70S6K (p-p70S6K (T229, T389)); Mek (p-Mek (S217, S221)); Erk (p-Erk (T202, Y204)); Rsk-1 (p-Rsk-1 (T357, S363)); Jnk (p-Jnk (T183, Y185)); P38 (p-P38 (T180, Y182)); Stat3 (p-Stat-3 (Y705, S727)); Fak (p-Fak (Y576)); Rb (p-Rb (S249, T252, S780)); Ki67; p53 (p-p53 (5392, S20)); CREB (p-CREB (S133)); c-Jun (p-c-Jun (S63)); cSrc (p-cSrc (Y416)); and paxillin (p-paxillin (Y118)).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

The term "nucleic acid" or "polynucleotide" includes deoxyribonucleotides or ribonucleotides and polymers thereof in either single- or double-stranded form such as, for example, DNA and RNA. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof and complementary sequences as well as the sequence explicitly indicated.

The term "oligonucleotide" refers to a single-stranded oligomer or polymer of RNA, DNA, RNA/DNA hybrid, and/or a mimetic thereof. In certain instances, oligonucleotides are composed of naturally-occurring (i.e., unmodified) nucleobases, sugars, and internucleoside (backbone) linkages. In certain other instances, oligonucleotides comprise modified nucleobases, sugars, and/or internucleoside linkages.

As used herein, the term "mismatch motif" or "mismatch region" refers to a portion of an oligonucleotide that does not have 100% complementarity to its complementary sequence. An oligonucleotide may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "stringent hybridization conditions" refers to conditions under which an oligonucleotide will hybridize to its complementary sequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region) when compared and aligned for maximum correspondence over a comparison window or designated region as measured using a sequence comparison algorithm or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

The term "incubating" is used synonymously with "contacting" and "exposing" and does not imply any specific time or temperature requirements unless otherwise indicated.

III. Description of the Embodiments

In one embodiment, the present invention provides methods for detecting the expression and activation states of a plurality of deregulated signal transducers in tumor cells derived from tumor tissue or circulating cells of a solid tumor in a specific, multiplex, high-throughput assay. The invention also provides methods and compositions for the selection of appropriate therapies to down-regulate or shut down one or more deregulated signaling pathways. Thus, embodiments of the invention may be used to facilitate the design of personalized therapies based on the particular molecular signature provided by the collection of activated signal transduction proteins in a given patient's tumor.

Circulating cells of a solid tumor include cells that have either metastasized or micrometastasized from a solid tumor, including cancer stem cells or cells that are migrating to the tumor (e.g., due to chemoattraction), such as endothelial progenitor cells, circulating endothelial cells, pericytes, circulating pro-angiogenic myeloid cells, dendritic cells, etc. Patient samples containing the circulating cells can be obtained from any accessible biological fluid (e.g., whole blood, serum, plasma, sputum, bronchial lavage fluid, urine, nipple aspirate, lymph, saliva, fine needle aspirate, etc.). In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs), circulating endothelial cells (CECs), circulating endothelial progenitor cells (CEPCs), cancer stem cells (CSCs), disseminated tumor cells of the lymph node, and combinations thereof. The plasma or serum fraction usually contains, inter alia, nucleic acids (e.g., DNA, RNA) and proteins that are released by circulating cells of a solid tumor.

The circulating cells are typically isolated from a patient sample using one or more separation methods including, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), the CellTracks® System by Immunicon (Huntingdon Valley, Pa.), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)).

To preserve the in situ activation states, the signal transducers are advantageously extracted shortly after the cells are isolated, preferably within 96, 72, 48, 24, 6, or 1 hr, more preferably within 30, 15, or 5 minutes. The isolated cells may also be advantageously incubated with growth factors usually at nanomolar to micromolar concentrations for about 1-30 minutes to resuscitate or stimulate signal transducer activation (see, e.g., Irish et al., *Cell*, 118:217-228 (2004)). Stimulatory growth factors include epidermal growth factor (EGF), heregulin (HRG), TGF-α, PIGF, angiopoietin (Ang), NRG1, PGF, TNF-α, VEGF, PDGF, IGF, FGF, HGF, cytokines, and the like. To evaluate potential anticancer therapies for an individual patient, prior to growth factor stimulation, the isolated cells can be incubated with one or more anticancer drugs of varying doses. Growth factor stimulation can be performed for a few minutes or hours (e.g., 1-5 minutes to 1-6 hours). The differential activation of signaling pathways with and without anticancer drugs aids in the selection of a suitable cancer therapy at the proper dose for each individual patent. After isolation, anticancer agent treatment, and/or growth factor stimulation, the cells are lysed to extract the signal transducers using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the lysate can be stored at −80° C. until use.

In some embodiments, the anticancer drug comprises an agent that interferes with the function of activated signal transduction pathway components in cancer cells. Non-limiting examples of such agents include those listed below in Table 1.

TABLE 1

| EGFR (ErbB1) (A) | HER-2 (ErbB2) (C) | HER-3 (ErbB3) (E) | HER-4 (ErbB4) target |
|---|---|---|---|
| Cetuximab<br>Panitumumab<br>Matuzumab<br>Nimotuzumab<br>ErbB1 vaccine | Trastuzumab<br>(Herceptin ®)<br>Pertuzumab (DNA)<br>BMS-599626*<br><br>*Heterodimerization HER-½;<br>Phase 1 | Antibody (U3) | |

| EGFR (ErbB1) (B) | HER-2 (ErbB2) (D) | ErbB½ (F) | ErbB1/2/4 (G) |
|---|---|---|---|
| Erlotinib<br>Gefitinib<br>EKB 569*<br>CL-387-785**<br>*(Wyeth, Irreversible, II CRC)<br>**(Wyeth, Irreversible, Preclinical) | CP-724714 (Pfizer) | Lapatinib (Tykerb ®)<br>HKI-272*<br>HKI-357 (Preclinical)<br>BIBW 2992**<br>*Wyeth, Irreversible, I/II NSCLC, Breast<br>**Boehringer Ingelheim, Irreversible, I/II Prostate, Ovarian, Breast | Canertinib*<br>ARRY-334543<br>JNJ-26483327<br>JNJ-26483327<br>*Pfizer, Irreversible, II NSCLC, Breast |

| Raf (H) | SRC (H) | Mek: (I) | NFkB-IkB (I) |
|---|---|---|---|
| Sorafenib<br>PLX4032 (Plexxikon) | AZ | PD-325901 (II: NSCLC)<br>AZD6244-Array/Az<br>XL518 Exelisis/DNA<br>VEGFR2 and | |

| mTor (J) | PI3K (J) | VEGFR1 (K) | VEGFR1/2/3: |
|---|---|---|---|
| Rad 001: Everolimus*<br>Temsirolimus<br>AP-23573*<br>*Everolimus (Novartis, combination with Gefetinib/Erlotinib; I/II: NSCLC, Glioblastoma)<br>**Temsirolimus (Wyeth, combination with Gefetinib/Erlotinib; I/II: NSCLC, Glioblastoma) | PX-866*<br><br>*P110alpha specific inhibition; ProlX Pharma; Preclinical NSCLC | Avastin (DNA)<br>HuMV833*<br>VEGF-Trap**<br>*(PDL) anti-VEGFa<br>**Regeneron/Aventis (Receptor mimic)<br>(Phase 2) | AZD 2171 (NSCLC, CRC)<br>AMG-706 (+ PDGFR) |

TABLE 1-continued

***AP-23573 (Ariad, I/II: Endometrial)

|  | VEGFR2 target (L) |  | EPH A-D |
|---|---|---|---|
| DC101* | CDP-791 (UCB) | Bay-579352 (+ PDGFR) |  |
| IMC-IC11** | CP-547632* | ABT-869* |  |
| IMC1121B Fully humanized | AG13736** | BMS-540215 (+FGFR1) |  |
| CDP-791*** | E-7080 (Eisai) | KRN-951 |  |
| Pazopanib**** | CHIR-258*** | BBIW |  |
| *Imclone (Phase 2/3?) | OSI-930 (+ cKit, PDGFR) |  |  |
| **Chimeric IgG1 against VEGFR2 | *OSI, PFIZER: (+ ErbB1 + PDGFR) (NSCLC, Ovarian Phase 2) | *(+CSF1R, Erk, Flt-3, PDGFR) |  |
| ***Celltech, pegalated di-Fab antibody against R2 | **Pfizer: VEGFR1,2 and PDGFRbeta) (RCC II) |  |  |
| ****GSK, Multiple myeloma, ovarian, RCC Phase 3 enrollment completed, sarcoma II) | ***(VEGFR1,2 FGFR3, PDGFR) |  |  |

| VEGFR 2/ErbB½ (ErbB1)/cMet/FGFR (M) | VEGFR2/3/Raf/PDGFR/cKit/Flt-3 (N) | TIE ½ | VEGFR2/1/3, Flt-3, cFMS, PDGFR/cKit (O) |
|---|---|---|---|
| ZD6474* | Sorafenib* |  | PTK787 (Not cFMS, FLT-3) |
| XL647** |  |  | Sunitinib |
| AEE 788*** |  |  | XL-999 |
|  |  |  | SU-6668 (Pfizer) |
|  |  |  | GSK |
|  |  |  | AZ (AZD2171) |
|  |  |  | BMS |
|  |  |  | Novartis (AEE-788) |
|  |  |  | Amgen |
|  |  |  | Others |
| *(vandetanib) (Phase III: thyroid, NSCLC) | *(RCC, HCC, NSCLC(III), Melanoma(III)) |  |  |
| **(Exelixis; Also EPHB2): (Patient resistant to Erlotinib; Asian patients) (Phase 2) |  |  |  |
| ***(Novartis, Phase ½) |  |  |  |

| PDGFR target (P) | Abl target: (Q) | FTL 3 | RET |
|---|---|---|---|
| Tandutinib | Imatinib |  |  |
| Nilotinib | Dasatinib |  |  |
|  | Nilotinib |  |  |
|  | AT-9283 |  |  |
|  | AZD-0530 |  |  |
|  | Bosutinib |  |  |

| Kit target (R) | HGFR½ | FGFR1-4 | IGF-1R Target (S) |
|---|---|---|---|
| AMG-706 |  | Chiron | Merck |
| XL-880 |  |  | Pfizer |
| XL-999 |  |  | Novartis |

| HSP90 inhibitors: | Anti-Mitotic Drugs: | Other targets: |
|---|---|---|
| IPI-504* | Docetaxel* | HDAC inhibitors |
| 17-AAG** | Paclitaxel** | BCL2 |
|  | Vinblastine, Vincristine, Vinorelbine*** | Chemotherapeutics (breakdown) |
|  |  | Proteosome inhibitors |
| *(Infinity Pharma, Mutant ErbB1, I/II multiple myeloma, GIST) | *(Microtubule stabilizer; Adjuvant and advanced Breast cancer; NSCLC, Androgen independent Prostate cancer) |  |
| **(Kosan, I/II solid tumors) | **(Microtubule stabilizer; Adjuvant and advanced Breast cancer; NSCLC, Ovarian cancer, AIDS related Kaposi sarcoma) |  |
|  | ***(Microtubule De-stabilizers) |  |

In another embodiment, the present invention provides an addressable array having superior dynamic range comprising a plurality of dilution series of capture antibodies restrained on a solid support, in which the capture antibodies in each dilution series are specific for one or more analytes corresponding to a component of a signal transduction pathway and other target proteins. In various aspects, this embodiment includes arrays that comprise components of signal transduction pathways characteristic of particular tumors, e.g., signal transduction pathways active in breast cancer cells. Thus, the invention may be advantageously practiced wherein each signal transduction molecule or other protein of interest with a potential expression or activation defect causing cancer is represented on a single array or chip. In some aspects, the components of a given signal transduction pathway active in a particular tumor cell are arrayed in a linear sequence that corresponds to the sequence in which information is relayed through a signal transduction pathway within a cell. Examples of such arrays are shown in FIGS. 5-9. The capture antibodies specific for one or more components of a given signal transduction pathway active in a particular tumor cell can also be printed in a randomized fashion to minimize any surface-related artifacts.

Non-limiting examples of signal transduction pathways that may be interrogated using the present invention include those shown in Table 2.

TABLE 2

| | | | | | | | | |
|---|---|---|---|---|---|---|---|---|
| Pathway 1 | ErbB1 | ErbB1 Phospho | ErbB1 Shc | ErbB1 ubiquitin | ErbB1-PI3K | PTEN | | |
| Pathway 2 | ErbB1 | ErbB1VIII | ErbB1VIII Phospho | ErbB1VIII Shc | ErbB1VIII ubiquitin | ErbB1VIII PI3K | PTEN | |
| Pathway 3 | ErbB2 | ErbB2 Phospho | HER-2 Shc | ErbB2: PI3K Complex | ErbB2 ubiquitin | PTEN | | |
| Pathway 4 | ErbB2 | P95Truncated ErbB2 | ErbB2Phospho | P95Truncated ERBB2 Phospho | HER-2 Shc | ERBB2: PI3K Complex | ErbB2 ubiquitin | P95ErbB2: PI3K |
| Pathway 5 | ErbB3 | ErbB3 Phospho | ErbB3: PI3K Complex | ErbB3 PI3K Phospho | ErbB3: Shc | | | |
| Pathway 6 | ErbB4 | ErbB4 Phospho | ErbB4: Shc | | | | | |
| Pathway 7 | IGF-1R | IGF-1RPhospho | IGF-1R: IRS | IRS: PI3K | Phospho IRS | IGF-1R: PI3K | | |
| Pathway 8 | INSR | INSRPhospho | | | | | | |
| Pathway 9 | KIT | KIT Phospho | | | | | | |
| Pathway 10 | FLT3 | FLT3Phospho | | | | | | |
| Pathway 11 | HGFR 1 | HGFR 1 Phospho | | | | | | |
| Pathway 12 | HGFR 2 | HGFR 2 Phospho | | | | | | |
| Pathway 13 | RET | RET Phospho | | | | | | |
| Pathway 14 | PDGFR alpha | PDGFR alpha Phospho | | | | | | |
| Pathway 15 | PDGFR beta | PDGFR beta Phospho | | | | | | |
| Pathway 16 | VEGFR 1 | VEGFR 1 Phospho | VEGFR 1: PLCγcomplex | VEGFR 1: Src | | | | |
| Pathway 17 | VEGFR 2 | VEGFR 2 Phospho | VEGFR 2: PLCγ complex | VEGFR 2: Src | VEGFR-2/heparin sulphate complex | VEGFR-2, VE-cadherin complex | | |
| Pathway 18 | VEGFR 3 | VEGFR 3 Phospho | | | | | | |
| Pathway 19 | FGFR 1 | FGFR 1 Phospho | | | | | | |
| Pathway 20 | FGFR 2 | FGFR 2 Phospho | | | | | | |
| Pathway 21 | FGFR 3 | FGFR 3 Phospho | | | | | | |
| Pathway 22 | FGFR 4 | FGFR 4 Phospho | | | | | | |
| Pathway 23 | TIE 1 | TIE 1 Phospho | | | | | | |
| Pathway 24 | TIE 2 | TIE 2 Phospho | | | | | | |
| Pathway 25 | EPHA | EPHA Phospho | | | | | | |
| Pathway 26 | EPHB | EPHB Phospho | | | | | | |
| Pathway 27 | NFκB-IkB complex | phospho-IκB (S32) Total IkB | Total NFκB Phospho NFκB(S536) | Total P65 IkBa Phospho P65 IkBa | | | | |
| Pathway 28 | ER | Phospho ER | ER-AIB1 | Other ER complexes | | | | |
| Pathway 29 | PR | Phospho Pr | | PR complexes | | | | |
| Pathway 30 | Hedgehog Pathway | | | | | | | |
| Pathway 31 | Wnt pathway | | | | | | | |

TABLE 2-continued

| | | | | | | | | |
|---|---|---|---|---|---|---|---|---|
| Pathway 32 | Notch Pathway | | | | | | | |
| Pathway 33 | Total Mek Phospho Mek (S217/S221) | Total Erk Phospho Erk (T202/Y204) | Total Rsk-1 Phospho Rsk-1 (T357/S363) | Total Stat3 Phospho Stat-3 (Y705) (S727) Total Stat 1 Phospho Stat1 (Y 701) | Phospho Bad (S112) Bad (total) | Total Fak Phospho Fak (Y576) | Total cSrc Phospho cSrc(Y416) | Total Ras Phospho Ras |
| Pathway 34 | Akt (Total) Phospho Akt (T473) | Phospho Akt (T308) | Phospho Bad (S112) Bad (total) | Phospho Bad (S136) | Bad: 14-3-3 complex | Total mTor Phospho mTor (S2448) | Total p70S6K Phospho p70S6K (T229) (T389) | GSK3beta Total (Phospho Ser 9) |
| Pathway 35 | Total Jnk Phospho Jnk (T183/Y185) | Total P38 Phospho P38 (T180/Y182) | Total Rb Phospho Rb (S249/T252) Phospho Rb (S780) | Total p53 Phospho p53 (S392) Phospho p53 (S20) | phospho-CREB(S133) Total CREB | Total c-Jun phospho-c-Jun; (S63) | Total Paxillin Phospho Paxillin (Y118) | |
| Pathway 36 | Ki67 | Cleaved Caspase 3, 8, 9 others | TOPO2 | | | | | |
| Pathway 37 | TGFbeta | | | | | | | |

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the isolated circulating cells are treated with one or more anti-signaling agents, anti-proliferative agents, and/or hormonal therapeutic agents in combination with at least one chemotherapeutic agent.

Examples of anti-signaling agents suitable for use in the present invention include, without limitation, monoclonal antibodies such as trastuzumab (Herceptin®), alemtuzumab (Campath®), bevacizumab (Avastin®), cetuximab (Erbitux®), gemtuzumab (Mylotarg®), panitumumab (Vectibix™), rituximab (Rituxan®), and tositumomab (BEXXAR®); tyrosine kinase inhibitors such as gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), imatinib mesylate (Gleevec®), leflunomide (SU101), and vandetanib (ZACTIMA™; ZD6474); and combinations thereof.

Exemplary anti-proliferative agents include mTOR inhibitors such as sirolimus (rapamycin), temsirolimus (CCI-779), and everolimus (RAD001); Akt inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl)methyl)-4-piperidinyl)-2H-benzimidazol-2-one, 10-(4'-(N-diethylamino)butyl)-2-chlorophenoxazine, 3-formylchromone thiosemicarbazone (Cu (II)Cl$_2$ complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125:1144-1145 (2003) and Kau et al., *Cancer Cell*, 4:463-476 (2003), and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, without limitation, aromatase inhibitors (e.g., aminoglutethimide, anastrozole (Arimidex®), letrozole (Femara®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Non-limiting examples of cancer vaccines useful in the present invention include ANYARA from Active Biotech, DCVax-LB from Northwest Biotherapeutics, EP-2101 from IDM Pharma, GV1001 from Pharmexa, IO-2055 from Idera Pharmaceuticals, INGN 225 from Introgen Therapeutics and Stimuvax from Biomira/Merck.

Examples of radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto the array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.).

In some embodiments, the cellular extract comprises an extract of circulating cells of a solid tumor. The circulating cells are typically isolated from a patient sample using one or more separation methods known in the art including, for example, immunomagnetic separation, the CellTracks® System, microfluidic separation, FACS, density gradient centrifugation, and depletion methods.

In other embodiments, the patient sample comprises a bodily fluid sample such as, for example, a whole blood, serum, plasma, ductal lavage fluid, nipple aspirate, lymph, bone marrow aspirate, urine, saliva, and/or fine needle aspirate sample. In certain instances, the whole blood sample is separated into a plasma or serum fraction and a cellular fraction (i.e., cell pellet). The cellular fraction typically contains red blood cells, white blood cells, and/or circulating cells of a solid tumor such as CTCs, CECs, CEPCs, disseminated tumor cells of the lymph node, and/or CSCs. The plasma or serum fraction usually contains, inter alia, nucleic acids (e.g., DNA, RNA) and proteins that are released by circulating cells of a solid tumor.

In some instances, the isolated circulating cells can be stimulated in vitro with one or more growth factors before, during, and/or after incubation with one or more anticancer drugs of interest. Stimulatory growth factors are described above. In other instances, the isolated circulating cells can be lysed, e.g., following growth factor stimulation and/or anticancer drug treatment, to produce the cellular extract (e.g., cell lysate) using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the cell lysate can be stored at −80° C. until use.

In preferred embodiments, the expression and/or activation states of a plurality of signal transduction molecules in tumor cells such as circulating cells of a solid tumor are detected using a single detection or proximity dual detection assay as described below.

Accordingly, in one aspect, the present invention provides a method for selecting a suitable anticancer drug for the treatment of a breast tumor, the method comprising:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) determining whether the anticancer drug is suitable or unsuitable for the treatment of the breast tumor by comparing the activation state detected for the one or more analytes with a reference activation profile generated in the absence of the anticancer drug.

In certain instances, the methods of the present invention may further comprise sending or reporting the results of step (d) to a clinician, e.g., an oncologist or a general practitioner. In certain other instances, the methods of the present invention may further comprise recording or storing the results of step (d) in a computer database or other suitable machine or device for storing information, e.g., at a laboratory.

In a preferred embodiment, the method for selecting a suitable anticancer drug for the treatment of a breast tumor comprises:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support;
(d) comparing the activation state detected for the one or more analytes with a reference activation profile generated in the absence of the anticancer drug; and
(e) indicating that the anticancer drug is suitable for the treatment of the breast tumor when the activation state detected for the one or more analytes is substantially decreased compared to the reference activation profile.

In certain instances, the preferred embodiment may further comprise, i.e., as step (f), or alternatively comprise, i.e., as step (e), the step of indicating that the anticancer drug is unsuitable for the treatment of the breast tumor when the activation state detected for the one or more analytes is not substantially decreased compared to the reference activation profile.

In certain other instances, the preferred embodiment may further comprise sending or reporting the results of step (e) to a clinician, e.g., an oncologist or a general practitioner. In yet other instances, the preferred embodiment may further comprise recording or storing the results of step (e) in a computer database or other suitable machine or device for storing information, e.g., at a laboratory.

In some embodiments, the activation state of an analyte such as a signal transduction molecule is considered to be "substantially decreased" in the presence of an anticancer drug when it is at least about 50%, 55%, 60%, 65%, 70%, 75%, 80%, 85%, 90%, or 95% less activated than in the absence of the anticancer drug. In other embodiments, the activation state of an analyte such as a signal transduction molecule is considered to be "substantially decreased" in the presence of an anticancer drug (1) when there is a change from high or strong activation of the analyte without the anticancer drug to medium, weak, low, or very weak activation of the analyte with the anticancer drug, or (2) when there is a change from medium activation of the analyte without the anticancer drug to weak, low, or very weak activation of the analyte with the anticancer drug.

In some embodiments, the methods of the present invention may further comprise the step of obtaining a sample from a subject having a breast tumor from which cells of a breast tumor are isolated. The sample may be obtained from a breast cancer subject either before anticancer drug treatment (e.g., prior to incubation with an anticancer drug) or after administration of an anticancer drug (e.g., at any time throughout the course of cancer treatment). Suitable samples include, but are not limited to, whole blood, serum, plasma, ductal lavage fluid, nipple aspirate, lymph, bone marrow aspirate, urine, saliva, fine needle aspirate (FNA), and combinations thereof. In one preferred embodiment, the sample is a whole blood or FNA sample. In this embodiment, circulating cells of a breast tumor may be isolated from the whole blood sample or breast cancer cells may be isolated from the FNA sample. If isolated cells are obtained from a subject who has not received treatment with an anticancer drug, the isolated cells may be incubated in vitro under suitable conditions with one or a cocktail of anticancer drugs which target one or more of the analytes to be detected in step (c).

Circulating cells of a breast tumor may be isolated from a sample by any technique known in the art, e.g., by immunomagnetic separation, the CellTracks® System, microfluidic separation, FACS, density gradient centrifugation, and depletion methods (see, Example 1). Examples of circulating cells that may be isolated from a sample include, without limitation, circulating tumor cells, circulating endothelial cells, circulating endothelial progenitor cells, cancer stem cells, disseminated tumor cells, and combinations thereof. Isolated cells such as circulating cells may be lysed to thereby transform the isolated cells into a cellular extract by any technique known in the art (see, Example 1).

In one embodiment, the breast tumor is derived from a subject with ductal carcinoma or lobular carcinoma. Examples of ductal carcinomas include, but are not limited to, invasive ductal carcinoma and ductal carcinoma in situ. Non-limiting examples of lobular carcinomas include invasive lobular carcinoma or lobular carcinoma in situ.

In certain instances, the cells of a breast tumor are isolated from tumor tissue. The tumor tissue may be, e.g., primary tumor tissue or metastatic tumor tissue. In a preferred embodiment, the cells are isolated from tumor tissue as a fine needle aspirate (FNA) sample.

In some embodiments, the isolated cells are stimulated in vitro with growth factors as described herein. In other embodiments, the anticancer drug may comprise one or more of the therapeutic agents described herein, including but not limited to monoclonal antibodies, tyrosine kinase inhibitors, chemotherapeutic agents, hormonal therapeutic agents, radiotherapeutic agents, and vaccines.

In preferred embodiments, the one or more analytes present in the cellular extract comprise a plurality of signal transduction molecules. Examples of signal transduction molecules include, without limitation, receptor tyrosine kinases, non-receptor tyrosine kinases, tyrosine kinase signaling cascade components, nuclear hormone receptors, nuclear receptor coactivators, nuclear receptor repressors, and combinations thereof. In certain instances, the plurality of signal transduction molecules is selected from the group consisting of EGFR (ErbB1), HER-2 (ErbB2), p95ErbB2, HER-3 (ErbB3), HER-4 (ErbB4), Raf, SRC, Mek, NFkB-IkB, mTor, PI3K, VEGF, VEGFR-1, VEGFR-2, VEGFR-3, Eph-a, Eph-b, Eph-c, Eph-d, cMet, FGFR, cKit, Flt-3, Tie-1, Tie-2, Flt-3, cFMS, PDGFRA, PDGFRB, Abl, FTL 3, RET, Kit, HGFR, FGFR1, FGFR2, FGFR3, FGFR4, IGF-1R, ER, PR, NCOR, AIB1, and combinations thereof. Preferably, the plurality of signal transduction molecules is selected from the group consisting of ErbB1, ErbB2, p95ErbB2, ErbB3, ErbB4, VEGFR-1, VEGFR-2, VEGFR-3, ER, PR, and combinations thereof.

In some embodiments, the activation state detected for the one or more analytes present in the cellular extract may be, e.g., a phosphorylation state, a ubiquitination state, a complexation state, or combinations thereof. In other embodiments, the solid support may comprise, e.g., glass, plastic, chips, pins, filters, beads, paper, membrane, fiber bundles, and combinations thereof. In yet other embodiments, the capture antibodies are restrained on the solid support in an addressable array.

In certain embodiments, the assay in step (c) comprises:
(i) incubating (e.g., contacting) the cellular extract with the plurality of dilution series of capture antibodies to form a plurality of captured analytes (e.g., to transform the analytes present in the cellular extract into complexes of captured analytes comprising the analytes and capture antibodies);
(ii) incubating (e.g., contacting) the plurality of captured analytes with activation state-dependent antibodies specific for the corresponding analytes to form a plurality of detectable captured analytes (e.g., to transform the complexes of captured analytes into complexes of detectable captured analytes comprising the captured analytes and activation state-dependent antibodies);
(iii) incubating (e.g., contacting) the plurality of detectable captured analytes with first and second members of a signal amplification pair to generate an amplified signal; and
(iv) detecting the amplified signal generated from the first and second members of the signal amplification pair.

In some instances, the activation state-dependent antibodies comprise a first member of a binding pair (e.g., biotin). In other instances, the first member of the signal amplification pair (e.g., a peroxidase such as HRP) comprises a second member of the binding pair (e.g., streptavidin). In certain instances, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain other embodiments, the assay in step (c) comprises:
(i) incubating (e.g., contacting) the cellular extract with the plurality of dilution series of capture antibodies to form a plurality of captured analytes (e.g., to transform the analytes present in the cellular extract into complexes of captured analytes comprising the analytes and capture antibodies);
(ii) incubating (e.g., contacting) the plurality of captured analytes with detection antibodies comprising a plurality of activation state-independent antibodies and a plurality of activation state-dependent antibodies specific for the corresponding analytes to form a plurality of detectable captured analytes (e.g., to transform the complexes of captured analytes into complexes of detectable captured analytes comprising the captured analytes and detection antibodies),
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(iii) incubating (e.g., contacting) the plurality of detectable captured analytes with a second member of the signal amplification pair to generate an amplified signal; and
(iv) detecting the amplified signal generated from the first and second members of the signal amplification pair.

The activation state-independent antibodies may be directly labeled with the facilitating moiety or indirectly labeled with the facilitating moiety, e.g., via hybridization between an oligonucleotide conjugated to the activation state-independent antibodies and a complementary oligonucleotide conjugated to the facilitating moiety. Similarly, the activation state-dependent antibodies may be directly labeled with the first member of the signal amplification pair or indirectly labeled with the first member of the signal amplification pair, e.g., via binding between a first member of a binding pair conjugated to the activation state-dependent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the activation state-independent antibodies can be conjugated to a sulfhydryl-activated dextran molecule as described in, e.g., Examples 16 and 17. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the activation state-dependent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

In some embodiments, the methods of the present invention may be useful to aid or assist in the selection of a suitable anticancer drug for the treatment of a breast tumor. In other embodiments, the methods of the present invention may be useful for improving the selection of a suitable anticancer drug for the treatment of a breast tumor.

In another aspect, the present invention provides a method for identifying the response of a breast tumor to treatment with an anticancer drug, the method comprising:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) identifying the breast tumor as responsive or non-responsive to treatment with the anticancer drug by comparing the activation state detected for the one or more analytes with a reference activation profile generated in the absence of the anticancer drug.

In certain instances, the methods of the present invention may further comprise sending or reporting the results of step (d) to a clinician, e.g., an oncologist or a general practitioner. In certain other instances, the methods of the present invention may further comprise recording or storing the results of step (d) in a computer database or other suitable machine or device for storing information, e.g., at a laboratory.

In a preferred embodiment, the method for identifying the response of a breast tumor to treatment with an anticancer drug comprises:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support;
(d) comparing the activation state detected for the one or more analytes with a reference activation profile generated in the absence of the anticancer drug; and
(e) indicating that the breast tumor is responsive to treatment with the anticancer drug when the activation state detected for the one or more analytes is substantially decreased compared to the reference activation profile.

In certain instances, the preferred embodiment may further comprise, i.e., as step (f), or alternatively comprise, i.e., as step (e), the step of indicating that the breast tumor is non-responsive to treatment with the anticancer drug when the activation state detected for the one or more analytes is not substantially decreased compared to the reference activation profile.

In certain other instances, the preferred embodiment may further comprise sending or reporting the results of step (e) to a clinician, e.g., an oncologist or a general practitioner. In yet other instances, the preferred embodiment may further comprise recording or storing the results of step (e) in a computer database or other suitable machine or device for storing information, e.g., at a laboratory.

The activation state of an analyte (e.g., a signal transduction molecule) may be "substantially decreased" in the presence of an anticancer drug as described above. In some embodiments, the methods described herein may further comprise the step of obtaining a sample from a subject having a breast tumor from which breast cancer cells are isolated. The sample may be obtained from a breast cancer subject either before anticancer drug treatment (e.g., prior to incubation with an anticancer drug) or after administration of an anticancer drug (e.g., at any time throughout the course of cancer treatment). Suitable samples include, but are not limited to, whole blood, serum, plasma, ductal lavage fluid, nipple aspirate, lymph, bone marrow aspirate, urine, saliva, fine needle aspirate (FNA), and combinations thereof. In one preferred embodiment, the sample is a whole blood or FNA sample. In this embodiment, circulating cells of a breast tumor may be isolated from the whole blood sample or breast cancer cells may be isolated from the FNA sample. If isolated cells are obtained from a subject who has not received treatment with an anticancer drug, the isolated cells may be incubated in vitro under suitable conditions with one or a cocktail of anticancer drugs which target one or more of the analytes to be detected in step (c).

Circulating cells of a breast tumor may be isolated from a sample by any technique known in the art, e.g., by immunomagnetic separation, the CellTracks° System, microfluidic separation, FACS, density gradient centrifugation, and depletion methods (see, Example 1). Examples of circulating cells that may be isolated from a sample include, without limitation, circulating tumor cells, circulating endothelial cells, circulating endothelial progenitor cells, cancer stem cells, disseminated tumor cells, and combinations thereof. Isolated cells such as circulating cells may be lysed to thereby transform the isolated cells into a cellular extract by any technique known in the art (see, Example 1).

In some embodiments, the breast tumor is derived from a subject with ductal carcinoma or lobular carcinoma. Examples of ductal carcinomas include, but are not limited to, invasive ductal carcinoma and ductal carcinoma in situ. Non-limiting examples of lobular carcinomas include invasive lobular carcinoma or lobular carcinoma in situ.

In certain instances, the cells of a breast tumor are isolated from tumor tissue. The tumor tissue may be, e.g., primary tumor tissue or metastatic tumor tissue. In a preferred embodiment, the cells are isolated from tumor tissue as a fine needle aspirate (FNA) sample.

In some embodiments, the isolated cells are stimulated in vitro with growth factors as described herein. In other embodiments, the anticancer drug may comprise one or more of the therapeutic agents described herein, including but not limited to monoclonal antibodies, tyrosine kinase inhibitors, chemotherapeutic agents, hormonal therapeutic agents, radiotherapeutic agents, and vaccines.

In preferred embodiments, the one or more analytes present in the cellular extract comprise a plurality of signal transduction molecules. Examples of signal transduction molecules include, without limitation, receptor tyrosine kinases, non-receptor tyrosine kinases, tyrosine kinase signaling cascade components, nuclear hormone receptors, nuclear receptor coactivators, nuclear receptor repressors, and combinations thereof. In certain instances, the plurality of signal transduction molecules is selected from the group consisting of EGFR (ErbB1), HER-2 (ErbB2), p95ErbB2, HER-3 (ErbB3), HER-4 (ErbB4), Raf, SRC, Mek, NFkB-IkB, mTor, PI3K, VEGF, VEGFR-1, VEGFR-2, VEGFR-3, Eph-a, Eph-b, Eph-c, Eph-d, cMet, FGFR, cKit, Flt-3, Tie-1, Tie-2, Flt-3, cFMS, PDGFRA, PDGFRB, Abl, FTL 3, RET, Kit, HGFR, FGFR1, FGFR2, FGFR3, FGFR4, IGF-1R, ER, PR, NCOR, AIB1, and combinations thereof. Preferably, the plurality of signal transduction molecules is selected from the group consisting of ErbB1, ErbB2, p95ErbB2, ErbB3, ErbB4, VEGFR-1, VEGFR-2, VEGFR-3, ER, PR, and combinations thereof.

In some embodiments, the activation state detected for the one or more analytes present in the cellular extract may be, e.g., a phosphorylation state, a ubiquitination state, a complexation state, or combinations thereof. In other embodiments, the solid support may comprise, e.g., glass, plastic, chips, pins, filters, beads, paper, membrane, fiber bundles, and combinations thereof. In yet other embodiments, the capture antibodies are restrained on the solid support in an addressable array.

In certain embodiments, the assay in step (c) comprises:
(i) incubating (e.g., contacting) the cellular extract with the plurality of dilution series of capture antibodies to form a plurality of captured analytes (e.g., to transform the analytes present in the cellular extract into complexes of captured analytes comprising the analytes and capture antibodies);
(ii) incubating (e.g., contacting) the plurality of captured analytes with activation state-dependent antibodies specific for the corresponding analytes to form a plurality of detectable captured analytes (e.g., to transform the complexes of captured analytes into complexes of detectable captured analytes comprising the captured analytes and activation state-dependent antibodies);
(iii) incubating (e.g., contacting) the plurality of detectable captured analytes with first and second members of a signal amplification pair to generate an amplified signal; and
(iv) detecting the amplified signal generated from the first and second members of the signal amplification pair.

In some instances, the activation state-dependent antibodies comprise a first member of a binding pair (e.g., biotin). In other instances, the first member of the signal amplification pair (e.g., a peroxidase such as HRP) comprises a second member of the binding pair (e.g., streptavidin). In certain instances, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain other embodiments, the assay in step (c) comprises:
(i) incubating (e.g., contacting) the cellular extract with the plurality of dilution series of capture antibodies to form a plurality of captured analytes (e.g., to transform the analytes present in the cellular extract into complexes of captured analytes comprising the analytes and capture antibodies);
(ii) incubating (e.g., contacting) the plurality of captured analytes with detection antibodies comprising a plurality of activation state-independent antibodies and a plurality of activation state-dependent antibodies specific for the corresponding analytes to form a plurality of detectable captured analytes (e.g., to transform the complexes of captured analytes into complexes of detectable captured analytes comprising the captured analytes and detection antibodies),
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(iii) incubating (e.g., contacting) the plurality of detectable captured analytes with a second member of the signal amplification pair to generate an amplified signal; and
(iv) detecting the amplified signal generated from the first and second members of the signal amplification pair.

The activation state-independent antibodies may be directly labeled with the facilitating moiety or indirectly labeled with the facilitating moiety, e.g., via hybridization between an oligonucleotide conjugated to the activation state-independent antibodies and a complementary oligonucleotide conjugated to the facilitating moiety. Similarly, the activation state-dependent antibodies may be directly labeled with the first member of the signal amplification pair or indirectly labeled with the first member of the signal amplification pair, e.g., via binding between a first member of a binding pair conjugated to the activation state-dependent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the activation state-independent antibodies can be conjugated to a sulfhydryl-activated dextran molecule as described in, e.g., Examples 16 and 17. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the activation state-dependent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

In some embodiments, the methods of the present invention may be useful to aid or assist in the identification of a breast tumor's response to treatment with an anticancer drug. In other embodiments, the methods of the present invention may be useful for improving the identification of a breast tumor's response to treatment with an anticancer drug.

In yet another aspect, the present invention provides a method for predicting the response of a subject having a breast tumor to treatment with an anticancer drug, the method comprising:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support; and
(d) predicting the likelihood that the subject will respond to treatment with the anticancer drug by comparing the activation state detected for the one or more analytes with a reference activation profile generated in the absence of the anticancer drug.

In certain instances, the methods of the present invention may further comprise sending or reporting the results of step (d) to a clinician, e.g., an oncologist or a general practitioner.

In certain other instances, the methods of the present invention may further comprise recording or storing the results of step (d) in a computer database or other suitable machine or device for storing information, e.g., at a laboratory.

In a preferred embodiment, the method for predicting the response of a subject having a breast tumor to treatment with an anticancer drug comprises:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support;
(d) comparing the activation state detected for the one or more analytes with a reference activation profile generated in the absence of the anticancer drug; and
(e) indicating that the subject will likely respond to treatment with the anticancer drug when the activation state detected for the one or more analytes is substantially decreased compared to the reference activation profile.

In certain instances, the preferred embodiment may further comprise, i.e., as step (f), or alternatively comprise, i.e., as step (e), the step of indicating that the subject will not likely respond (e.g., have an unlikely chance or low probability of responding) to treatment with the anticancer drug when the activation state detected for the one or more analytes is not substantially decreased compared to the reference activation profile.

In certain other instances, the preferred embodiment may further comprise sending or reporting the results of step (e) to a clinician, e.g., an oncologist or a general practitioner. In yet other instances, the preferred embodiment may further comprise recording or storing the results of step (e) in a computer database or other suitable machine or device for storing information, e.g., at a laboratory.

The activation state of an analyte (e.g., a signal transduction molecule) may be "substantially decreased" in the presence of an anticancer drug as described above. In some embodiments, the methods described herein may further comprise the step of obtaining a sample from a subject having a breast tumor from which breast cancer cells are isolated. The sample may be obtained from a breast cancer subject either before anticancer drug treatment (e.g., prior to incubation with an anticancer drug) or after administration of an anticancer drug (e.g., at any time throughout the course of cancer treatment). Suitable samples include, but are not limited to, whole blood, serum, plasma, ductal lavage fluid, nipple aspirate, lymph, bone marrow aspirate, urine, saliva, fine needle aspirate (FNA), and combinations thereof. In one preferred embodiment, the sample is a whole blood or FNA sample. In this embodiment, circulating cells of a breast tumor may be isolated from the whole blood sample or breast cancer cells may be isolated from the FNA sample. If isolated cells are obtained from a subject who has not received treatment with an anticancer drug, the isolated cells may be incubated in vitro under suitable conditions with one or a cocktail of anticancer drugs which target one or more of the analytes to be detected in step (c).

Circulating cells of a breast tumor may be isolated from a sample by any technique known in the art, e.g., by immunomagnetic separation, the CellTracks® System, microfluidic separation, FACS, density gradient centrifugation, and depletion methods (see, Example 1). Examples of circulating cells that may be isolated from a sample include, without limitation, circulating tumor cells, circulating endothelial cells, circulating endothelial progenitor cells, cancer stem cells, disseminated tumor cells, and combinations thereof. Isolated cells such as circulating cells may be lysed to thereby transform the isolated cells into a cellular extract by any technique known in the art (see, Example 1).

In some embodiments, the breast tumor is derived from a subject with ductal carcinoma or lobular carcinoma. Examples of ductal carcinomas include, but are not limited to, invasive ductal carcinoma and ductal carcinoma in situ. Non-limiting examples of lobular carcinomas include invasive lobular carcinoma or lobular carcinoma in situ.

In certain instances, the cells of a breast tumor are isolated from tumor tissue. The tumor tissue may be, e.g., primary tumor tissue or metastatic tumor tissue. In a preferred embodiment, the cells are isolated from tumor tissue as a fine needle aspirate (FNA) sample.

In some embodiments, the isolated cells are stimulated in vitro with growth factors as described herein. In other embodiments, the anticancer drug may comprise one or more of the therapeutic agents described herein, including but not limited to monoclonal antibodies, tyrosine kinase inhibitors, chemotherapeutic agents, hormonal therapeutic agents, radiotherapeutic agents, and vaccines.

In preferred embodiments, the one or more analytes present in the cellular extract comprise a plurality of signal transduction molecules. Examples of signal transduction molecules include, without limitation, receptor tyrosine kinases, non-receptor tyrosine kinases, tyrosine kinase signaling cascade components, nuclear hormone receptors, nuclear receptor coactivators, nuclear receptor repressors, and combinations thereof. In certain instances, the plurality of signal transduction molecules is selected from the group consisting of EGFR (ErbB1), HER-2 (ErbB2), p95ErbB2, HER-3 (ErbB3), HER-4 (ErbB4), Raf, SRC, Mek, NFkB-IkB, mTor, PI3K, VEGF, VEGFR-1, VEGFR-2, VEGFR-3, Eph-a, Eph-b, Eph-c, Eph-d, cMet, FGFR, cKit, Flt-3, Tie-1, Tie-2, Flt-3, cFMS, PDGFRA, PDGFRB, Abl, FTL 3, RET, Kit, HGFR, FGFR1, FGFR2, FGFR3, FGFR4, IGF-1R, ER, PR, NCOR, AIB1, and combinations thereof. Preferably, the plurality of signal transduction molecules is selected from the group consisting of ErbB1, ErbB2, p95ErbB2, ErbB3, ErbB4, VEGFR-1, VEGFR-2, VEGFR-3, ER, PR, and combinations thereof.

In some embodiments, the activation state detected for the one or more analytes present in the cellular extract may be, e.g., a phosphorylation state, a ubiquitination state, a complexation state, or combinations thereof. In other embodiments, the solid support may comprise, e.g., glass, plastic, chips, pins, filters, beads, paper, membrane, fiber bundles, and combinations thereof. In yet other embodiments, the capture antibodies are restrained on the solid support in an addressable array.

In certain embodiments, the assay in step (c) comprises:
(i) incubating (e.g., contacting) the cellular extract with the plurality of dilution series of capture antibodies to form a plurality of captured analytes (e.g., to transform the analytes present in the cellular extract into complexes of captured analytes comprising the analytes and capture antibodies);
(ii) incubating (e.g., contacting) the plurality of captured analytes with activation state-dependent antibodies specific for the corresponding analytes to form a plurality of detectable captured analytes (e.g., to transform the complexes of captured analytes into complexes of detectable captured analytes comprising the captured analytes and activation state-dependent antibodies);
(iii) incubating (e.g., contacting) the plurality of detectable captured analytes with first and second members of a signal amplification pair to generate an amplified signal; and
(iv) detecting the amplified signal generated from the first and second members of the signal amplification pair.

In some instances, the activation state-dependent antibodies comprise a first member of a binding pair (e.g., biotin). In other instances, the first member of the signal amplification pair (e.g., a peroxidase such as HRP) comprises a second member of the binding pair (e.g., streptavidin). In certain instances, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain other embodiments, the assay in step (c) comprises:
(i) incubating (e.g., contacting) the cellular extract with the plurality of dilution series of capture antibodies to form a plurality of captured analytes (e.g., to transform the analytes present in the cellular extract into complexes of captured analytes comprising the analytes and capture antibodies);
(ii) incubating (e.g., contacting) the plurality of captured analytes with detection antibodies comprising a plurality of activation state-independent antibodies and a plurality of activation state-dependent antibodies specific for the corresponding analytes to form a plurality of detectable captured analytes (e.g., to transform the complexes of captured analytes into complexes of detectable captured analytes comprising the captured analytes and detection antibodies),
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(iii) incubating (e.g., contacting) the plurality of detectable captured analytes with a second member of the signal amplification pair to generate an amplified signal; and
(iv) detecting the amplified signal generated from the first and second members of the signal amplification pair.

The activation state-independent antibodies may be directly labeled with the facilitating moiety or indirectly labeled with the facilitating moiety, e.g., via hybridization between an oligonucleotide conjugated to the activation state-independent antibodies and a complementary oligonucleotide conjugated to the facilitating moiety. Similarly, the activation state-dependent antibodies may be directly labeled with the first member of the signal amplification pair or indirectly labeled with the first member of the signal amplification pair, e.g., via binding between a first member of a binding pair conjugated to the activation state-dependent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the activation state-independent antibodies can be conjugated to a sulfhydryl-activated dextran molecule as described in, e.g., Examples 16 and 17. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the activation state-dependent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

In some embodiments, the methods of the present invention may be useful to aid or assist in the prediction of a subject's likelihood of responding to treatment with an anticancer drug. In other embodiments, the methods of the present invention may be useful for improving the prediction of a subject's likelihood of responding to treatment with an anticancer drug.

In a further aspect, the present invention provides an array having superior dynamic range comprising a plurality of dilution series of capture antibodies restrained on a solid support, wherein the capture antibodies in each dilution series are specific for one or more analytes corresponding to a component of a signal transduction pathway or other protein (e.g., nuclear hormone receptor) in a cellular extract.

In certain embodiments, the signal transduction pathway may be involved in cell proliferation. In such embodiments, the capture antibodies may comprise, for example, one or more members selected from the group consisting of antibodies reactive with IGF1R, cMET, ErbB1, ErbB2, p95ErbB2, ErbB3, ErbB4, Shc, PI3K, Erk, Rsk, Akt, p70S6K, ER, PR, NCOR, and AIB1. In certain other embodiments, the signal transduction pathway may be involved in tumor angiogenesis. In such embodiments, the capture antibodies may comprise, for example, one or more members selected from the group consisting of antibodies reactive with Shc, PI3K, Erk, Rsk, Akt, p70S6K, VEGFR-1, VEGFR-2, Tie 2, V-Cadherin-R2 complex, PDGFRA, and PDGFRB. As such, the addressable arrays described herein are particularly useful for determining the expression and/or activation state of signal transduction molecules and other proteins involved in breast cancer.

In an additional aspect, the present invention provides a method for detecting the presence (or absence) of a truncated receptor, the method comprising:
(a) incubating (e.g., contacting) a cellular extract with a plurality of beads specific for an extracellular domain (ECD) binding region of a full-length receptor;
(b) removing the plurality of beads from the cellular extract, thereby removing the full-length receptor to form a cellular extract devoid of the full-length receptor (e.g., to transform the cellular extract into a cellular extract devoid of a specific full-length receptor or family of full-length receptors);
(c) incubating (e.g., contacting) the cellular extract devoid of the full-length receptor with a plurality of capture antibodies, wherein the plurality of capture antibodies is specific for an intracellular domain (ICD) binding region of a truncated receptor and wherein the plurality of capture antibodies is restrained on a solid support to form a plurality of captured truncated receptors (e.g., to transform the truncated receptor present in a full-length receptor-depleted cellular extract into complexes of truncated receptors and capture antibodies);
(d) incubating (e.g., contacting) the plurality of captured truncated receptors with detection antibodies specific for the corresponding truncated receptors to form a plurality of detectable captured truncated receptors (e.g., to transform the complexes of captured truncated receptors into complexes of detectable captured truncated receptors comprising the captured truncated receptors and activation state-dependent antibodies);
(e) incubating (e.g., contacting) the plurality of detectable captured truncated receptors with first and second members of a signal amplification pair to generate an amplified signal; and
(f) detecting an amplified signal generated from the first and second members of the signal amplification pair.

The truncated receptor is typically a fragment of the full-length receptor and shares an an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated receptor with a shortened ECD or a truncated receptor comprising a membrane-associated or cytosolic ICD fragment.

In certain preferred embodiments, the truncated receptor is p95ErbB2 and the corresponding full-length receptor is ErbB2 (HER-2). However, one skilled in the art will appreciate that the methods described herein for detecting truncated proteins can be applied to a number of different proteins including, but not limited to, the EGFR V111 mutant (implicated in glioblastoma, colorectal cancer, etc.), other truncated receptor tyrosine kinases, caspases, and the like. Example 12 provides an exemplary embodiment of the assay methods of the present invention for detecting truncated receptors such as p95ErbB2 in rare circulating cells using a multiplex, high-throughput, single detection microarray ELISA having superior dynamic range.

In some embodiments, the plurality of beads specific for an ECD binding region comprises a streptavidin-biotin pair, wherein the streptavidin is attached to the bead and the biotin is attached to an antibody. In certain instances, the antibody is specific for the ECD binding region of the full-length receptor. In other embodiments, the cellular extract is produced by lysing circulating cells of a solid tumor such as, for example, a breast tumor. The circulating cells may be isolated from a sample by any technique described herein, e.g., by immunomagnetic separation. Suitable samples include, but are not limited to, whole blood, serum, plasma, ductal lavage fluid, nipple aspirate, lymph, bone marrow aspirate, urine, saliva, fine needle aspirate, and combinations thereof. In a preferred embodiment, the sample is whole blood. Alternatively, the cellular extract is produced by lysing cells isolated from tumor tissue such as, for example, breast tumor tissue. The tumor tissue may be, e.g., primary tumor tissue or metastatic tumor tissue. In a preferred embodiment, the cells are isolated from tumor tissue as a fine needle aspirate (FNA) sample.

In some embodiments, the isolated cells are stimulated in vitro with growth factors as described herein. In other embodiments, the isolated cells are incubated with an anti-cancer drug prior to growth factor stimulation. Suitable anti-cancer drugs include one or more of the therapeutic agents described herein, such as, for example, monoclonal antibodies, tyrosine kinase inhibitors, chemotherapeutic agents, hormonal therapeutic agents, radiotherapeutic agents, and vaccines.

In certain embodiments, an activation state of the plurality of detectable captured truncated receptors is interrogated. The activation state to be interrogated may be, e.g., a phosphorylation state, a ubiquitination state, a complexation state, or combinations thereof. In certain other embodiments, the solid support to which the plurality of captured antibodies is restrained may comprise, e.g., glass, plastic, chips, pins, filters, beads, paper, membrane, fiber bundles, and combinations thereof. In further embodiments, the plurality of capture antibodies is restrained on the solid support in an addressable array.

In some instances, the detection antibodies comprise a first member of a binding pair (e.g., biotin). In other instances, the first member of the signal amplification pair (e.g., a peroxidase such as HRP) comprises a second member of the binding pair (e.g., streptavidin). In certain instances, the second member of the signal amplification pair may be, for example, a tyramide reagent (e.g., biotin-tyramide). Preferably, the amplified signal is generated by peroxidase oxidation of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In a related aspect, the present invention provides a method for detecting the presence (or absence) of a truncated receptor, the method comprising:
(a) incubating (e.g., contacting) a cellular extract with a plurality of beads specific for an extracellular domain (ECD) binding region of a full-length receptor;
(b) removing the plurality of beads from the cellular extract, thereby removing the full-length receptor to form a cellular extract devoid of the full-length receptor (e.g., to transform the cellular extract into a cellular extract devoid of a specific full-length receptor or family of full-length receptors);
(c) incubating (e.g., contacting) the cellular extract devoid of the full-length receptor with a plurality of capture antibodies, wherein the plurality of capture antibodies is specific for an intracellular domain (ICD) binding region of the truncated receptor and wherein the plurality of capture antibodies is restrained on a solid support to form a plurality of captured truncated receptors (e.g., to transform the truncated receptor present in a full-length receptor-depleted cellular extract into complexes of truncated receptors and capture antibodies);
(d) incubating (e.g., contacting) the plurality of captured truncated receptors with detection antibodies comprising a plurality of activation state-independent antibodies and a plurality of activation state-dependent antibodies specific for the corresponding truncated receptors to form a plurality of detectable captured truncated receptors (e.g., to transform the complexes of captured truncated receptors into complexes of detectable captured truncated receptors comprising the captured truncated receptors and detection antibodies),
wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
(e) incubating (e.g., contacting) the plurality of detectable captured truncated receptors with a second member of the signal amplification pair to generate an amplified signal; and
(f) detecting the amplified signal generated from the first and second members of the signal amplification pair.

The truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated receptor with a shortened ECD or a truncated receptor comprising a membrane-associated or cytosolic ICD fragment.

In certain preferred embodiments, the truncated receptor is p95ErbB2 and the corresponding full-length receptor is ErbB2 (HER-2). However, one skilled in the art will appreciate that the methods described herein for detecting truncated proteins can be applied to a number of different proteins including, but not limited to, the EGFR VIII mutant (implicated in glioblastoma, colorectal cancer, etc.), other truncated receptor tyrosine kinases, caspases, and the like. Example 12 provides an exemplary embodiment of the assay methods of the present invention for detecting truncated receptors such as p95ErbB2 in rare circulating cells using a multiplex, high-throughput, proximity dual detection microarray ELISA having superior dynamic range.

In some embodiments, the plurality of beads specific for an ECD binding region comprises a streptavidin-biotin pair, wherein the streptavidin is attached to the bead and the biotin is attached to an antibody. In certain instances, the antibody is specific for the ECD binding region of the full-length receptor. In other embodiments, the cellular extract is produced by lysing circulating cells of a solid tumor such as, for example, a breast tumor. The circulating cells may be isolated from a sample by any technique described herein, e.g., by immunomagnetic separation. Suitable samples include, but are not limited to, whole blood, serum, plasma, ductal lavage fluid, nipple aspirate, lymph, bone marrow aspirate, urine, saliva, fine needle aspirate, and combinations thereof. In a preferred embodiment, the sample is whole blood. Alternatively, the cellular extract is produced by lysing cells isolated from tumor tissue such as, for example, breast tumor tissue. The tumor tissue may be, e.g., primary tumor tissue or metastatic tumor tissue. In a preferred embodiment, the cells are isolated from tumor tissue as a fine needle aspirate (FNA) sample.

In some embodiments, the isolated cells are stimulated in vitro with growth factors as described herein. In other embodiments, the isolated cells are incubated with an anticancer drug prior to growth factor stimulation. Suitable anticancer drugs include one or more of the therapeutic agents described herein, such as, for example, monoclonal antibodies, tyrosine kinase inhibitors, chemotherapeutic agents, hormonal therapeutic agents, radiotherapeutic agents, and vaccines.

In certain embodiments, an activation state of the plurality of detectable captured truncated receptors is interrogated. The activation state to be interrogated may be, e.g., a phosphorylation state, a ubiquitination state, a complexation state, or combinations thereof. In certain other embodiments, the solid support to which the plurality of captured antibodies is restrained may comprise, e.g., glass, plastic, chips, pins, filters, beads, paper, membrane, fiber bundles, and combinations thereof. In further embodiments, the plurality of capture antibodies is restrained on the solid support in an addressable array.

The activation state-independent antibodies may be directly labeled with the facilitating moiety or indirectly labeled with the facilitating moiety, e.g., via hybridization between an oligonucleotide conjugated to the activation state-independent antibodies and a complementary oligonucleotide conjugated to the facilitating moiety. Similarly, the activation state-dependent antibodies may be directly labeled with the first member of the signal amplification pair or indirectly labeled with the first member of the signal amplification pair, e.g., via binding between a first member of a binding pair conjugated to the activation state-dependent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the activation state-independent antibodies can be conjugated to a sulfhydryl-activated dextran molecule as described in, e.g., Examples 16 and 17. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the activation state-dependent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

In some embodiments, the assay methods of the present invention for detecting the presence (or absence or level) of a truncated receptor such as p95ErbB2 may be useful to aid or assist in cancer diagnosis, prognosis, or in the design of cancer treatments, e.g., by aiding or assisting in (i) the selection of a suitable anticancer drug for the treatment of a breast tumor, (ii) the identification of a breast tumor's response to treatment with an anticancer drug, or (iii) the prediction of a subject's likelihood of responding to treatment with an anticancer drug.

In other embodiments, the assay methods of the present invention for detecting the presence (or absence or level) of a truncated receptor such as p95ErbB2 may be useful for improving cancer diagnosis, prognosis, or the design of cancer treatments, e.g., by improving (i) the selection of a suitable anticancer drug for the treatment of a breast tumor, (ii) the identification of a breast tumor's response to treatment with an anticancer drug, or (iii) the prediction of a subject's likelihood of responding to treatment with an anticancer drug.

IV. Breast Cancer

Breast cancer is the fifth most common cause of cancer death worldwide, after lung cancer, stomach cancer, liver cancer, and colon cancer. In 2005, breast cancer caused 502,000 deaths worldwide. Among women worldwide, breast cancer is the most common cause of cancer death.

In the United States, breast cancer is the third most common cause of cancer death, after lung cancer and colon cancer. In 2007, breast cancer caused over 40,000 deaths in the U.S. Among women in the U.S., breast cancer is the most common cancer and the second-most common cause of cancer death. In fact, women in the U.S. have a 1 in 8 lifetime chance of developing invasive breast cancer and a 1 in 33 chance of breast cancer causing their death.

The number of cases of breast cancer worldwide has significantly increased since the 1970s, a phenomenon partly blamed on modern lifestyles in the Western world. Because the breast is composed of identical tissues in males and females, breast cancer also occurs in males, though it is less common.

Classification

Breast cancers can be described using four different classification schemes, each based on the following criteria:
1. Pathology. The pathologist can categorize each tumor based on its histological appearance and other criteria. The most common pathologic types of breast cancer are invasive ductal carcinoma and invasive lobular carcinoma.
2. Grade of tumor. The histological grade can be determined by the pathologist under a microscope. A well-differentiated (low grade) tumor resembles normal tissue. A poorly differentiated (high grade) tumor is composed of disorganized cells and does not look like normal tissue. Moderately differentiated (intermediate grade) tumors are somewhere in between.
3. Protein and gene expression status. Breast cancers can be tested for expression and/or activation of signal transduction molecules such as, for example, the estrogen receptor (ER), progesterone receptor (PR), and Her2/Neu/ErbB2. As described herein, the profile of expression of a given tumor aids in the prediction of its prognosis and assists the oncologist in selecting the most appropriate treatment.
4. Stage of the tumor. Breast cancers can be staged according to the TNM classification system:
   a. Tumor. Five values (Tis, T1, T2, T3, or T4) depending on the presence or absence of invasive cancer, the dimensions of the invasive cancer, and the presence or absence of invasion outside of the breast (e.g., to the skin of the breast or to the muscle or ribcage underneath).
   b. Lymph Node. Four values (N0, N1, N2, or N3) depending on the number, size, and location of metastatic deposits in lymph nodes.
   c. Metastases. Two values (M0 or M1) depending on the presence or absence of metastases other than lymph nodes (so-called distant metastases, e.g., to bone, brain, lung, etc.).

Pathology

With respect to pathology, the World Health Organization's classification of breast tumors sets forth the following histological types:
1. Invasive breast carcinomas such as invasive ductal carcinoma (e.g., basal-like carcinoma, mixed type carcinoma, pleomorphic carcinoma, carcinoma with osteoclastic giant cells, carcinoma with choriocarcinomatous features, carcinoma with melanotic features), invasive lobular carcinoma, tubular carcinoma, invasive cribriform carcinoma, medullary carcinoma, mucinous carcinoma and other tumours with abundant mucin (e.g., mucinous carcinoma, cystadenocarcinoma and columnar cell mucinous carcinoma, signet ring cell carcinoma), neuroendocrine tumours (e.g., solid neuroendocrine carcinoma (carcinoid of the breast), atypical carcinoid tumour, small cell/oat cell carcinoma, large cell neuroendocrine carcinoma), invasive papillary carcinoma, invasive micropapillary carcinoma, apocrine carcinoma, metaplastic carcinomas (e.g., mixed epithelial/mesenchymal metaplastic carcinomas or pure epithelial metaplastic carciomas such as squamous cell carcinoma, adenocarcinoma with spindle cell metaplasia, adenosquamous carcinoma, and mucoepidermoid carcinoma), lipid-rich carcinoma, secretory carcinoma, oncocytic carcinoma, adenoid cystic carcinoma, acinic cell carcinoma, glycogen-rich clear cell carcinoma, sebaceous carcinoma, inflammatory carcinoma, and bilateral breast carcinoma;
2. Precursor lesions such as lobular neoplasia (e.g., lobular carcinoma in situ), intraductal proliferative lesions (e.g., usual ductal hyperplasia, flat epithelial hyperplasia, atypical ductal hyperplasia, ductal carcinoma in situ), microinvasive carcinoma, and intraductal papillary neoplasms (e.g., central papilloma, peripheral papilloma, atypical papilloma, intraductal papillary carcinoma, intracystic papillary carcinoma, benign epithelial lesions);
3. Benign epithelial lesions such as adenosis, including variants (e.g., sclerosing adenosis, apocrine adenosis, blunt duct adenosis, microglandular adenosis, adenomyoepithelial adenosis), radial scar/complex sclerosing lesion, and adenomas (e.g., tubular adenoma, lactating adenoma, apocrine adenoma, pleomorphic adenoma, ductal adenoma);
4. Myoepithelial lesions such as myoepitheliosis, adenomyoepithelial adenosis, adenomyoepithelioma, and malignant myoepithelioma;
5. Mesenchymal tumors such as sarcoma, haemangioma, angiomatosis, haemangiopericytoma, pseudoangiomatous stromal hyperplasia, myofibroblastoma, fibromatosis (agressive), inflammatory myofibroblastic tumour, lipoma (e.g., angiolipoma), granular cell tumor, neurofibroma, schwannoma, angiosarcoma, liposarcoma, rhabdomyosarcoma, osteosarcoma, leiomyoma, and leiomysarcoma;
6. Fibroepithelial tumors such as fibroadenoma, phyllodes tumor (e.g., benign, borderline, malignant), low grade periductal stromal sarcoma, and mammary hamartoma;
7. Tumors of the nipple such as nipple adenoma, syringomatous adenoma, and Paget's disease of the nipple;
8. Malignant lymphoma;
9. Metastatic tumors; and
10. Tumors of the male breast such as gynecomastia and in situ or invasive carcinoma.

Ductal carcinoma is the most common type of breast cancer in women and refers to the development of cancer cells within the milk ducts of the breast. It comes in two forms: Invasive ductal carcinoma (IDC), an invasive, malignant neoplasm; and ductal carcinoma in situ (DCIS), a noninvasive neoplasm. IDC is the most common form of invasive breast cancer. It accounts for about 80% of all types of breast cancer. On a mammography, it is usually visualized as a mass with fine spikes radiating from the edges. On physical examination, this lump usually feels much harder or firmer than benign breast lesions. On microscopic examination, the cancerous cells invade and replace the surrounding normal tissues. DCIS is the most common type of noninvasive breast cancer in women. As screening mammography has become more widespread, DCIS has become one of the most commonly diagnosed breast conditions. It is often referred to as "stage zero" breast cancer. DCIS is usually discovered through a mammogram as very small specks of calcium known as microcalcifications. However, not all microcalcifications indicate the presence of DCIS, which must be confirmed by biopsy. DCIS may be multifocal, and treatment is aimed at excising all of the abnormal duct elements, leaving clear margins. After excision treatment often includes local radiation therapy. With appropriate treatment, DCIS is unlikely to develop into invasive cancer. Surgical excision with radiation lowers the risk that the DCIS will recur or that invasive breast cancer will develop.

Invasive lobular carcinoma (ILC) is a type of breast cancer that starts in a lobule and spreads to surrounding breast tissue. If not treated at an earlystage, ILC can move into other parts of the body, such as the uterus or ovaries. ILC is the second most common type of invasive breast cancer, accounting for about 10-15% of all breast cancer cases. ILC is characterized by a general thickening of an area of the breast, usually the section above the nipple and toward the arm. ILC is less likely to appear on a mammogram. When it does appear, it may show as a mass with fine spikes radiating from the edges or appear as an asymmetry compared to the other breast.

Therapies

A number of alterations in key signal transduction components have been demonstrated in breast cancer. These include: EGFR mutations that result in activation; activation of other receptor tyrosine kinases such as cMet; EGFR activation with HER-2 and HER-3 activation or HER-2 amplfcation; EGFR activation with PI3K mutation; EGFR activation with PTEN deletion; and EGFR activation with Ras mutation. Various alterations in different components of signal transduction pathways have been targeted by various forms of chemotherapy.

At the same time, the formation of new blood vessels to tumor cells, a process termed angiogenesis, can be targeted. VEGF is an endothelial cell survival factor which is essential for formation of new blood vessels. Accordingly, one approach to the modulation of VEGF-mediated angiogenesis is to use antibodies directed against the VEGF protein itself or VEGFR. Bevacizumab, a recombinant humanized monoclonal antibody to VEGF, acts synergistically with chemotherapy and has been shown to improve survival in patients with colorectal, breast, and lung cancers.

All endocrine therapies are designed to block estrogen receptor (ER) function in a unique way. For example, selective estrogen receptor modulators (SERMs) such as tamoxifen bind ER and partially block its activity. Ovarian ablation, luteinizing hormone-releasing hormone agonists, and aromatase inhibitors such as anastrozole (Arimidex®), letrozole (Femara®), and exemestane (Aromasin®) reduce the level of estrogen and inhibit ligand-induced activation of ER. The ideal SERM should function as an anti-estrogen in the breast and uterus and a partial estrogen agonist in the skeletal, cardiovascular, and central nervous systems, as well as the gastrointestinal tract and vagina.

Steroidal anti-estrogens such as fulvestrant bind ER more tightly, hence completely blocking its function and inducing receptor degradation.

Tamoxifen, a selective estrogen receptor (ER) modulator, is the most widely used drug for the treatment of ER-positive breast cancer. Adjuvant therapy studies of tamoxifen show a 40% to 50% reduction in the odds of recurrence and mortality. Tamoxifen also provides temporary remission in 30% to 50% of patients with metastatic disease, and it is also effective in the prevention of breast cancer.

Aromatase inhibitors are becoming the standard of care in the treatment of postmenopausal women with breast cancer, while tamoxifen remains the standard in premenopausal women. Although aromatase inhibitors may be slightly more effective than tamoxifen, it remains an important drug because of its documented benefits in sequence with these agents for adjuvant therapy, and because it will continue to have a role in metastatic disease.

Resistance

De novo (no response to initial therapy; primary resistance) and acquired resistance (disease relapse or progression after showing an initial response to therapy; secondary resistance) to tamoxifen are major problems. As a result, understanding tumor biology and the mechanisms of resistance may provide significant clinical implications.

ER/PR biology: ER and PR are nuclear hormone receptors which function as transcription factors in the nucleus when they are bound to ligand(s). ER and PR have similar structures and contain a DNA binding domain, a dimerization domain, a hormone binding domain, and several transcription activating domains. A greater reduction in risk for recurrence was noted for patients with ER positive, PR positive tumors compared with those with ER positive, PR negative tumors.

ER function: Hormone binding to ER activates the protein through phosphorylation, dissociates chaperone proteins such as heat-shock protein 90, and alters its conformation. Hormone bound ("activated") ER then dimerizes with another receptor, and the dimer binds to estrogen response elements (specific DNA sequences) present in the promoter of estrogen-responsive genes. Promoter-bound ER dimers form a complex with co-regulatory proteins such as amplified in breast cancer 1 (AIB1 or SRC3) that coordinately act to influence the transcription of estrogen responsive genes. Typically, co-activators bind ER when the receptor is bound by estrogen, while co-repressors bind when ER is bound by tamoxifen. AIB1 is over-expressed in 65% of breast cancers and the corresponding gene is amplified in 5%. High levels of AIB1 may contribute to SERM resistance by enhancing estrogen agonist activity (e.g., treat with aromatase inhibitors). ER dimers also form complexes with co-repressor proteins such as NCOR to downregulate gene expression of certain genes (e.g., HOXB13).

Several kinases in the growth factor signaling networks can also activate ER in a process termed ligand-independent activation. Under certain conditions such as high ErbB family activity (e.g., high HER-2 or HER-1 activity), ER bound to tamoxifen complexes with AIB1, resulting in increased estrogen agonist activity of tamoxifen (e.g., treat with fulvestrant or aromatase inhibitors along with kinase inhibitors).

This non-nuclear ER action or membrane-initiated steroid signaling (MISS) occurs within minutes of the addition of estrogen. SERMs such as tamoxifen may also activate membrane ER. These receptors have been found in bone, neural, uterine, fat, and endothelial cells. Mechanisms by which estrogen activates membrane ER function are beginning to be clarified. Direct interactions between ER with a variety of membrane-signaling molecules such as the insulin-like growth factor 1 receptor, the p85 regulatory subunit of PI3K, Src, and Shc, a protein which may directly couple ER to a variety of growth factor tyrosine kinase receptors, have been observed. Activation of these pathways by estrogen sends powerful cell survival and cell proliferative signals via activation of Akt and MAPK. In addition, these kinases can phosphorylate ER and its coregulators to augment nuclear ER signaling. Phosphorylation of these proteins can also increase the estrogen agonist-like activity of tamoxifen and other SERMs.

The pure anti-estrogen fulvestrant does not activate membrane ER in this way; however, SERMs such as tamoxifen do activate membrane ER in a manner similar to estrogen. The membrane effects of ER, like its nuclear activity, may be cell, receptor-subtype, and ligand-specific, and it may also be influenced by the growth factor signaling milieu being much more prominent, for instance, in breast cancers overexpressing ErbB1 or HER-2. Stimulation of the MISS activity of ER by tamoxifen and other SERMs may, in part, explain the resistance to these agents sometimes observed in HER-2-overexpressing tumors.

In addition to ER functions associated with the nucleus and plasma membrane (membrane-initiated steroid signaling; MISS), ER conjugates with other pathway molecules to facilitate subsequent tumor progression. This molecular cross-talk can best be treated with aromatase inhibitors and not SERMs.

ER has at least two major functions. It serves as a transcription factor for estrogen-regulated genes and a co-activator for other transcription factors in the nucleus. It also functions in the cytoplasm and in the plasma membrane to activate growth factor signaling. In some breast tumors, particularly those with highly active growth factor signaling pathways such as HER-2 amplification, a vicious cycle is established in which estrogen activates growth factor signaling, and the growth factor signaling pathway further activates ER. Estrogen in such tumors would be expected to be a dominant factor by activating multiple pathways important in tumor progression. This molecular crosstalk has important implications for the treatment of breast cancer. As an example, estrogen-deprivation therapy with aromatase inhibitors should be more effective than SERMs in HER-2 amplified tumors by shutting off both the nuclear-initiated steroid signaling and MISS activities of ER.

Metastatic Disease

Two-thirds or more of breast tumors are dependent on estrogen for growth. A number of estrogen-blocking agents may be used for treatment of metastatic breast cancer. The treatment response to these agents is unpredictable, however, and approximately one-third of patients with metastatic breast cancer with receptors for estrogen or progesterone have no benefit from hormonal therapy. Nearly all patients with metastatic breast cancer will eventually become resistant to hormonal therapy despite the fact that the hormone receptors are still present.

Therapy selection is determined based on activation of signaling pathways or a better understanding of tumor biology. The present invention advantageously provides an assay methodology along with a diagnostic/prognostic chip to help oncologists decide the best treatment for individual patients.

V. Construction of Antibody Arrays

In certain aspects, the activation state of a plurality of signal transduction molecules in a cellular extract of tumor cells such as circulating cells of a solid tumor is detected using an antibody-based array comprising a dilution series of capture antibodies restrained on a solid support. The arrays typically comprise a plurality of different capture antibodies at a range of capture antibody concentrations that are coupled to the surface of the solid support in different addressable locations.

The solid support can comprise any suitable substrate for immobilizing proteins. Examples of solid supports include, but are not limited to, glass (e.g., a glass slide), plastic, chips, pins, filters, beads, paper, membranes, fiber bundles, gels, metal, ceramics, and the like. Membranes such nylon (Biotrans™, ICN Biomedicals, Inc. (Costa Mesa, Calif.); Zeta-Probe®, Bio-Rad Laboratories (Hercules, Calif.)), nitrocellulose (Protran®, Whatman Inc. (Florham Park, N.J.)), and PVDF (Immobilon™, Millipore Corp. (Billerica, Mass.)) are suitable for use as solid supports in the arrays of the present invention. Preferably, the capture antibodies are restrained on glass slides coated with a nitrocellulose polymer, e.g., FAST® Slides, which are commercially available from Whatman Inc. (Florham Park, N.J.).

Particular aspects of the solid support which are desirable include the ability to bind large amounts of capture antibodies and the ability to bind capture antibodies with minimal denaturation. Another suitable aspect is that the solid support displays minimal "wicking" when antibody solutions containing capture antibodies are applied to the support. A solid support with minimal wicking allows small aliquots of capture antibody solution applied to the support to result in small, defined spots of immobilized capture antibody.

The capture antibodies are typically directly or indirectly (e.g., via capture tags) restrained on the solid support via covalent or noncovalent interactions (e.g., ionic bonds, hydrophobic interactions, hydrogen bonds, Van der Waals forces, dipole-dipole bonds). In some embodiments, the capture antibodies are covalently attached to the solid support using a homobifunctional or heterobifunctional crosslinker using standard crosslinking methods and conditions. Suitable crosslinkers are commercially available from vendors such as, e.g., Pierce Biotechnology (Rockford, Ill.).

Methods for generating arrays suitable for use in the present invention include, but are not limited to, any technique used to construct protein or nucleic acid arrays. In some embodiments, the capture antibodies are spotted onto an array using a microspotter, which are typically robotic printers equipped with split pins, blunt pins, or ink jet printing. Suitable robotic systems for printing the antibody arrays described herein include the PixSys 5000 robot (Cartesian Technologies; Irvine, Calif.) with ChipMaker2 split pins (TeleChem International; Sunnyvale, Calif.) as well as other robotic printers available from BioRobics (Woburn, Mass.) and Packard Instrument Co. (Meriden, Conn.). Preferably, at least 2, 3, 4, 5, or 6 replicates of each capture antibody dilution are spotted onto the array.

Another method for generating arrays suitable for use in the present invention comprises dispensing a known volume of a capture antibody dilution at each selected array position by contacting a capillary dispenser onto a solid support under conditions effective to draw a defined volume of liquid onto the support, wherein this process is repeated using selected capture antibody dilutions at each selected array position to create a complete array. The method may be practiced in forming a plurality of such arrays, where the solution-depositing step is applied to a selected position on each of a plurality of solid supports at each repeat cycle. A further description of such a method can be found, e.g., in U.S. Pat. No. 5,807,522.

In certain instances, devices for printing on paper can be used to generate the antibody arrays. For example, the desired capture antibody dilution can be loaded into the printhead of a desktop jet printer and printed onto a suitable solid support (see, e.g., Silzel et al., Clin. Chem., 44:2036-2043 (1998)).

In some embodiments, the array generated on the solid support has a density of at least about 5 spots/cm$^2$, and preferably at least about 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000, or 10,000 spots/cm$^2$.

In certain instances, the spots on the solid support each represents a different capture antibody. In certain other instances, multiple spots on the solid support represent the same capture antibody, e.g., as a dilution series comprising a series of descending capture antibody concentrations.

Additional examples of methods for preparing and constructing antibody arrays on solid supports are described in U.S. Pat. Nos. 6,197,599, 6,777,239, 6,780,582, 6,897,073, 7,179,638, and 7,192,720; U.S. Patent Publication Nos. 20060115810, 20060263837, 20060292680, and 20070054326; and Varnum et al., Methods Mol. Biol., 264: 161-172 (2004).

Methods for scanning antibody arrays are known in the art and include, without limitation, any technique used to scan protein or nucleic acid arrays. Microarray scanners suitable for use in the present invention are available from PerkinElmer (Boston, Mass.), Agilent Technologies (Palo Alto, Calif.), Applied Precision (Issaquah, Wash.), GSI Lumonics Inc. (Billerica, Mass.), and Axon Instruments (Union City, Calif.). As a non-limiting example, a GSI ScanArray3000 for fluorescence detection can be used with ImaGene software for quantitation.

VI. Single Detection Assays

In some embodiments, the assay for detecting the activation state of a particular analyte (e.g., signal transduction molecule) of interest in a cellular extract of tumor cells such as circulating cells of a solid tumor is a multiplex, high-throughput two-antibody assay having superior dynamic range. As a non-limiting example, the two antibodies used in the assay can comprise: (1) a capture antibody specific for the analyte; and (2) a detection antibody specific for an activated form of the analyte (i.e., activation state-dependent antibody). The activation state-dependent antibody is capable of detecting, for example, the phosphorylation, ubiquitination, and/or complexation state of the analyte. Alternatively, the detection antibody comprises an activation state-independent antibody, which detects the total amount of the analyte in the cellular extract. The activation state-independent antibody is generally capable of detecting both the activated and non-activated forms of the analyte.

In a preferred embodiment, the two-antibody assay comprises:
 (i) incubating the cellular extract with a plurality of dilution series of capture antibodies to form a plurality of captured analytes;
 (ii) incubating the plurality of captured analytes with activation state-dependent antibodies specific for the corresponding analytes to form a plurality of detectable captured analytes;
 (iii) incubating the plurality of detectable captured analytes with first and second members of a signal amplification pair to generate an amplified signal; and
 (iv) detecting the amplified signal generated from the first and second members of the signal amplification pair.

The two-antibody assays described herein are typically antibody-based arrays which comprise a plurality of different capture antibodies at a range of capture antibody concentrations that are coupled to the surface of a solid support in different addressable locations. Examples of suitable solid supports for use in the present invention are described above.

The capture antibodies and detection antibodies are preferably selected to minimize competition between them with respect to analyte binding (i.e., both capture and detection antibodies can simultaneously bind their corresponding signal transduction molecules).

In one embodiment, the detection antibodies comprise a first member of a binding pair (e.g., biotin) and the first member of the signal amplification pair comprises a second member of the binding pair (e.g., streptavidin). The binding pair members can be coupled directly or indirectly to the detection antibodies or to the first member of the signal amplification pair using methods well-known in the art. In certain instances, the first member of the signal amplification pair is a peroxidase (e.g., horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, etc.), and the second member of the signal amplification pair is a tyramide reagent (e.g., biotin-tyramide). In these instances, the amplified signal is generated by peroxidase oxidization of the tyramide reagent to produce an activated tyramide in the presence of hydrogen peroxide ($H_2O_2$).

The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

An exemplary protocol for performing the two-antibody assays described herein is provided in Example 3.

In another embodiment, the present invention provides kits for performing the two-antibody assays described above comprising: (a) a dilution series of a plurality of capture antibodies restrained on a solid support; and (b) a plurality of detection antibodies (e.g., activation state-independent antibodies and/or activation state-dependent antibodies). In some instances, the kits can further contain instructions for methods of using the kit to detect the activation states of a plurality of signal transduction molecules of circulating cells of a solid tumor. The kits may also contain any of the additional reagents described above with respect to performing the specific methods of the present invention such as, for example, first and second members of the signal amplification pair, tyramide signal amplification reagents, wash buffers, etc.

In another embodiment of a two-antibody approach, the present invention provides a method for detecting the presence of a truncated receptor, the method comprising:
 (a) incubating a cellular extract with a plurality of beads specific for an extracellular domain (ECD) binding region, wherein the ECD binding region is specific for a full-length receptor;
 (b) removing the plurality of beads from the cellular extract, thereby removing the full length receptors to form a cellular extract devoid of the full length receptors;
 (c) incubating said cellular extract devoid of said full length receptors with a plurality of capture antibodies, wherein said plurality of capture antibodies are specific for an intracellular domain (ICD) binding region of said truncated receptor and wherein said plurality of captured antibodies are restrained on a solid support to form a plurality of captured truncated receptors;
 (d) incubating the plurality of captured truncated receptors with detection antibodies specific for the corresponding truncated receptors to form a plurality of detectable captured truncated receptors;
 (e) incubating the plurality of detectable captured truncated receptors with first and second members of a signal amplification pair to generate an amplified signal; and
 (f) detecting an amplified signal generated from the first and second members of the signal amplification pair.

In certain embodiments, the truncated receptor is p95 ErbB2 and the full-length receptor is ErbB2 (HER-2). In certain other aspects, the plurality of beads specific for an extracellular domain (ECD) binding region comprise a streptavidin-biotin pair, wherein the biotin is attached to the bead and the biotin is attached to an antibody (e.g., wherein the antibody is specific for the ECD binding region of the full-length receptor).

Figure 14A:
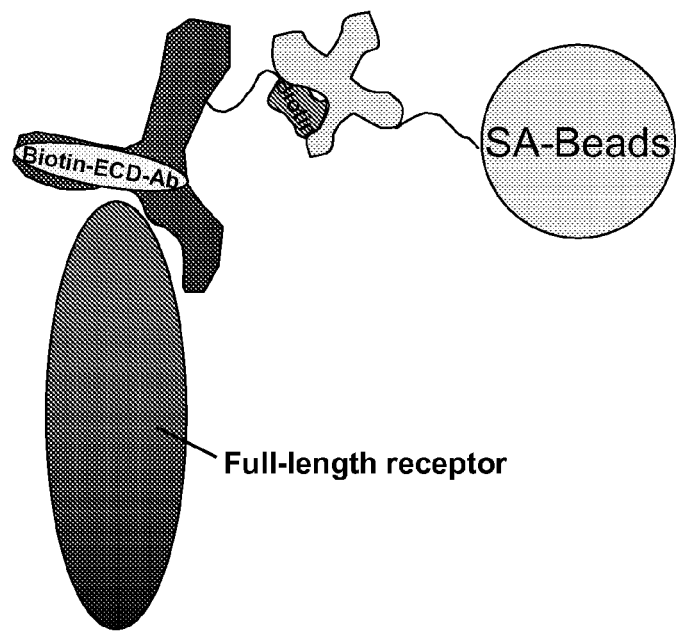
FIGS. 14A and 14B show an embodiment of the present invention for detecting truncated receptors such as p95ErbB2. SA=streptavidin; HRP=horseradish peroxidase; TSA=tyramide signal amplification.
Figure 14B:
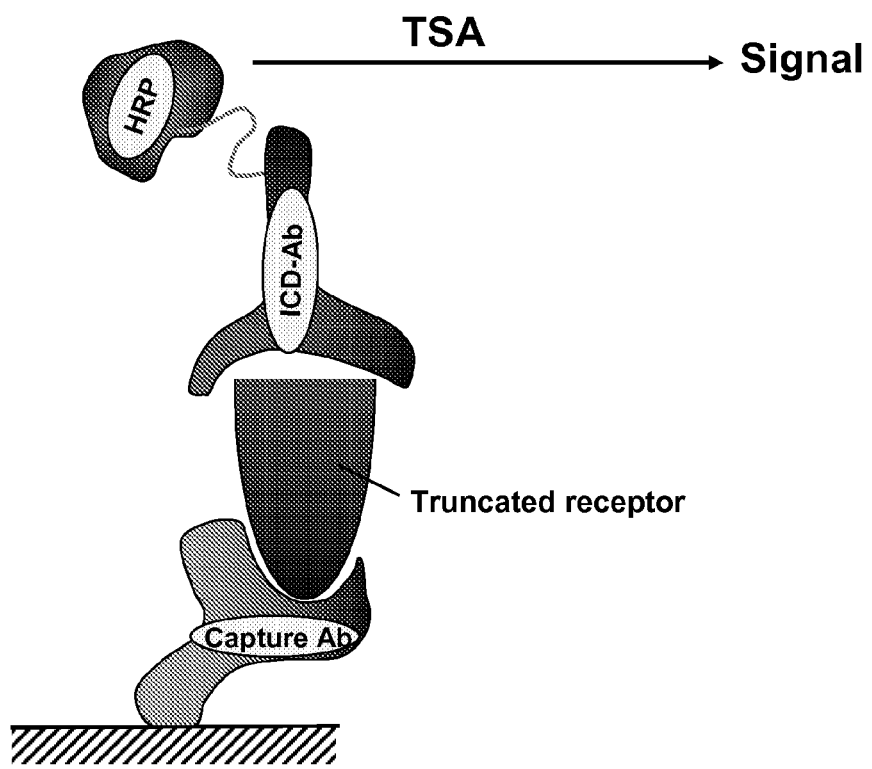

FIG. 14A shows that beads coated with an antibody directed to the extracellular domain (ECD) of a receptor of interest binds the full-length receptor (e.g., ErbB2), but not the truncated receptor (e.g., p95) to remove any full-length receptor from the assay. FIG. 14B shows that the truncated receptor (e.g., p95), once bound to a capture antibody, may then be detected by a detection antibody that is specific for the intracellular domain (ICD) of the full-length receptor (e.g., ErbB2). The detection antibody may be directly conjugated to horseradish peroxidase (HRP). Tyramide signal amplification (TSA) may then be performed to generate a signal to be detected. The activation state of the p95 can be interrogated to determine, for example, its phosphorylation state, ubiquitination state, and/or complexation state.

VII. Proximity Dual Detection Assays

In some embodiments, the assay for detecting the activation state of a particular analyte (e.g., signal transduction molecule) of interest in a cellular extract of tumor cells such as circulating cells of a solid tumor is a multiplex, high-throughput proximity (i.e., three-antibody) assay having superior dynamic range. As a non-limiting example, the three antibodies used in the proximity assay can comprise: (1) a capture antibody specific for the analyte; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, for example, the phosphorylation, ubiquitination, and/or complexation state of the analyte. The activation state-dependent antibody is generally capable of detecting both the activated and non-activated forms of the analyte.

In a preferred embodiment, the proximity assay comprises:
- (i) incubating the cellular extract with a plurality of dilution series of capture antibodies to form a plurality of captured analytes;
- (ii) incubating the plurality of captured analytes with detection antibodies comprising a plurality of activation state-independent antibodies and a plurality of activation state-dependent antibodies specific for the corresponding analytes to form a plurality of detectable captured analytes,
  wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
- (iii) incubating the plurality of detectable captured analytes with a second member of the signal amplification pair to generate an amplified signal; and
- (iv) detecting the amplified signal generated from the first and second members of the signal amplification pair.

Alternatively, the activation state-dependent antibodies can be labeled with a facilitating moiety and the activation state-independent antibodies can be labeled with a first member of a signal amplification pair.

The proximity assays described herein are typically antibody-based arrays which comprise a plurality of different capture antibodies at a range of capture antibody concentrations that are coupled to the surface of a solid support in different addressable locations. Examples of suitable solid supports for use in the present invention are described above.

The capture antibodies, activation state-independent antibodies, and activation state-dependent antibodies are preferably selected to minimize competition between them with respect to analyte binding (i.e., all antibodies can simultaneously bind their corresponding signal transduction molecules).

In some embodiments, the activation state-independent antibodies further comprise a detectable moiety. In such instances, the amount of the detectable moiety is correlative to the amount of one or more of the analytes in the cellular extract. Examples of detectable moieties include, but are not limited to, fluorescent labels, chemically reactive labels, enzyme labels, radioactive labels, and the like. Preferably, the detectable moiety is a fluorophore such as an Alexa Fluor® dye (e.g., Alexa Fluor® 647), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The detectable moiety can be coupled directly or indirectly to the activation state-independent antibodies using methods well-known in the art.

In certain instances, the activation state-independent antibodies are directly labeled with the facilitating moiety. The facilitating moiety can be coupled to the activation state-independent antibodies using methods well-known in the art. A suitable facilitating moiety for use in the present invention includes any molecule capable of generating an oxidizing agent which channels to (i.e., is directed to) and reacts with (i.e., binds, is bound by, or forms a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

In certain other instances, the activation state-independent antibodies are indirectly labeled with the facilitating moiety via hybridization between an oligonucleotide linker conjugated to the activation state-independent antibodies and a complementary oligonucleotide linker conjugated to the facilitating moiety. The oligonucleotide linkers can be coupled to the facilitating moiety or to the activation state-independent antibodies using methods well-known in the art. In some embodiments, the oligonucleotide linker conjugated to the facilitating moiety has 100% complementarity to the oligonucleotide linker conjugated to the activation state-independent antibodies. In other embodiments, the oligonucleotide linker pair comprises at least one, two, three, four, five, six, or more mismatch regions, e.g., upon hybridization under stringent hybridization conditions. One skilled in the art will appreciate that activation state-independent antibodies specific for different analytes can either be conjugated to the same oligonucleotide linker or to different oligonucleotide linkers.

The length of the oligonucleotide linkers that are conjugated to the facilitating moiety or to the activation state-independent antibodies can vary. In general, the linker sequence can be at least about 5, 10, 15, 20, 25, 30, 35, 40, 45, 50, 75, or 100 nucleotides in length. Typically, random nucleic acid sequences are generated for coupling. As a non-limiting example, a library of oligonucleotide linkers can be designed to have three distinct contiguous domains: a spacer domain; signature domain; and conjugation domain. Preferably, the oligonucleotide linkers are designed for efficient coupling without destroying the function of the facilitating moiety or activation state-independent antibodies to which they are conjugated.

The oligonucleotide linker sequences can be designed to prevent or minimize any secondary structure formation under a variety of assay conditions. Melting temperatures are typically carefully monitored for each segment within the linker to allow their participation in the overall assay procedures. Generally, the range of melting temperatures of the segment of the linker sequence is between 1-10° C. Computer algorithms (e.g., OLIGO 6.0) for determining the melting temperature, secondary structure, and hairpin structure under defined ionic concentrations can be used to analyze each of the three different domains within each linker. The overall combined sequences can also be analyzed for their structural characterization and their comparability to other conjugated oligonucleotide linker sequences, e.g., whether they will hybridize under stringent hybridization conditions to a complementary oligonucleotide linker.

The spacer region of the oligonucleotide linker provides adequate separation of the conjugation domain from the oligonucleotide crosslinking site. The conjugation domain functions to link molecules labeled with a complementary oligonucleotide linker sequence to the conjugation domain via nucleic acid hybridization. The nucleic acid-mediated hybridization can be performed either before or after antibody-analyte (i.e., antigen) complex formation, providing a more flexible assay format. Unlike many direct antibody conjugation methods, linking relatively small oligonucleotides to antibodies or other molecules has minimal impact on the specific affinity of antibodies towards their target analyte or on the function of the conjugated molecules.

In some embodiments, the signature sequence domain of the oligonucleotide linker can be used in complex multiplexed protein assays. Multiple antibodies can be conjugated with oligonucleotide linkers with different signature sequences. In multiplex immunoassays, reporter oligonucleotide sequences labeled with appropriate probes can be used to detect cross-reactivity between antibodies and their antigens in the multiplex assay format.

Oligonucleotide linkers can be conjugated to antibodies or other molecules using several different methods. For example, oligonucleotide linkers can be synthesized with a thiol group on either the 5' or 3' end. The thiol group can be deprotected using reducing agents (e.g., TCEP-HCl) and the resulting linkers can be purified by using a desalting spin column. The resulting deprotected oligonucleotide linkers can be conjugated to the primary amines of antibodies or other types of proteins using heterobifunctional cross linkers such as SMCC. Alternatively, 5'-phosphate groups on oligonucleotides can be treated with water-soluble carbodiimide EDC to form phosphate esters and subsequently coupled to amine-containing molecules. In certain instances, the diol on the 3'-ribose residue can be oxidized to aldehyde groups and then conjugated to the amine groups of antibodies or other types of proteins using reductive amination. In certain other instances, the oligonucleotide linker can be synthesized with a biotin modification on either the 3' or 5' end and conjugated to streptavidin-labeled molecules.

Oligonucleotide linkers can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). In general, the synthesis of oligonucleotides makes use of common nucleic acid protecting and coupling groups, such as dimethoxytrityl at the 5'-end and phosphoramidites at the 3'-end. Suitable reagents for oligonucleotide synthesis, methods for nucleic acid deprotection, and methods for nucleic acid purification are known to those of skill in the art.

In certain instances, the activation state-dependent antibodies are directly labeled with the first member of the signal amplification pair. The signal amplification pair member can be coupled to the activation state-dependent antibodies using methods well-known in the art. In certain other instances, the activation state-dependent antibodies are indirectly labeled with the first member of the signal amplification pair via binding between a first member of a binding pair conjugated to the activation state-dependent antibodies and a second member of the binding pair conjugated to the first member of the signal amplification pair. The binding pair members (e.g., biotin/streptavidin) can be coupled to the signal amplification pair member or to the activation state-dependent antibodies using methods well-known in the art. Examples of signal amplification pair members include, but are not limited to, peroxidases such horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. Methods of using GO and HRP in a proximity assay are described in, e.g., Langry et al., U.S. Dept. of Energy Report No. UCRL-ID-136797 (1999). When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azinobis(3-ethylbenzothiazoline-6-sulfonic acid) (ABTS), 4-chloro-1-napthol (4CN), and/or porphyrinogen.

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, olefin-, thioether-, and selenoether-protecting groups. Additional photosensitizers and protected hapten molecules suitable for use in the proximity assays of the present invention are described in U.S. Pat. No. 5,807, 675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and sulphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, $\beta$-galactosidase, HRP, etc. After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

An exemplary protocol for performing the proximity assays described herein is provided in Example 4.

In another embodiment, the present invention provides kits for performing the proximity assays described above comprising: (a) a dilution series of a plurality of capture antibodies restrained on a solid support; and (b) a plurality of detection antibodies (e.g., activation state-independent antibodies and activation state-dependent antibodies). In some instances, the kits can further contain instructions for methods of using the kit to detect the activation states of a plurality of signal transduction molecules of circulating cells of a solid tumor. The kits may also contain any of the additional reagents described above with respect to performing the specific methods of the present invention such as, for example, first and second members of the signal amplification pair, tyramide signal amplification reagents, substrates for the facilitating moiety, wash buffers, etc.

VIII. Production of Antibodies

The generation and selection of antibodies not already commercially available for analyzing the activation states of signal transduction molecules in tumor cells such as rare circulating cells in accordance with the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., Guide to Protein Purification, Murray P. Deutcher, ed., Meth. Enzymol., Vol. 182 (1990); Solid Phase Peptide Synthesis, Greg B. Fields, ed., Meth. Enzymol., Vol. 289 (1997); Kiso et al., Chem. Pharm. Bull., 38:1192-99 (1990); Mostafavi et al., Biomed. Pept. Proteins Nucleic Acids, 1:255-60, (1995); and Fujiwara et al., Chem. Pharm. Bull., 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in Antibodies, A Laboratory Manual, Harlow and Lane, Eds., Cold Spring Harbor Laboratory, Cold Spring Harbor, N.Y. (1988). One skilled in the art will also appreciate that binding fragments or Fab fragments which mimic (e.g., retain the functional binding regions of) antibodies can also be prepared from genetic information by various procedures. See, e.g., Antibody Engineering: A Practical Approach, Borrebaeck, Ed., Oxford University Press, Oxford (1995); and Huse et al., J. Immunol., 149:3914-3920 (1992).

In addition, numerous publications have reported the use of phage display technology to produce and screen libraries of polypeptides for binding to a selected target antigen (see, e.g, Cwirla et al., Proc. Natl. Acad. Sci. USA, 87:6378-6382 (1990); Devlin et al., Science, 249:404-406 (1990); Scott et al., Science, 249:386-388 (1990); and Ladner et al., U.S. Pat. No. 5,571,698). A basic concept of phage display methods is the establishment of a physical association between a polypeptide encoded by the phage DNA and a target antigen. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target antigen bind to the target antigen and these phage are enriched by affinity screening to the target antigen. The identity of polypeptides displayed from these phage can be determined from their respective genomes. Using these methods, a polypeptide identified as having a binding affinity for a desired target antigen can then be synthesized in bulk by conventional means (see, e.g., U.S. Pat. No. 6,057,098).

The antibodies that are generated by these methods can then be selected by first screening for affinity and specificity with the purified polypeptide antigen of interest and, if required, comparing the results to the affinity and specificity of the antibodies with other polypeptide antigens that are desired to be excluded from binding. The screening procedure can involve immobilization of the purified polypeptide antigens in separate wells of microtiter plates. The solution containing a potential antibody or group of antibodies is then placed into the respective microtiter wells and incubated for about 30 minutes to 2 hours. The microtiter wells are then washed and a labeled secondary antibody (e.g., an anti-mouse antibody conjugated to alkaline phosphatase if the raised antibodies are mouse antibodies) is added to the wells and incubated for about 30 minutes and then washed. Substrate is added to the wells and a color reaction will appear where antibody to the immobilized polypeptide antigen is present.

The antibodies so identified can then be further analyzed for affinity and specificity. In the development of immunoassays for a target protein, the purified target protein acts as a standard with which to judge the sensitivity and specificity of the immunoassay using the antibodies that have been selected. Because the binding affinity of various antibodies may differ, e.g., certain antibody combinations may interfere with one another sterically, assay performance of an antibody may be a more important measure than absolute affinity and specificity of that antibody.

Those skilled in the art will recognize that many approaches can be taken in producing antibodies or binding fragments and screening and selecting for affinity and specificity for the various polypeptides of interest, but these approaches do not change the scope of the present invention.

A. Polyclonal Antibodies

Polyclonal antibodies are preferably raised in animals by multiple subcutaneous (sc) or intraperitoneal (ip) injections of a polypeptide of interest and an adjuvant. It may be useful to conjugate the polypeptide of interest to a protein carrier that is immunogenic in the species to be immunized, such as, e.g., keyhole limpet hemocyanin, serum albumin, bovine thyroglobulin, or soybean trypsin inhibitor using a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, $SOCl_2$, and $R_1N=C=NR$, wherein R and $R_1$ are different alkyl groups.

Animals are immunized against the polypeptide of interest or an immunogenic conjugate or derivative thereof by combining, e.g., 100 µg (for rabbits) or 5 µg (for mice) of the antigen or conjugate with 3 volumes of Freund's complete adjuvant and injecting the solution intradermally at multiple sites. One month later, the animals are boosted with about ⅕ to ⅒ the original amount of polypeptide or conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same polypeptide, but conjugation to a different immunogenic protein and/or through a different cross-linking reagent may be used. Conjugates can also be made in recombinant cell culture as fusion proteins. In certain instances, aggregating agents such as alum can be used to enhance the immune response.

B. Monoclonal Antibodies

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., *Nature,* 256:495 (1975) or by any recombinant DNA method known in the art (see, e.g., U.S. Pat. No. 4,816,567).

In the hybridoma method, a mouse or other appropriate host animal (e.g., hamster) is immunized as described above to elicit lymphocytes that produce or are capable of producing antibodies which specifically bind to the polypeptide of interest used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice,* Academic Press, pp. 59-103 (1986)). The hybridoma cells thus prepared are seeded and grown in a suitable culture medium that preferably contains one or more substances which inhibit the growth or survival of the unfused, parental myeloma cells. For example, if the parental myeloma cells lack the enzyme hypoxanthine guanine phosphoribosyl transferase (HGPRT), the culture medium for the hybridoma cells will typically include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.,* 133:3001 (1984); and Brodeur et al., *Monoclonal Antibody Production Techniques and Applications,* Marcel Dekker, Inc., New York, pp. 51-63 (1987)).

The culture medium in which hybridoma cells are growing can be assayed for the production of monoclonal antibodies directed against the polypeptide of interest. Preferably, the binding specificity of monoclonal antibodies produced by hybridoma cells is determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (see, e.g., Goding, *Monoclonal Antibodies: Principles and Practice,* Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody, to induce the synthesis of monoclonal antibodies in the recombinant host cells. See, e.g., Skerra et al., *Curr. Opin. Immunol.,* 5:256-262 (1993); and Pluckthun, *Immunol Rev.,* 130:151-188 (1992). The DNA can also be modified, for example, by substituting the coding sequence for human heavy chain and light chain constant domains in place of the homologous murine sequences (see, e.g., U.S. Pat. No. 4,816,567; and Morrison et al., *Proc. Natl. Acad. Sci. USA,* 81:6851 (1984)), or by covalently joining to the immunoglobulin coding sequence all or part of the coding sequence for a non-immunoglobulin polypeptide.

In a further embodiment, monoclonal antibodies or antibody fragments can be isolated from antibody phage libraries generated using the techniques described in, for example, McCafferty et al., *Nature,* 348:552-554 (1990); Clackson et al., *Nature,* 352:624-628 (1991); and Marks et al., *J. Mol. Biol.,* 222:581-597 (1991). The production of high affinity (nM range) human monoclonal antibodies by chain shuffling is described in Marks et al., *BioTechnology,* 10:779-783 (1992). The use of combinatorial infection and in vivo recombination as a strategy for constructing very large phage libraries is described in Waterhouse et al., *Nuc. Acids Res.,* 21:2265-2266 (1993). Thus, these techniques are viable alternatives to traditional monoclonal antibody hybridoma methods for the generation of monoclonal antibodies.

C. Humanized Antibodies

Methods for humanizing non-human antibodies are known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed by substituting the hypervariable region sequences of a non-human antibody for the corresponding sequences of a human antibody. See, e.g., Jones et al., *Nature,* 321:522-525 (1986); Riechmann et al., *Nature,* 332:323-327 (1988); and Verhoeyen et al., *Science,* 239: 1534-1536 (1988). Accordingly, such "humanized" antibodies are chimeric antibodies (see, e.g., U.S. Pat. No. 4,816, 567), wherein substantially less than an intact human variable domain has been substituted by the corresponding sequence from a non-human species. In practice, humanized antibodies are typically human antibodies in which some hypervariable region residues and possibly some framework region (FR) residues are substituted by residues from analogous sites of rodent antibodies.

The choice of human variable domains, both light and heavy, to be used in making the humanized antibodies described herein is an important consideration for reducing antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (see, e.g., Sims et al., *J. Immunol.,* 151: 2296 (1993); and Chothia et al., *J. Mol. Biol.,* 196:901 (1987)). Another method uses a particular FR derived from the consensus sequence of all human antibodies of a particular subgroup of light or heavy chains. The same FR may be used for several different humanized antibodies (see, e.g., Carter et al., *Proc. Natl. Acad. Sci. USA,* 89:4285 (1992); and Presta et al., *J. Immunol.,* 151:2623 (1993)).

It is also important that antibodies be humanized with retention of high affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and specifically involved in influencing antigen binding.

Various forms of humanized antibodies are contemplated in accordance with the present invention. For example, the humanized antibody can be an antibody fragment, such as a Fab fragment. Alternatively, the humanized antibody can be an intact antibody, such as an intact IgA, IgG, or IgM antibody.

D. Human Antibodies

As an alternative to humanization, human antibodies can be generated. In some embodiments, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immun.,* 7:33 (1993); and U.S. Pat. Nos. 5,591,669, 5,589, 369, and 5,545,807.

Alternatively, phage display technology (see, e.g., McCafferty et al., *Nature,* 348:552-553 (1990)) can be used to produce human antibodies and antibody fragments in vitro, using immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats as described in, e.g., Johnson et al., *Curr. Opin. Struct. Biol.,* 3:564-571 (1993). Several sources of V-gene segments can be used for phage display. See, e.g., Clackson et al., *Nature,* 352:624-628 (1991). A repertoire of V genes from unimmunized human donors can be constructed and antibodies to a diverse array of antigens (including self-antigens) can be isolated essentially following the techniques described in Marks et al., *J. Mol. Biol.,* 222:581-597 (1991); Griffith et al., *EMBO J.,* 12:725-734 (1993); and U.S. Pat. Nos. 5,565,332 and 5,573,905.

In certain instances, human antibodies can be generated by in vitro activated B cells as described in, e.g., U.S. Pat. Nos. 5,567,610 and 5,229,275.

E. Antibody Fragments

Various techniques have been developed for the production of antibody fragments. Traditionally, these fragments were derived via proteolytic digestion of intact antibodies (see, e.g., Morimoto et al., *J. Biochem. Biophys. Meth.,* 24:107-117 (1992); and Brennan et al., *Science,* 229:81 (1985)). However, these fragments can now be produced directly using recombinant host cells. For example, the antibody fragments can be isolated from the antibody phage libraries discussed above. Alternatively, Fab'-SH fragments can be directly recovered from *E. coli* cells and chemically coupled to form F(ab')$_2$ fragments (see, e.g., Carter et al., *BioTechnology*, 10:163-167 (1992)). According to another approach, F(ab')$_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870. Such linear antibody fragments may be monospecific or bispecific.

F. Bispecific Antibodies

Bispecific antibodies are antibodies that have binding specificities for at least two different epitopes. Exemplary bispecific antibodies may bind to two different epitopes of the same polypeptide of interest. Other bispecific antibodies may combine a binding site for the polypeptide of interest with binding site(s) for one or more additional antigens. Bispecific antibodies can be prepared as full-length antibodies or antibody fragments (e.g., F(ab')$_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities (see, e.g., Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually performed by affinity chromatography. Similar procedures are disclosed in PCT Publication No. WO 93/08829 and Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains into one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. See, e.g., PCT Publication No. WO 94/04690 and Suresh et al., *Meth. Enzymol.*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side-chains from the interface of the first antibody molecule are replaced with larger side chains (e.g., tyrosine or tryptophan). Compensatory "cavities" of identical or similar size to the large side-chain(s) are created on the interface of the second antibody molecule by replacing large amino acid side-chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies can be made using any convenient cross-linking method. Suitable cross-linking agents and techniques are well-known in the art, and are disclosed in, e.g., U.S. Pat. No. 4,676,980.

Suitable techniques for generating bispecific antibodies from antibody fragments are also known in the art. For example, bispecific antibodies can be prepared using chemical linkage. In certain instances, bispecific antibodies can be generated by a procedure in which intact antibodies are proteolytically cleaved to generate F(ab')$_2$ fragments (see, e.g., Brennan et al., *Science*, 229:81 (1985)). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

In some embodiments, Fab'-SH fragments can be directly recovered from *E. coli* and chemically coupled to form bispecific antibodies. For example, a fully humanized bispecific antibody F(ab')$_2$ molecule can be produced by the methods described in Shalaby et al., *J. Exp. Med.*, 175: 217-225 (1992). Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. See, e.g., Kostelny et al., *J. Immunol.*, 148:1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VL and VH domains of another fragment, thereby forming two antigen binding sites. Another strategy for making bispecific antibody fragments by the use of single-chain Fv (sFv) dimers is described in Gruber et al., *J. Immunol.*, 152:5368 (1994).

Antibodies with more than two valencies are also contemplated. For example, trispecific antibodies can be prepared. See, e.g., Tutt et al., *J. Immunol.*, 147:60 (1991).

G. Antibody Purification

When using recombinant techniques, antibodies can be produced inside an isolated host cell, in the periplasmic space of a host cell, or directly secreted from a host cell into the medium. If the antibody is produced intracellularly, the particulate debris is first removed, for example, by centrifugation or ultrafiltration. Carter et al., *BioTech.*, 10:163-167 (1992) describes a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) for about 30 min. Cell debris can be removed by centrifugation. Where the antibody is secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (see, e.g., Lindmark et al., *J. Immunol. Meth.*, 62:1-13 (1983)). Protein G is recommended for all mouse isotypes and for human $\gamma 3$ (see, e.g., Guss et al., *EMBO J.*, 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

One of skill in the art will appreciate that any binding molecule having a function similar to an antibody, e.g., a binding molecule or binding partner which is specific for one or more analytes of interest in a sample, can also be used in the methods and compositions of the present invention. Examples of suitable antibody-like molecules include, but are not limited to, domain antibodies, unibodies, nanobodies, shark antigen reactive proteins, avimers, adnectins, anticalins, affinity ligands, phylomers, aptamers, affibodies, trinectins, and the like.

IX. Methods of Administration

According to the methods of the present invention, the anticancer drugs described herein are administered to a subject by any convenient means known in the art. The methods of the present invention can be used to select a suitable anticancer drug or combination of anticancer drugs for the treatment of a tumor (e.g., breast tumor) in a subject. The methods of the invention can also be used to identify the response of a tumor (e.g., breast tumor) in a subject to treatment with an anticancer drug or combination of anticancer drugs. In addition, the methods of the invention can be used to predict the response of a subject having a tumor (e.g., breast tumor) to treatment with an anticancer drug or combination of anticancer drugs. One skilled in the art will appreciate that the anticancer drugs described herein can be administered alone or as part of a combined therapeutic approach with conventional chemotherapy, radiotherapy, hormonal therapy, immunotherapy, and/or surgery.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the subject is treated with one or more anti-signaling agents, anti-proliferative agents, and/or hormonal therapeutic agents in combination with at least one chemotherapeutic agent. Exemplary monoclonal antibodies, tyrosine kinase inhibitors, anti-proliferative agents, chemotherapeutic agents, hormonal therapeutic agents, radiotherapeutic agents, and vaccines are described above.

In some embodiments, the anticancer drugs described herein can be co-administered with conventional immunotherapeutic agents including, but not limited to, immunostimulants (e.g., *Bacillus* Calmette-Guérin (BCG), levamisole, interleukin-2, alpha-interferon, etc.), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

Anticancer drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that an anticancer drug is administered at the same time, just prior to, or just after the administration of a second drug (e.g., another anticancer drug, a drug useful for reducing the side-effects associated with anticancer drug therapy, a radiotherapeutic agent, a hormonal therapeutic agent, an immunotherapeutic agent, etc.).

A therapeutically effective amount of an anticancer drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an anticancer drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anticancer drug.

Methods for preparing such dosage forms are known to those skilled in the art (see, e.g., *Remington's Pharmaceutical Sciences,* 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *Remington's Pharmaceutical Sciences,* supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anticancer drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An anticancer drug can also be formulated into a suppository disposed, for example, in a polyethylene glycol (PEG) carrier.

Liquid dosage forms can be prepared by dissolving or dispersing an anticancer drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anticancer drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anticancer drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the activation states of certain signal transduction molecules may change based on the therapeutic effect of treatment with one or more of the anticancer drugs described herein. The subject can be monitored to assess response and understand the effects of certain drugs or treatments in an individualized approach. Additionally, subjects who initially respond to a specific anticancer drug or combination of anticancer drugs may become refractory to the drug or drug combination, indicating that these subjects have developed acquired drug resistance. These subjects can be discontinued on their current therapy and an alternative treatment prescribed in accordance with the methods of the present invention.

In certain aspects, the methods described herein can be used in conjunction with panels of gene expression markers that predict the likelihood of breast cancer prognosis and/or recurrence in various populations of women with for example, node-negative disease. These gene panels can be useful for identifying women who are unlikely to experience recurrence and, thus, unlikely to benefit from adjuvant chemotherapy. The expression panels can be used to identify women who can safely avoid adjuvant chemotherapy, without negatively affecting disease-free and overall survival outcomes. Suitable systems include, but are not limited to, Oncotype DX™, which is a 21-gene panel from Genomic Health, Inc.; MammaPrint,® which is a 70-gene panel from Agendia; and a 76-gene panel from Veridex.

In addition, in certain other aspects, the methods described herein can be used in conjunction with panels of gene expression markers that identify the original tumors for cancers of unknown primary (CUP). These gene panels can be useful in identifying women with metastatic cancer who would benefit from therapy consistent with that given to women diagnosed initially with breast cancer. Suitable systems include, but are not limited to, the Aviara CancerTYPE ID assay, an RT-PCR-based expression assay that measures 92 genes to identify the primary site of origin for 39 tumor types; and the Pathwork® Tissue of Origin Test, which measures the expression of more than 1600 genes on a microarray and compares a tumor's gene expression "signature" against those of 15 known tissue types."

X. Examples

The following examples are offered to illustrate, but not to limit, the claimed invention.

Example 1

Isolation, Stimulation, and Lysis of Circulating Cells

Circulating cells of a solid tumor comprise cells that have either metastasized or micrometastasized from a solid tumor and include circulating tumor cells (CTCs), cancer stem cells (CSCs), and/or cells that are migrating to the tumor (e.g., circulating endothelial progenitor cells (CEPCs), circulating endothelial cells (CECs), circulating pro-angiogenic myeloid cells, circulating dendritic cells, etc.). Patient samples containing circulating cells can be obtained from any accessible biological fluid (e.g., whole blood, serum, plasma, ductal lavage fluid, nipple aspirate, lymph, urine, saliva, fine needle aspirate, etc.). The circulating cells can be isolated from a patient sample using one or more separation methods such as, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), the CellTrack™ System by Immunicon (Huntingdon Valley, Pa.), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)).

Manual Isolation of CTCs:

Immunomagnetic separation of CTCs—manual isolation followed by an activation assay:
1) Magnetic beads (Dynal M450; Dynal AS; Oslo, Norway) that have been previously conjugated to an anti-EpCAM monoclonal antibody (Kordia Life Sciences; Leiden, The Netherlands) are used. Alternatively, polyclonal antibodies or mixtures of monoclonal antibodies can be used.
2) Just prior to use, the pre-coated Dynabeads are washed once in an equal volume of PBS with BSA at 0.01%.
3) 25 µl of the pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample preparation:
1) Peripheral blood from human subjects is drawn in a siliconized tube containing 1 mg/ml EDTA. The first 3-5 ml is discarded to avoid contamination with epithelial cells released from the punctured vein.
2) 1 ml of whole blood is diluted 1:3 with 0.9% NaCl prior to use.

Control preparation:
1) Cell line controls are made by spiking human cancer cell lines into HL-60 cells.
2) Cell line controls are made by spiking human cancer cell lines into whole blood from healthy donors.

Manual Isolation of CECs and CEPCs:

As a non-limiting example, viable CECs and CEPCs can be isolated using the immunomagnetic isolation/enrichment technique described in Beerepoot et al., *Ann. Oncology*, 15:139-145 (2004). Briefly, peripheral blood is incubated with magnetic beads (Dynal M450 IgG$_1$) that have been previously conjugated to an anti-CD146 monoclonal antibody (Kordia Life Sciences). This antibody recognizes all lineages of endothelial cells, but not hematopoetic or epithelial cells, in peripheral blood (George et al., *J. Immunol. Meth.*, 139:65-75 (1991)). Negative selection of hematopoetic and epithelial cells can be used prior to the positive selection with magnetic beads conjugated to appropriate antibodies (e.g., Dynal-CD45 beads for depleting leukocytes, Dynal-CD14 beads for depleting monocytes, Dynal-EpCAM for depleting epithelial cells (Invitrogen; Carlsbad, Calif.)). In this example, only positive selection is used.

Immunomagnetic separation of CECs and CEPCs—manual isolation followed by an activation assay:
1) Magnetic beads (Dynal M450) that have been previously conjugated to an anti-CD146 monoclonal antibody (Kordia Life Sciences) are used.
2) Just prior to use, the pre-coated Dynabeads are washed once in an equal volume of PBS with BSA at 0.01%.
3) 25 µl pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample preparation:
1) Peripheral blood from human subjects is drawn in a siliconized tube containing 1 mg/ml EDTA. The first 3-5 ml is discarded to avoid contamination with endothelial cells released from the punctured vein.
2) 1 ml of whole blood is diluted 1:3 with 0.9% NaCl prior to use.

Control preparation:
1) Cell line controls are made by spiking human umbilical vein endothelial cells (HUVEC) into HL-60 cells.
2) Cell line controls are made by spiking human umbilical vein endothelial cells (HUVEC) into whole blood donated by healthy individuals.

Manual Isolation of CEPCs (without CECs):

CEPCs are a circulating subtype of bone marrow-derived progenitor cells that have the capacity of differentiating into mature endothelial cells in response to various angiogenic growth factors. CEPCs may be isolated by selection with antibodies recognizing the surface marker CD34. CD133 is a surface marker that differentiates immature endothelial progenitor cells (EPCs) or primitive hematopoetic stem cells (HSCs) from CEPCs. Various isolation procedures of CEPCs from different sources have been described using adherence culture or magnetic microbeads. In this example, a protocol modified from that described in Asahara et al., *Science*, 275:964-967 (1997) is used.

Immunomagnetic separation of CEPCs—manual isolation followed by an activation assay:
1) Magnetic beads (Dynal M450 CD34) are used. These beads are coated with a monoclonal antibody specific for the CD34 surface antigen.
2) Just prior to use, the pre-coated Dynabeads are washed once in an equal volume of PBS with BSA at 0.01%.
3) 25 µl pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.

7) The sample is resuspended in 100 μl of stimulation buffer.

Sample preparation:
1) Peripheral blood from human subjects is drawn in a siliconized tube containing 1 mg/ml EDTA. The first 3-5 ml is discarded to avoid contamination with endothelial cells released from the punctured vein.
2) 10 ml of blood is diluted 1:1 with a balanced salt solution.
3) 4 ml of diluted blood is layered onto 3 ml of Ficoll-Paque in 10 ml tubes.
4) Tubes are spun at 400×g for 30-40 min at 18-20° C.
5) The upper layer containing plasma and platelets is drawn off using a sterile Pasteur pipette, leaving the layer of mononuclear cells undisturbed at the interface.
6) The mononuclear cells are transferred to a sterile centrifuge tube using a sterile pipette.
7) 6 ml of balanced salt solution is added and the cells are gently resuspended.
8) The mixture is centrifuged at 60-100×g for 10 min at 18-20° C.
9) The supernatant is removed and the mononuclear cells from each tube are resuspended in 1 ml PBS.

Cell Isolation of CTCs, CECs, and CEPCs Using the Veridex System:

Veridex, LLC (Warren, N.J.) has commercialized the CellSearch system, which consists of the CellTracks® AutoPrep® System, the CellSearch™ Epithelial Cell Kit, and the CellTracks® Analyzer. The CellTracks® AutoPrep® System is a semi-automated sample preparation system (Kagan et al., *J. Clin. Ligand Assay*, 25:104-110(2002)). The CellSearch™ Epithelial Cell Kit consists of: ferrofluids coated with anti-EpCAM antibodies specific for epithelial cells; phycoerythrin-conjugated antibodies to cytokeratins 8, 18, and 19; an anti-CD45 antibody conjugated to allophycocyanin; DAPI dye; and buffers for washing, permeabilizing, and resuspending the cells. The protocol used in this example is also described in Allard et al., *Clin. Cancer Res.*, 10:6897-6904 (2004). The entire Veridex system can be used for CTC enumeration or, by removing the sample manually after isolation with the CellTracks® AutoPrep® System, can provide a method of isolation prior to analysis for pathway activation. The number of CTCs can be informative for algorithm development.

Veridex system—CTC enrichment followed by enumeration:
1) 7.5 ml of blood are mixed with 6 ml of buffer, centrifuged at 800×g for 10 minutes, and then placed on the CellTracks® AutoPrep® System.
2) After the instrument aspirates the supernatant, the instrument adds the ferrofluids.
3) The instrument performs the incubation and subsequent magnetic separation step.
4) Unbound cells and the remaining plasma are aspirated.
5) Staining reagents are added in conjunction with the permeabilization buffer for fluorescence staining
6) After incubation by the system, the cells are again separated magnetically and resuspended in the MagNest® cell presentation device.
7) The MagNest® cell presentation device is then placed on the CellTracks® Analyzer, a four-color semi-automated fluorescence microscope.
8) Images are captured that meet the Veridex defined criteria and are shown via a web-based browser for final manual selection.
9) Results of cell enumeration are expressed as the number of cells per 7.5 ml of blood.

Veridex system—CTC enrichment followed by an activation assay:
1) 7.5 ml of blood are mixed with 6 ml of buffer, centrifuged at 800×g for 10 minutes, and then placed on the CellTracks® AutoPrep® System.
2) After the instrument aspirates the supernatant, the instrument adds the ferrofluids.
3) The instrument performs the incubation and subsequent magnetic separation step.
4) Unbound cells and the remaining plasma are aspirated.
5) The sample is resuspended in 100 μl of stimulation buffer.

Veridex system—CEC and CEPC enrichment followed by an activation assay:
1) Veridex offers a CellSearch™ Endothelial Cell Kit utilizing capture with an anti-CD146 antibody. The CellSearch™ Endothelial Cell Kit is used in conjunction with the CellTracks® AutoPrep® System for blood sample preparation and the CellTracks® Analyzer to count and characterize CECs and CEPCs from whole blood. The protocol is the same as for the CellSearch™ Epithelial Cell Kit.

Sample preparation:
1) Enumeration: Peripheral blood from human subjects is drawn in the CellSave Preservative Tube according to manufacturer's instructions. The first 3-5 ml is discarded to avoid contamination with epithelial or endothelial cells released from the punctured vein.
2) Pathway analysis: Peripheral blood from human subjects is drawn in a siliconized tube containing 1 mg/ml EDTA. The first 3-5 ml is discarded to avoid contamination with epithelial or endothelial cells released from the punctured vein.

Manual Isolation of CSCs:

Evidence is building that tumors contain a small population of putative cancer stem cells with unique self-renewal and survival mechanisms (see, e.g., Sells, *Crit. Rev. Oncol. Hematol.*, 51:1-28 (2004); Reya et al., *Nature*, 414:105-111 (2001); Dontu et al., *Trends Endocrinol. Metal.*, 15:193-197 (2004); and Dick, *Nature*, 423:231-233 (2003)). Cancer stem cells (CSCs) may exist in a quiescent state for a long time, making them resistant to chemotherapeutic drugs which target dividing cells. This cancer-initiating population can be characterized for activation of self-renewal and survival pathways subject to targeted therapy for selective removal. Isolation procedures of CSCs have been described using adherence culture or magnetic microbeads. In this example, a protocol modified from that described in Cote et al., *Clin. Can. Res.*, 12:5615 (2006) is used.

Immunomagnetic CSC isolation—manual isolation followed by an activation assay:
1) Magnetic beads (Dynal AS; Oslo, Norway) are used. These beads are coated with a monoclonal antibody specific for either the CD34 or CD133 surface antigen.
2) Just prior to use, the pre-coated Dynabeads are washed once in an equal volume of PBS with BSA at 0.01%.
3) $1-10^7$ pre-coated Dynabeads are added to 3 ml of the sample.
4) The mixture is incubated for 60 minutes at 2-8° C. with gentle tilting and rotating.
5) The mixture is divided into 1 ml portions and each tube is placed in the magnetic separator (MPL-1 magnet) for at least 6 minutes.
6) The supernatant is discarded and the bead-bound cells are washed three times by resuspending in PBS with BSA at 0.01% followed by magnetic separation.

7) The sample is resuspended in 100 μl of stimulation buffer.

Sample preparation:
1) Bone marrow specimens are obtained from early breast cancer patients following patient informed consent.
2) Processing the bone marrow aspirates is performed as described in Bauer et al., *Clin. Can. Res.*, 6:3552-3559 (2000)). The mononuclear cell fraction containing any disseminated tumor cells is enriched by Ficoll-Hypaque density gradient centrifugation using a Beckman GS-6 centrifuge at 4000×g for 35 minutes and washed twice with PBS.

Cell Stimulation and Lysis of Isolated CTCs:
Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is incubated with Herceptin, Lapatinib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated CTCs are lysed using the following protocol:
1) Fresh lysis buffer is freshly prepared by mixing the reagents set forth in Table 3.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

TABLE 3

| Lysis Buffer Recipe (10 ml) | | | |
|---|---|---|---|
| Reagents | Stock conc. | Final conc. | Volume |
| 10% Triton X-100 | 10 | 1 | 1.00 |
| 1M Tris, pH 7.5 | 1 | 0.05 | 0.05 |
| 1M NaF | 1 | 0.05 | 0.05 |
| 5M NaCl | 5 | 0.1 | 0.20 |
| 2M B-glycerolphosphate | 1 | 0.05 | 0.50 |
| 0.1M Na$_3$VO$_4$ | 0.1 | 0.001 | 0.10 |
| 1 mg/ml pepstatin | 1 | 0.10 | |
| Complete mini protease | | | 1 tablet |
| 0.5M EDTA | 0.5 | 0.005 | 0.10 |
| | | Total (ml) | 3.00 |
| | | Water (ml) | 7.00 |

Cell Stimulation and Lysis of Isolated CECs and/or CEPCs:
VEGF is thought to promote survival by activating anti-apoptotic pathways in both CEPCs (Larrivee et al., *J. Biol. Chem.*, 278:22006-22013 (2003)) and mature CECs, which have been sloughed off the vessel wall (Solovey et al., *Blood*, 93:3824-3830 (1999)). VEGF may also stimulate the proliferation of CEPCs or mature CECs, although mature CECs seem to have only a limited proliferative capacity compared with CEPCs (Lin et al., *J. Clin. Invest.*, 105:71-77 (2000)). For these reasons, CECs and/or CEPCs are activated by incubation with VEGF family growth factors prior to lysis.

Cell stimulation:
1) The growth factors VEGF, FGF, PDGF, PIGF, and/or Ang, each at 100 nM, are added to the cells and incubated at 37° C. for 5 minutes.

Cell stimulation with drug treatment:
1) Sample is incubated with Avastin, Nexavar, Sutent, and/or Rapamycin analogs at therapeutically effective concentrations for 30 min. at 37° C.
2) Cells are then stimulated by adding factors VEGF, FGF, PDGF, PIGF, and/or Ang, each at 100 nM, and incubated at 37° C. for 5 minutes.

Cell stimulation with drug treatment (feedback loop):
1) Sample is incubated with Avastin, Nexavar, Sutent, and/or Rapamycin analogs at therapeutically effective concentrations for 30 min. at 37° C.
2) Cells are then stimulated by adding VEGF, FGF, PDGF, PIGF, and/or Ang, each at 100 nM, and incubated at 37° C. for 120 minutes.

Isolated CECs and/or CEPC cells are lysed using the following protocol:
1) Fresh lysis buffer is freshly prepared by mixing the reagents set forth in Table 3.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Cell Stimulation and Lysis of Isolated CSCs:
Stimulated cells:
1) Growth factors TGF-α (100 nM), Hrg (100 nM), and/or IGF (100 nM) are added to the cells and incubated at 37° C. for 5 minutes.

Stimulated cells with drug treatment:
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Stimulated cells with drug treatment (feedback loop):
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 120 minutes.

Isolated CSC cells are lysed using the following protocol:
1) Fresh lysis buffer is freshly prepared by mixing the reagents set forth in Table 3.
2) After the final wash, cells are re-suspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Example 2

Preparation of Tumor Cell Extracts from Tissue, Biopsy, or Primary Cultures

This example illustrates methods for isolating, stimulating, and lysing cells from tumor tissue or biopsy specimens. This example also illustrates methods for initiating, stimulating, and lysing primary cultures of tumor cells isolated from tissue, biopsy, or whole blood. Additional methods for isolating and culturing tumor cells from biological specimens for screening chemotherapeutic agents are described, e.g., in U.S. Pat. Nos. 5,728,541; 6,416,967; 6,887,680; 6,900,027; 6,933,129; and 7,112,415; and in U.S. Patent Publication Nos. 20040023375 and 20050202411. The cellular extracts prepared in accordance with this example can be used in the single detection or proximity assays described herein.

Isolation of Tumor Cells from Primary or Metastatic Tissues:
  Cell isolation and culture:
    1) Approximately 5-100 mg non-necrotic, non-contaminated tumor tissue are harvested surgically and placed into 100 ml bottle containing sterile cell culture media (e.g., RMPI-1640 with 10% FBS and antibiotics).
    2) Samples can be stored or shipped at room temperature within 72 hours of extraction.
    3) Samples are rinsed three times in cell culture media.
    4) The tissue is minced into small pieces with a scalpel and then disaggregated into a cell suspension by passing through a fine wire mesh.
    5) Alternatively, minced tissue is treated with a cocktail containing 0.25% Collagenase II and 0.001% DNase diluted in serum-free cell culture media containing antibiotics. Incubation is for 15-20 min with gentle agitation. Enzymes are removed after treatment by washing 3 times with cell culture media.
    6) Cell concentration is adjusted to $10^6$/ml and cells are seeded into 6-well plates and allowed to settle overnight. The following day, the cells are trypsinized and re-seeded into microtiter plates for stimulation with ligands and/or inhibition with targeted drugs.

Cell Stimulation and Lysis of Cells from Disaggregated Tumors:
  Cell stimulation:
    1) Growth factors TGF-α (100 nM), Hrg (100 nM), and/or IGF (100 nM) are added to the cells and incubated at 37° C. for 5 minutes.
  Cell stimulation with drug treatment:
    1) Sample is incubated with Herceptin, Lapatinib, Tarceva, and/or Rapamycin analogs at therapeutically effective concentrations for 30 min. at 37° C.
    2) Cells are then stimulated by adding factors TGF-α (100 nM), Hrg (100 nM), and/or IGF (100 nM) and incubated at 37° C. for 5 minutes.
  Cell stimulation with drug treatment (feedback loop):
    1) Sample is incubated with Herceptin, Lapatinib, Tarceva, and/or Rapamycin analogs at therapeutically effective concentrations for 30 min. at 37° C.
    2) Cells are then stimulated by TGF-α (100 nM), Hrg (100 nM), and/or IGF (100 nM) and incubated at 37° C. for 120 minutes.
  Stimulated cells are lysed using the following protocol:
    1) Fresh lysis buffer is freshly prepared by mixing the reagents set forth in Table 3 above.
    2) After the final wash, cells are resuspended on ice in 100 μl of chilled buffer.
    3) Incubation is performed on ice for 30 minutes.
    4) The mixture is spun in a microfuge at maximum speed for 10 minutes to separate the beads from the lysate.
    5) The lysate is transferred to a new tube for assay or storage at −80° C.

Isolation of Tumor Cells from Biopsy Specimens:
  Cell isolation and culture:
    1) Core biopsies are extracted surgically (2 cores for 14 gauge needles, 3 cores for 16 gauge needles, and 4 cores for 18 gauge needles, with 1-2 biopsies for vacuum-assisted biopsies) and placed into a 10 ml sterile vial containing cell culture media as for tumor specimens.
    2) Samples can be stored or shipped at room temperature within 72 hours of extraction.
    3) Cellular material from core biopsies is disaggregated into a cell suspension by passing through a fine wire mesh.
    4) Alternatively, biopsies may be treated with a cocktail containing 0.25% Collagenase II and 0.001% DNase diluted in cell culture media containing antibiotics. Incubation is for 15-20 min with gentle agitation. Enzymes are removed after treatment by washing 3 times with cell culture media.
    5) Cell concentration is adjusted to $10^6$/ml and cells are seeded into 6-well plates and allowed to settle overnight. The following day, the cells are trypsinized and re-seeded into microtiter plates for stimulation with ligands and/or inhibition with targeted drugs.

Cell Stimulation and Lysis of Cells from Biopsies:
  Cell stimulation:
    1) Growth factors TGF-α (100 nM), Hrg (100 nM), and/or IGF (100 nM) are added to the cells and incubated at 37° C. for 5 minutes.
  Cell stimulation with drug treatment:
    1) Sample is incubated with Herceptin, Lapatinib, Tarceva, and/or Rapamycin analogs at therapeutically effective concentrations for 30 min. at 37° C.
    2) Cells are then stimulated by adding factors TGF-α (100 nM), Hrg (100 nM), and/or IGF (100 nM) and incubated at 37° C. for 5 minutes.
  Cell stimulation with drug treatment (feedback loop):
    1) Sample is incubated with Herceptin, Lapatinib, Tarceva, and/or Rapamycin analogs at therapeutically effective concentrations for 30 min. at 37° C.
    2) Cells are then stimulated by TGF-α (100 nM), Hrg (100 nM), and/or IGF (100 nM) and incubated at 37° C. for 120 minutes.
  Stimulated cells are lysed using the following protocol:
    1) Fresh lysis buffer is freshly prepared by mixing the reagents set forth in Table 3 above.
    2) After the final wash, cells are resuspended on ice in 100 μl of chilled buffer.
    3) Incubation is performed on ice for 30 minutes.
    4) The mixture is spun in a microfuge at maximum speed for 10 minutes to separate the beads from the lysate.
    5) The lysate is transferred to a new tube for assay or storage at −80° C.

Initiation of Primary Cultures from Tumor Cells Isolated from Tissue, Biopsy, or Whole Blood:
  Cell culture:
    1) Tumor cells isolated from tissue, biopsy, or whole blood as described above are cultured in small sterile flasks (e.g., T-25), Petri dishes (e.g., 10 mm), or plates (e.g., 24-well plates) depending on the number of isolated tumor cells.
    2) Incubation is done in cell culture media (e.g., RMPI-1640 with 2% FBS and antibiotics) in a humidified 37° C. incubation supplemented with 5% $CO_2$. Over time, cells form a monolayer on the bottom of the vessel and begin to divide. When the cells are close to confluence, they are trypsinized and re-seeded into microtiter plates for stimulation with ligands and/or inhibition with targeted drugs.

Cell Stimulation and Lysis of Primary Cultures from Tumor Cells Isolated from Tissue, Biopsy, or Whole Blood:
  Cell stimulation:
    1) Growth factors TGF-α (100 nM), Hrg (100 nM), and/or IGF (100 nM) are added to the cells and incubated at 37° C. for 5 minutes.

Cell stimulation with drug treatment:
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is incubated with Herceptin, Lapatinib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated cells are lysed using the following protocol:
1) Fresh lysis buffer is freshly prepared by mixing the reagents set forth in Table 3 above.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Example 3

Single Detection Microarray ELISA with Tyramide Signal Amplification

This example illustrates a multiplex, high-throughput, single detection microarray ELISA having superior dynamic range that is suitable for analyzing the activation states of signal transduction molecules in rare circulating cells:
1) Capture antibody was printed on a 16-pad FAST slide (Whatman Inc.; Florham Park, N.J.) with a 2-fold serial dilution.
2) After drying overnight, the slide was blocked with Whatman blocking buffer.
3) 80 μl of cell lysate was added onto each pad with a 10-fold serial dilution. The slide was incubated for two hours at room temperature.
4) After six washes with TBS-Tween, 80 μl of biotin-labeled detection antibody (e.g., a monoclonal antibody recognizing p-EGFR or a monoclonal antibody recognizing EGFR regardless of activation state) was incubated for two hours at room temperature.
5) After six washes, streptavidin-labeled horseradish peroxidase (SA-HRP) was added and incubated for 1 hour to allow the SA-HRP to bind to the biotin-labeled detection antibody.
6) For signal amplification, 80 μl of biotin-tyramide at 5 μg/ml was added and reacted for 15 minutes. The slide was washed six times with TBS-Tween, twice with 20% DMSO/TBS-Tween, and once with TBS.
7) 80 μl of SA-Alexa 555 was added and incubated for 30 minutes. The slide was then washed twice, dried for 5 minutes, and scanned on a microarray scanner (Perkin-Elmer, Inc.; Waltham, Mass.).

Example 4

Proximity Dual Detection Microarray ELISA with Tyramide Signal Amplification

This example illustrates a multiplex, high-throughput, proximity dual detection microarray ELISA having superior dynamic range that is suitable for analyzing the activation states of signal transduction molecules in rare circulating cells:
1) Capture antibody was printed on a 16-pad FAST slide (Whatman Inc.) with a serial dilution ranging from 1 mg/ml to 0.004 mg/ml.
2) After drying overnight, the slide was blocked with Whatman blocking buffer.
3) 80 μl of A431 cell lysate was added onto each pad with a 10-fold serial dilution. The slide was incubated for two hours at room temperature.
4) After six washes with TBS-Tween, 80 μl of detection antibodies for the proximity assay diluted in TBS-Tween/2% BSA/1% FBS was added to the slides. The detection antibodies used were: (1) an anti-EGFR monoclonal antibody that was directly conjugated to glucose oxidase (GO); and (2) a monoclonal antibody recognizing phosphorylated EGFR that was directly conjugated to horseradish peroxidase (HRP). The incubation was for 2 hours at room temperature.
5) Alternatively, the detection step utilized a biotin-conjugate of the monoclonal antibody recognizing phosphorylated EGFR. In these instances, after six washes an additional sequential step of incubation with streptavidin-HRP for 1 hour was included.
6) Alternatively, the detection step utilized an oligonucleotide-mediated glucose oxidase (GO) conjugate of the anti-EGFR antibody. Either the directly conjugated or the biotin-steptavidin (SA) linked conjugate of HRP to the phosphorylated EGFR antibody was used.
7) For signal amplification, 80 μl of biotin-tyramide at 5 μg/ml was added and reacted for 15 min. The slide was washed six times with TBS-Tween, twice with 20% DMSO/TBS-Tween, and once with TBS.
8) 80 μl of SA-Alexa 555 was added and incubated for 30 min. The slide was then washed twice, dried for 5 minutes, and scanned on a microarray scanner (Perkin-Elmer, Inc.).

Figure 2:
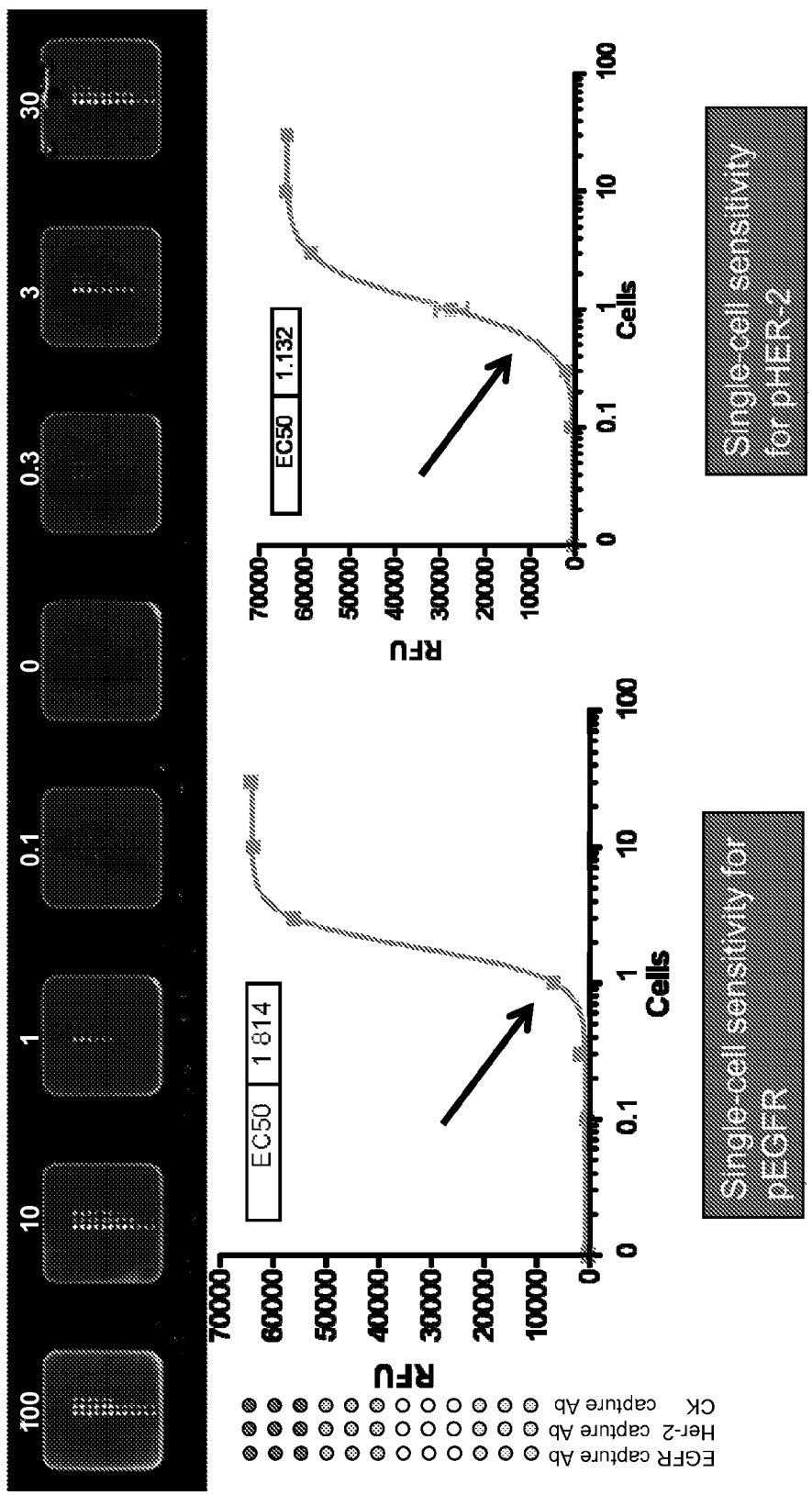
FIG. 2 shows one embodiment of the present invention in which the proximity assays described herein detected phosphorylated EGFR (pEGFR) and phosphorylated HER-2 (pHER-2) with single cell sensitivity.
Figure 3:
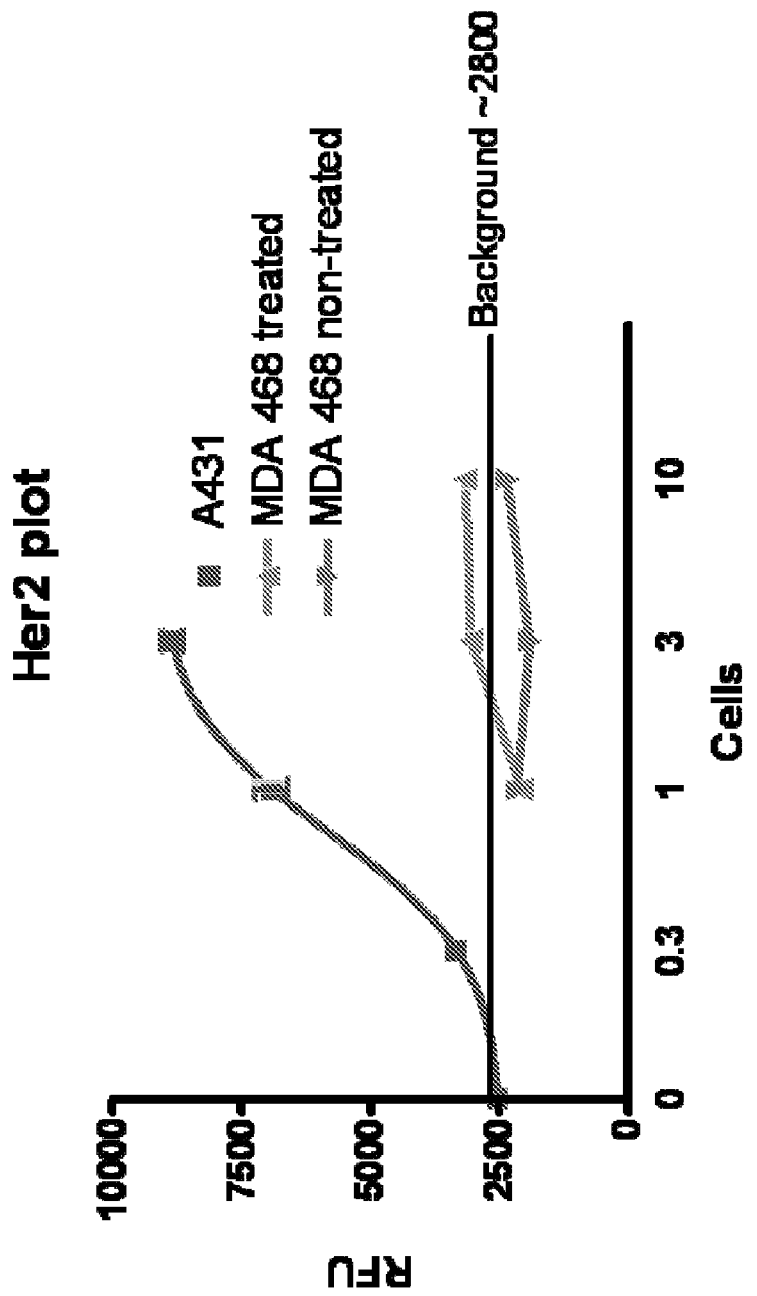
FIG. 3 shows that the proximity assays described herein resulted in highly specific assays for the detection of HER-2 at the single cell level only in cells expressing HER-2.

FIG. 2 illustrates one embodiment of the present invention in which the proximity assays described herein detected phosphorylated EGFR (pEGFR) and phosphorylated HER-2 (pHER-2) with single cell sensitivity. FIG. 3 shows that the proximity assays described herein resulted in highly specific assays for the detection of HER-2 at the single cell level only in cells expressing HER-2.

Example 5

Generation of Activation Profiles for Drug Selection

Figure 4:
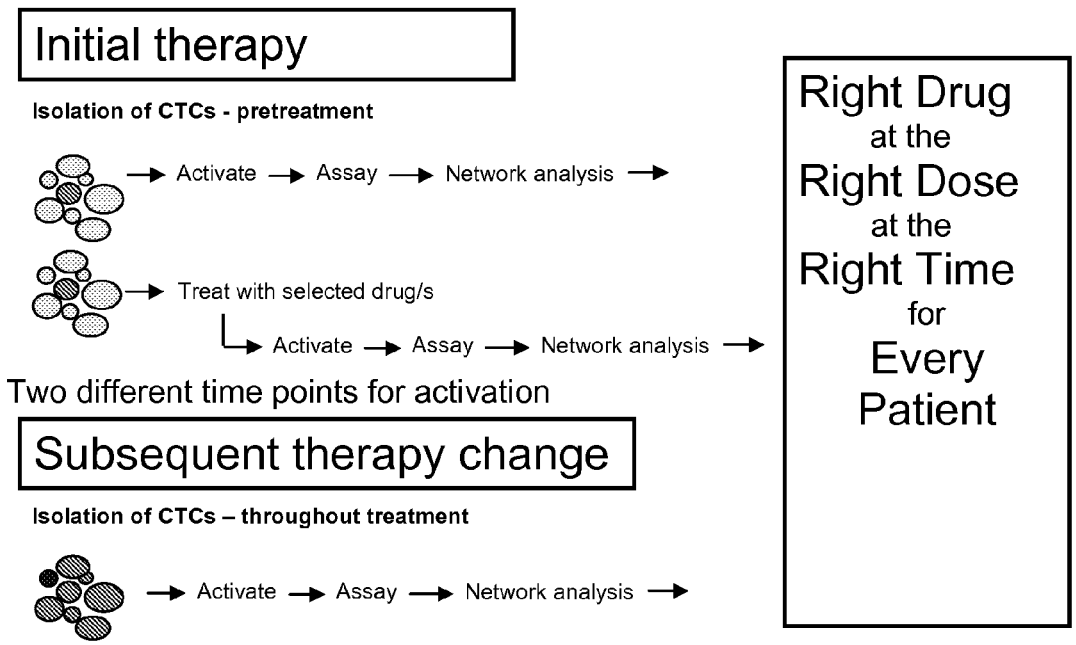
FIG. 4 shows schematically the application of the addressable arrays of the invention for drug selection throughout the course of cancer treatment.

The methods and compositions of the present invention can be applied for drug selection for cancer treatment. A typical protocol entails the generation of two profiles, a reference activation profile and a test activation profile, which are then compared to determine the efficacy of a particular drug treatment regimen (see, FIG. 4).

Reference Activation Profile

To derive a reference activation profile, a blood sample is obtained from a patient having a specific type of cancer (e.g., breast tumor) prior to anticancer drug treatment. Rare circulating cells derived from the cancerous tumor are isolated from the blood sample using, e.g., immunomagnetic separation techniques as described in greater detail herein. The isolated circulating cells can be stimulated in vitro with one or more growth factors. The stimulated cells are then lysed to produce a cellular extract. The cellular extract is applied to an addressable array containing a dilution series of a panel of capture antibodies specific for signal transduction molecules whose activation states may be altered in the patient's type of cancer. Single detection or proximity assays are performed using the appropriate detection antibodies (e.g., activation state-independent antibodies and/or activation state-dependent antibodies) to determine the activation state of each signal transduction molecule of interest. The "Pathway Selection" table shown in Table 2 is particularly useful for selecting which activation states to detect based upon the patient's type of cancer. For example, one patient may have a type of cancer that displays the activation states of the EGFR pathway set forth in "Pathway 1" of Table 2. Alternatively, another patient may have another type of cancer that displays the activation states of the EGFR pathway set forth in "Pathway 2" of Table 2. A reference activation profile is thus generated providing the activation states of signal transduction molecules in the patient's cancer in the absence of any anticancer drugs.

Test Activation Profile

To obtain a test activation profile, a second blood sample is obtained from the patient having the specific type of cancer (e.g., breast tumor) either prior to anticancer drug treatment or after administration of an anticancer drug (e.g., at any time throughout the course of cancer treatment). Rare circulating cells derived from the cancerous tumor are isolated from the blood sample. If isolated cells are obtained from a patient who has not received treatment with an anticancer drug, the isolated cells are incubated with anticancer drugs which target one or more of the activated signal transduction molecules determined from the reference activation profile described above. The "Drug Selection" table (Table 1) is particularly useful for selecting appropriate anticancer drugs that are either approved or in clinical trials which inhibit specific activated target signal transduction molecules. For example, if it is determined from the reference activation profile that EGFR is activated, then the cells can be incubated with one or more of the drugs listed in column "A" or "B" of Table 1. The isolated cells can then be stimulated in vitro with one or more growth factors. The isolated cells are then lysed to produce a cellular extract. The cellular extract is applied to the addressable array and proximity assays are performed to determine the activation state of each signal transduction molecule of interest. A test activation profile for the patient is thus generated providing the activation states of signal transduction molecules in the patient's cancer in the presence of specific anticancer drugs.

Drug Selection

The anticancer drugs are determined to be suitable or unsuitable for treatment of the patient's cancer by comparing the test activation profile to the reference activation profile. For example, if drug treatment causes most or all of the signal transduction molecules to be substantially less activated than in the absence of the drugs, e.g., a change from strong activation without the drugs to weak or very weak activation with the drugs, then the treatment is determined to be suitable for the patient's cancer. In such instances, treatment is either initiated with the suitable anticancer drug in a patient who has not received drug therapy or subsequent treatment is continued with the suitable anticancer drug in a patient already receiving the drug. However, if the drug treatment is deemed unsuitable for treatment of the patient's cancer, different drugs are selected and used to generate a new test activation profile, which is then compared to the reference activation profile. In such instances, treatment is either initiated with a suitable anticancer drug in a patient who has not received drug therapy or subsequent treatment is changed to a suitable anticancer drug in a patient currently receiving the unsuitable drug.

Example 6

Addressable Arrays for Analysis of Activated Receptor Tyrosine Kinases

FIG. 5 illustrates an exemplary addressable receptor tyrosine kinase array of the invention. As discussed herein, receptor tyrosine kinases are key components of many signal transduction pathways involved in cell proliferation. For example, the ErbB family of receptor tyrosine kinases has four family members and plays an important role in fundamental cell processes like cell proliferation, differentiation, and survival. This family of receptor tyrosine kinases has been reported to be overexpressed in a number of different cancers and is associated with worse clinical outcome. On growth factor binding, ErbB1/EGFR, ErbB3/HER-3, and ErbB4/HER-4 homo- and hetero-dimerize to activate a number of different signaling pathways. ErbB2/HER-2 does not bind to a growth factor and is the preferred hetero-dimerization partner for all three family members. ErbB2 can also homo-dimerize when overexpressed and activate signaling pathways. Homo- or hetero-dimerization of ErbB family results in trans-phosphorylation. Auto- or trans-phosphorylation relieves the inhibitory conformation of receptor tyrosine kinases, enabling full kinase activation and at the same time creates binding sites for numerous SH2-containing signaling molecules, such as Src, Shc SHP-1, SHEP-1, and PI3K. Adapter proteins or signaling proteins like Shc, Grb2, or PI3K are recruited to the phosphorylated receptors. Phosphorylation of the adapter proteins results in activation of the MAPK and Akt pathways. MAPK pathway activation can be evaluated by determining the phosphorylation status of Erk and Rsk, while PI3K pathway activation can be evaluated by determining the phosphorylation status of Akt and p70S6K.

Thus, the addressable array shown in FIG. 5 allows one to not only determine the expression of the ErbB family of receptor tyrosine kinases, but also their activation status. Both MAPK and PI3K/Akt pathway activation can also be studied on the addressable chip. In addition, the expression and/or activation status of nuclear hormone receptors such as ER (estrogen receptor) and PR (progesterone receptor), and other proteins such as NCOR (nuclear receptor corepressor), AIB1 (amplified in breast cancer-1), IGF-IR, cMET, Ki67, and TOPO II can be studied on the addressable chip. Another feature of the chip is the presence of internal controls to determine the tumor or tumor-associated cell (CEC's, CEP's, pericytes, etc.) content and non-specific IgG to determine any non-specific binding.

Example 7

Addressable Arrays for Analysis of Signal Transduction Pathways in Angiogenesis

Figure 7:
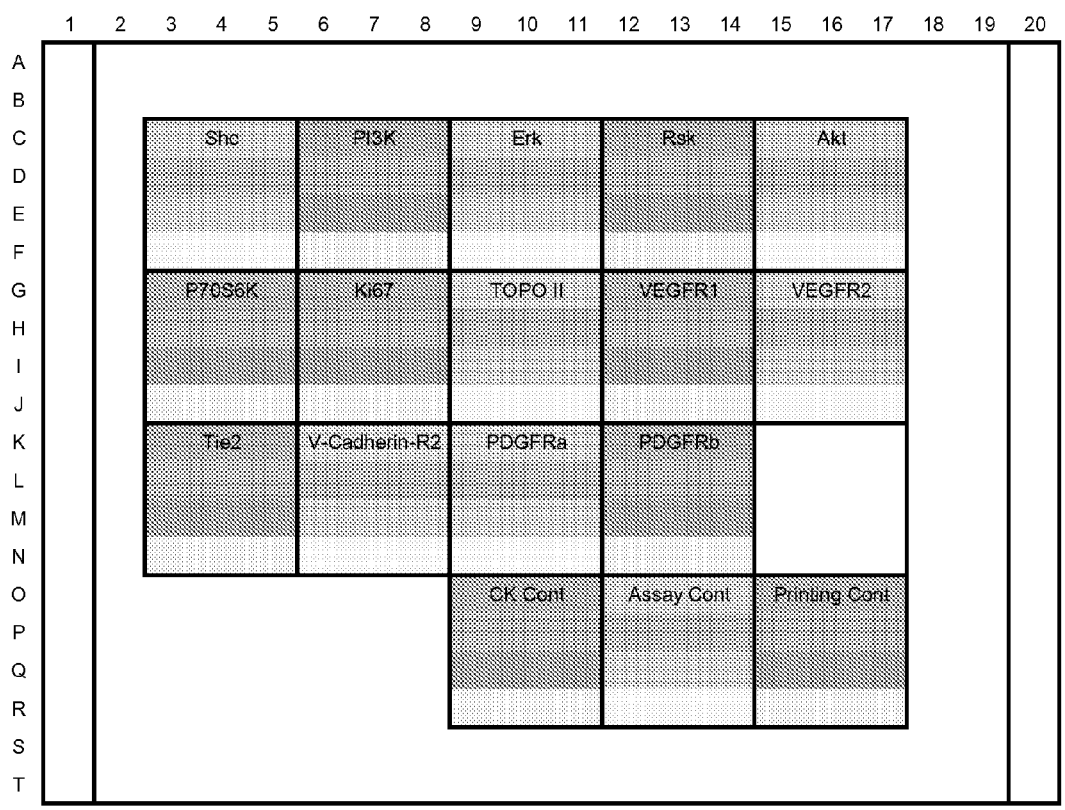
FIG. 7 shows a schematic example of an alternative addressable array comprising dilutions of antibodies to components of signal transduction pathways activated in tumor angiogenesis. Antibodies are plated in triplicate in four different dilutions on the addressable array.

FIGS. 6 and 7 illustrate the configuration of addressable arrays for determining the activation state of signal transduction components involved in angiogenesis. As described herein, tumor angiogenesis is critical for the growth of many solid tumors. Among the key signal transduction molecules arrayed include members of the VEGFR, FGFR, and TIE family of receptor tyrosine kinases, which are expressed predominantly on endothelial cells. PDGFR is typically expressed on pericytes. The expression and activation status of these receptors is critical in determining the predominant mechanism of angiogenesis in individual tumor specimens. Growth factors like VEGF and PIGF bind to VEGFR-1 and VEGFR-2 and initiate homo- and hetero-dimerization.

Dimerization is followed by phosphorylation of these receptors, which in turn is followed by activation of the MAPK and PI3K/Akt signaling pathways. FGFR, TIE, and PDGFR receptors are also activated in a similar manner. Auto- or trans-phosphorylation relieves the inhibitory conformation of receptor tyrosine kinases, enabling full kinase activation and at the same time creates binding sites for numerous SH2-containing signaling molecules, such as Src, Shc, SHP-1, V-cadherin, SHEP-1, and PI3K. Adapter proteins or signaling proteins like Shc, Grb2, or PI3K are recruited to the phosphorylated receptors. Phosphorylation of the adapter proteins results in activation of the MAPK and Akt pathways. MAPK pathway activation can be evaluated by determining the phosphorylation status of Erk and Rsk, while PI3K pathway activation can be evaluated by determining the phosphorylation status of Akt and p70S6K.

Thus, addressable angiogenesis chips, such as those shown in FIGS. 6 and 7, allow one to not only determine the expression of all the signal transduction components involved in angiogenesis in a patient sample, but also their activation status. Both MAPK and PI3K/Akt pathway activation can also be studied on the addressable chip. The chip has internal controls to determine the tumor or tumor-associated cell (CEC's, CEP's, pericytes, etc.) content and non-specific IgG to determine any non-specific binding.

FIGS. 8 and 9 show combined addressable arrays of the invention for determining the expression and/or activation state of the ErbB family of receptor tyrosine kinases as well as signal transduction components involved in angiogenesis. In addition, the expression and/or activation status of nuclear hormone receptors such as ER (estrogen receptor) and PR (progesterone receptor), and other proteins such as NCOR (nuclear receptor corepressor), AIB1 (amplified in breast cancer-1), IGF-IR, cMET, Ki67, and TOPO II can be studied on these combined addressable chips. Another feature of these chips is the presence of internal controls to determine the tumor or tumor-associated cell (CEC's, CEP's, pericytes, etc.) content and non-specific IgG to determine any non-specific binding.

Example 8

Selection of Patients for Treatment of Breast Cancer

A major challenge of cancer treatment is the selection of therapeutic regimens that maximize efficacy and minimize toxicity for a given patient. A related challenge lies in the attempt to provide accurate diagnostic, prognostic, and predictive information.

At present, tumors are generally classified under the tumor-node-metastasis (TNM) system. This system uses the size of the tumor, the presence or absence of tumor in regional lymph nodes, and the presence or absence of distant metastases to assign a stage to the tumor according to guidelines published in the AJCC Cancer Staging Manual (Lippincott, 5th ed., pp. 171-180 (1997)). The assigned stage is used as a basis for selection of appropriate therapy and for prognostic purposes. In addition to the TNM parameters, morphologic appearance is used to further classify tumors into tumor types and thereby aid in selection of appropriate therapy. However, this approach has serious limitations. For example, tumors with similar histopathological appearance can exhibit significant variability in terms of clinical course and response to therapy. In addition, some tumors are rapidly progressive while others are not. Furthermore, some tumors respond readily to hormonal therapy or chemotherapy while others are resistant.

Assays for cell surface markers, e.g., using immunohistochemistry, have provided means for categorizing certain tumor types into subclasses. For example, one factor considered in prognosis and treatment decisions for breast cancer is the presence or absence of the estrogen receptor (ER) in tumor samples. ER-positive breast cancers typically respond much more readily to hormonal therapies such as tamoxifen, which acts as an anti-estrogen in breast tissue, than ER-negative tumors. Though useful, these analyses only in part predict the clinical behavior of breast tumors. There is phenotypic diversity present in cancers that current diagnostic tools fail to detect. As a consequence, there is still much controversy over how to stratify patients amongst potential treatments in order to optimize outcome (e.g., for breast cancer, see "NIH Consensus Development Conference Statement: Adjuvant Therapy for Breast Cancer, Nov. 1-3, 2000", *J. Nat. Cancer Inst. Monographs,* 30:5-15 (2001); and Di Leo et al., *Int. J. Clin. Oncol.,* 7:245-253 (2002)).

The present invention encompasses the realization that signaling pathways can be used to provide new insights into the biological etiology of cancer and disease progression. The present invention further provides methods for treatment of cancers with various activated signaling pathways using a personalized therapeutic regimen.

Three different molecular markers are currently used to define four different subclasses of breast cancer with major therapeutic implications. The three markers are ER, PR, and HER-2/ErbB2. The four major subclasses are as follows:
1. ER+/PR+/ErbB2−
2. ER+/ErbB2+
3. ER−/ErbB2+
4. ER−/PR−/ErbB2−

One current theory divides breast cancer into five molecular subtypes: luminal A; luminal B; basal-like; HER-2/neu-positive; and normal breast-like (see, e.g., Carey et al., *JAMA,* 295:2492-2502 (2006); Fan et al., *N. Engl. J. Med.,* 355:560-569 (2006); Hannemann et al., *British J Cancer,* 95:1334-1341 (2006); Potemski et al., *Oncology,* 69:478-485 (2005)). Much of what is known to date about these subtypes is directly related to those characteristics that are already well understood, such as hormone receptor and HER-2/neu status.

Estrogen plays an important role in breast cancer pathogenesis, and selective interference of the estrogen/ER-mediated signaling cascade is the most effective means of treating ER-positive breast cancer patients. ER regulates growth and differentiation in both normal and malignant breast cells. Expression of functional ER and/or progesterone receptors (PR) is essential for a tumor to be responsive to antihormonal therapies ("hormone-responsive"), and multiple studies have demonstrated that expression of ER is strongly predictive for response to antihormonal therapies, although its expression is only weakly prognostic. ER does not act alone to stimulate tumor growth; rather, a complex interaction network operates to ensure the viability of cancer cells. Understanding this network provides scientific rationale for the selection of targeted therapies.

The exemplary patient profiles shown below in Tables 4-22 illustrate how an analysis of the pathways active in circulating tumor cells (CTCs) from blood or cancer cells obtained from a needle biopsy can be used to help physicians decide upon an effective course of treatment for a breast tumor, e.g., neoadjuvant treatment prior to surgery to reduce the size of the breast tumor or treatment in patients with locally recurrent or metastatic breast cancer. In brief, the activation levels of different components of the ErbB and nuclear hormone receptor pathways in CTCs or biopsy-derived cancer cells can be determined in the presence or absence of different combinations of test therapeutic agents.

TABLE 4

Patient 4001: (ER+/PR+/ErbB2−)

| Receptor | Expression | Activation (Level of Phosphorylation) | Treatment with Tamoxifen |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | High |
| Progesterone Receptor | High | | Medium |
| IGF-1R | Low | Weak | Weak |
| ErbB1 | Low | Weak | Weak |
| ErbB2 | Low | Weak | Weak |
| ErbB3 | Low | Weak | Weak |
| ErbB4 | Low | Weak | Weak |
| PTEN | Medium | Medium | Medium |
| Shc | | Weak | Weak |
| PI3K | | Weak | Weak |
| Erk | | Medium | Weak |
| Rsk | | Medium | Weak |
| Akt | | Medium | Weak |
| P70S6K | | Medium | Weak |
| Ki67 | Medium | | Weak |
| TOPO II | Medium | | Medium |

Patient (premenopausal woman and node negative) was biopsied or CTCs were isolated from blood. Analysis of her tumor cells revealed high expression and activation of ER/PR. The patient was treated with tamoxifen. The patient responded and on re-biopsy had the protein profile as shown above. Thus, a patient with the above protein profile responds to tamoxifen. ER is thought to recruit the corepressor protein NCOR in the presence of antagonists such as tamoxifen, and this recruitment is thought to be essential for full antagonist activity.

TABLE 5

Patient 4002: (ER+/PR−/ErbB2−)

| Receptor | Expression | Activation (Level of Phosphorylation) | Treatment with Tamoxifen + Chemotherapy |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | High |
| Progesterone Receptor | Low | | Weak |
| IGF-1R | Low | Weak | Weak |
| ErbB1 | Low | Weak | Weak |
| ErbB2 | Low | Weak | Weak |
| ErbB3 | Low | Weak | Weak |
| ErbB4 | Low | Weak | Weak |
| Shc | | Weak | Weak |
| PI3K | | Weak | Weak |
| Erk | | Medium | Weak |
| Rsk | | Medium | Weak |
| Akt | | Medium | Weak |
| P70S6K | | Medium | Weak |
| Ki67 | High | | Weak |
| TOPO II | High | | High |

Patient (premenopausal woman and node negative) was biopsied or CTCs were isolated from blood. Analysis of her tumor cells revealed high expression and activation of ER and high Ki67 expression. The patient was treated with tamoxifen+chemotherapy. The patient responded and on re-biopsy had the protein profile as shown above. Thus, a patient with the above protein profile responds to tamoxifen+chemotherapy. ER is thought to recruit the corepressor protein NCOR in the presence of antagonists such as tamoxifen, and this recruitment is thought to be essential for full antagonist activity.

TABLE 6

Patient 4003: (ER+/PR+/ErbB2−)

| Receptor | Expression | Activation (Level of Phosphorylation) | Treatment with Tamoxifen + Chemotherapy |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | High |
| Progesterone Receptor | High | | Weak |
| IGF-1R | Low | Weak | Weak |
| ErbB1 | Low | Weak | Weak |
| ErbB2 | Low | Weak | Weak |
| ErbB3 | Low | Weak | Weak |
| ErbB4 | Low | Weak | Weak |
| Shc | | Weak | Weak |
| PI3K | | Weak | Weak |
| Erk | | Medium | Weak |
| Rsk | | Medium | Weak |
| Akt | | Medium | Weak |
| P70S6K | | Medium | Weak |
| Ki67 | High | | Weak |
| TOPO II | High | | High |

Patient (premenopausal woman and node positive) was biopsied or CTCs were isolated from blood. Analysis of her tumor cells revealed high expression and activation of ER/PR. The patient was treated with tamoxifen+chemotherapy. The patient responded and on re-biopsy had the protein profile as shown above. Thus, a patient with the above protein profile responds to tamoxifen+chemotherapy. ER is thought to recruit the corepressor protein NCOR in the presence of antagonists such as tamoxifen, and this recruitment is thought to be essential for full antagonist activity.

TABLE 7

Patient 4004: (ER+/PR+/ErbB2−)

| Receptor | Expression | Activation (Level of Phosphorylation) | Treatment with Aromatase Inhibitor |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | High | | Medium |
| IGF-1R | Low | Weak | Weak |
| ErbB1 | Low | Medium | Weak |
| ErbB2 | Low | Weak | Weak |

TABLE 7-continued

Patient 4004: (ER+/PR+/ErbB2−)

| Receptor | Expression | Activation (Level of Phosphorylation) | Treatment with Aromatase Inhibitor |
|---|---|---|---|
| ErbB3 | Low | Weak | Weak |
| ErbB4 | Low | Weak | Weak |
| Shc | | Weak | Weak |
| PI3K | | Weak | Weak |
| Erk | | Medium | Weak |
| Rsk | | Medium | Weak |
| Akt | | Medium | Weak |
| P70S6K | | Medium | Weak |
| Ki67 | Medium | | Weak |
| TOPO II | Low | | |

Patient (pre- or postmenopausal woman) was biopsied or CTCs were isolated from blood. Analysis of the tumor cells revealed high expression and activation of ER/PR along with some activation of ErbB 1 via MISS (ER activation in cytoplasm with resultant cross-talk activation of ErbB1). The patient was treated with an aromatase inhibitor to shut down all ER-related activity. The patient responded and on re-biopsy had the protein profile as shown above. Thus, a patient with the above protein profile responds to aromatase inhibitors.

TABLE 8

Patient 4005: (ER+/PR+/ErbB2−)

| Receptor | Expression | Activation (Level of Phosphorylation) | Treatment with Aromatase Inhibitor + Chemotherapy |
|---|---|---|---|
| ER | High | Medium | |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | High | | Medium |
| IGF-1R | Low | Weak | Weak |
| ErbB1 | Low | Medium | Weak |
| ErbB2 | Low | Weak | Weak |
| ErbB3 | Low | Weak | Weak |
| ErbB4 | Low | Weak | Weak |
| Shc | | Weak | Weak |
| PI3K | | Weak | Weak |
| Erk | | Medium | Weak |
| Rsk | | Medium | Weak |
| Akt | | Medium | Weak |
| P70S6K | | Medium | Weak |
| Ki67 | High | | Weak |
| TOPO II | High | | |

Patient (pre- or postmenopausal woman) was biopsied or CTCs were isolated from blood. Analysis of the tumor cells revealed high expression and activation of ER/PR along with some activation of ErbB 1 via MISS (ER activation in cytoplasm with resultant cross-talk activation of ErbB1). The patient was treated with an aromatase inhibitor+chemotherapy to shut down all ER-related activity. The patient responded and on re-biopsy had the protein profile as shown above. Thus, a patient with the above protein profile responds to aromatase inhibitor+chemotherapy.

TABLE 9

Patient 4006: (ER+/PR−/ErbB2−)

| Receptor | Expression | Activation (Level of Phosphorylation) | Treatment with Aromatase Inhibitor OR Tamoxifen + Chemotherapy |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | Low | Medium | Weak |
| ErbB2 | Low | Weak | Weak |
| ErbB3 | Low | Weak | Weak |
| ErbB4 | Low | Weak | Weak |
| Shc | | Weak | Weak |
| PI3K | | Weak | Weak |
| Erk | | Medium | Weak |
| Rsk | | Medium | Weak |
| Akt | | Medium | Weak |
| P70S6K | | Medium | Weak |
| Ki67 | High | | Weak |

Patient (pre- or postmenopausal woman) was biopsied or CTCs were isolated from blood. Analysis of the tumor cells revealed high expression and activation of ER (PR negative tumors) along with some activation of ErbB1 via MISS (ER activation in cytoplasm with resultant cross-talk activation of ErbB1). The patient was treated with an aromatase inhibitor+chemotherapy to shut down all ER-related activity. The patient responded and on re-biopsy had the protein profile as shown above. Thus, a patient with the above protein profile responds to aromatase inhibitor+chemotherapy.

Table 10 provides an example of a patient with locally recurrent or metastatic breast cancer who has relapsed on endocrine therapy and/or chemotherapy. At least 3 weeks had elapsed since the patient received adjuvant chemotherapy and hormonal therapy for the locally recurrent or metastatic breast cancer.

TABLE 10

Patient 4007: (ER+/PR+/ErbB2−)

| Receptor | Expression | Activation (Level of Phosphorylation) | Treatment with Tamoxifen or Aromatase Inhibitor + Taxane + Avastin ® |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | High | | Medium |
| IGF-1R | Low | Weak | Weak |
| ErbB1 | Low | Medium | Weak |
| ErbB2 | Low | Weak | Weak |
| ErbB3 | Low | Weak | Weak |
| ErbB4 | Low | Weak | Weak |
| Shc | | Weak | Weak |
| PI3K | | Weak | Weak |
| Erk | | Medium | Weak |

TABLE 10-continued

| | | |
|---|---|---|
| Rsk | Medium | Weak |
| Akt | Medium | Weak |
| P70S6K | Medium | Weak |
| Ki67 | High | Weak |

Endothelial cells:

| Receptor | Expression | Activation (Level of hosphorylation) | Activation with Avastin ® |
|---|---|---|---|
| VEGFR2 | Medium | Strong | Weak |
| VEGFR1 | Medium | Strong | Weak |
| Tie 2 | Low | Weak | Weak |
| V-Cadherin-R2 complex | Null | Medium | Weak |
| Shc | | Strong | Weak |
| PI3K | | Strong | Weak |
| Erk | | Strong | Weak |
| Rsk | | Strong | Weak |
| Akt | | Strong | Weak |
| P70S6K | | Strong | Weak |

Patient (pre- or postmenopausal woman) with locally recurrent or metastatic breast cancer was biopsied or CTCs were isolated from blood. Analysis of her tumor cells and endothelial cells revealed high expression and activation of ER/PR along with some activation of ErbB1 via MISS (ER activation in cytoplasm with resultant cross-talk activation of ErbB1) as well as VEGFR2 activation. The patient was treated with an aromatase inhibitor+chemotherapy+Avastin® to shut down all ER- and VEGFR2-related activity. The patient responded and on re-biopsy had the protein profile as shown above. Thus, a patient with the above protein profile responds to the combination of an aromatase inhibitor+chemotherapy+Avastin®.

TABLE 11

Patient 4008: (High AIB1; ER+/PR+/ErbB2−)

| Receptor | Expression | Activation (Level of Phosphorylation) | Treatment with Fulvestrant |
|---|---|---|---|
| ER | High | | Low |
| ER (Ser 118) | | High | Weak |
| ER (Ser 167) | | High | Weak |
| ER: AIB1 Complex | | V. High | Weak |
| ER: N-CoR Complex | | Weak | Weak |
| Progesterone Receptor | High | | Low |
| IGF-1R | Low | Weak | Weak |
| ErbB1 | Low | Weak | Weak |
| ErbB2 | Low | Weak | Weak |
| ErbB3 | Low | Weak | Weak |
| ErbB4 | Low | Weak | Weak |
| Shc | | Weak | Weak |
| PI3K | | Weak | Weak |
| Erk | | Medium | Weak |
| Rsk | | Medium | Weak |
| Akt | | Medium | Weak |
| P70S6K | | Medium | Weak |
| Ki67 | High | | Weak |

Patient (pre- or postmenopausal woman) was biopsied or CTCs were isolated from blood. Analysis of the tumor cells revealed high expression and activation of ER/PR along with very high expression of the ER:AIB1 complex. The patient was treated with fulvestrant (Faslodex®) to degrade ER. The patient responded and on re-biopsy had the protein profile as shown above. Thus, a patient with the above protein profile responds to fulvestrant.

TABLE 12

Patient 4009: (ER+/PR−/ErbB2−)

| Receptor | Expression | Activation (Level of Phosphorylation) | Treatment with Aromatase Inhibitor + Chemotherapy |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | Low | Medium | Weak |
| ErbB2 | Low | Weak | Weak |
| ErbB3 | Low | Weak | Weak |
| ErbB4 | Low | Weak | Weak |
| Shc | | Weak | Weak |
| PI3K | | Weak | Weak |
| Erk | | Medium | Weak |
| Rsk | | Medium | Weak |
| Akt | | Medium | Weak |
| P70S6K | | Medium | Weak |
| Ki67 | High | | Weak |

Patient (pre- or postmenopausal woman) was biopsied or CTCs were isolated from blood. Analysis of her tumor cells revealed high expression and activation of ER. PR was expressed at very low levels. The patient was treated with an aromatase inhibitor+chemotherapy to shut down all ER-related activity. The patient responded and on re-biopsy had the protein profile as shown above. Thus, a patient with the above protein profile responds to aromatase inhibitor+chemotherapy.

TABLE 13

Patient 4010: (ER+/PR−/ErbB1+)

| Receptor | Expression | Activation (+/−GF) (Level of Phosphorylation) | Treatment with AI + Lapatinib or Erbitux ® |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | Medium | Medium | Weak |
| ErbB2 | Low | Weak | Weak |
| ErbB3 | Low | Weak | Weak |
| ErbB4 | Low | Weak | Weak |
| Shc | | Medium | Weak |
| PI3K | | Weak | Weak |
| Erk | | Medium | Weak |
| Rsk | | Medium | Weak |
| Akt | | Weak | Weak |
| P70S6K | | Weak | Weak |
| Ki67 | High | | Weak |

Patient (pre- or postmenopausal woman) was biopsied or CTCs were isolated from blood. Analysis of her tumor cells revealed high expression and activation of ER. PR was expressed at very low levels. ErbB1 was activated. The patient was treated with an aromatase inhibitor+lapatinib or Erbitux® to shut down all ER/ErbB1-related activity. The patient responded and on re-biopsy had the protein profile as shown above. Thus, a patient with the above protein profile responds to the combination of an aromatase inhibitor+lapatinib or Erbitux®.

TABLE 14

Patient 4011: (ER+/PR−/ErbB1+)

| Receptor | Expression | Activation (+/−GF) (Level of Phosphorylation) | Treatment with AI + Lapatinib or Erbitux ® |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | High | High | Weak |
| ErbB2 | Low | Weak | Weak |
| ErbB3 | Low | Weak | Weak |
| ErbB4 | Low | Weak | Weak |
| Shc | | High | Weak |
| PI3K | | Weak | Weak |
| Erk | | High | Weak |
| Rsk | | High | Weak |
| Akt | | Weak | Weak |
| P70S6K | | Weak | Weak |
| Ki67 | High | | Weak |

Patient (pre- or postmenopausal woman) was biopsied or CTCs were isolated from blood. Analysis of the tumor cells revealed high expression and activation of ER. PR was expressed at very low levels. ErbB1 was activated. The patient was treated with an aromatase inhibitor+lapatinib or Erbitux® to shut down all ER/ErbB1-related activity. The patient responded and on re-biopsy had the protein profile as shown above. Thus, a patient with the above protein profile responds to the combination of an aromatase inhibitor+lapatinib or Erbitux®.

TABLE 15

Patient 4012: (ER+/PR−/ErbB1+/ErbB2+)

| Receptor | Expression | Activation (+/−GF) (Level of Phosphorylation) | Treatment with AI + Lapatinib |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | Medium | Medium | Weak |
| ErbB2 | Medium | Medium | Weak |
| ErbB3 | Low | Weak | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |

Patient (pre- or postmenopausal woman) was biopsied or CTCs were isolated from blood. Analysis of her tumor cells revealed high expression and activation of ER. PR was expressed at very low levels. ErbB1 and ErbB2 were activated. The patient was treated with an aromatase inhibitor and lapatinib to shut down all ER/ErbB1/ErbB2-related activity. The patient responded and on re-biopsy had the protein profile as shown above. Thus, a patient with the above protein profile responds to aromatase inhibitor+lapatinib.

TABLE 16

Patient 4013: (ER+/PR−/ErbB1+/ErbB2+/ErbB3+)

| Receptor | Expression | Activation (+/−GF) (Level of Phosphorylation) | Treatment with AI + Lapatinib |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | Medium | Medium | Weak |
| ErbB2 | Medium | Medium | Weak |
| ErbB3 | Low | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |

Patient (pre- or postmenopausal woman) was biopsied or CTCs were isolated from blood. Analysis of the tumor cells revealed high expression and activation of ER. PR was expressed at very low levels. ErbB1, ErbB2, and ErbB3 were activated. The patient was treated with an aromatase inhibitor+lapatinib to shut down all ER/ErbB1/ErbB2/ErbB3-related activity. The patient responded and on re-biopsy had the protein profile as shown above. Thus, a patient with the above protein profile responds to therapy with an aromatase inhibitor+lapatinib.

Table 17 provides an example of a patient with locally recurrent or metastatic breast cancer who has relapsed on anti-angiogenic therapy. At least 3 weeks had elapsed since the patient received adjuvant chemotherapy and hormonal therapy for the locally recurrent or metastatic breast cancer.

TABLE 17

Patient 4014: (ER+/PR−/ErbB1+/ErbB2+/ErbB3+)

| Receptor | Expression | Activation (+/−GF) (Level of Phosphorylation) | Treatment with AI + Lapatinib + Avastin ® |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | Medium | Medium | Weak |
| ErbB2 | Medium | Medium | Weak |
| ErbB3 | Low | Medium | Weak |
| ErbB4 | Low | Weak | Weak |

TABLE 17-continued

| | | | |
|---|---|---|---|
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |

Endothelial cells:

| Receptor | Expression | Activation (Level of Phosphorylation) | Activation with Avastin® |
|---|---|---|---|
| VEGFR2 | Medium | Strong | Weak |
| VEGFR1 | Medium | Strong | Weak |
| Tie 2 | Low | Weak | Weak |
| V-Cadherin-R2 complex | Null | Medium | Weak |
| Shc | | Strong | Weak |
| PI3K | | Strong | Weak |
| Erk | | Strong | Weak |
| Rsk | | Strong | Weak |
| Akt | | Strong | Weak |
| P70S6K | | Strong | Weak |

Patient (pre- or postmenopausal woman) with locally recurrent or metastatic breast cancer was biopsied or CTCs were isolated from blood. Analysis of the tumor cells and endothelial cells revealed high expression and activation of ER along with VEGFR2 activation. PR was expressed at very low levels. ErbB1, ErbB2, and ErbB3 were activated. The patient was treated with an aromatase inhibitor+lapatinib+Avastin® to shut down all ER+ErbB1, ErbB2, ErbB3, and VEGFR2-related activity. The patient responded and on re-biopsy had the protein profile as shown above. Thus, a patient with the above protein profile responds to the combination of an aromatase inhibitor+lapatinib+Avastin®.

TABLE 18

Patient 4015: (ER+/PR−/ErbB2−/IGF-1R+)

| Receptor | Expression | Activation (+/−GF) (Level of Phosphorylation) | Treatment with AI + Anti-IGF-1R Ab |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | High/Medium | High | Weak |
| ErbB1 | Low | Low | Weak |
| ErbB2 | Low | Low | Weak |
| ErbB3 | Low | Weak | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |

Patient (pre- or postmenopausal woman) was biopsied or CTCs were isolated from blood. Analysis of the tumor cells revealed high expression and activation of ER. PR was expressed at very low levels. IGF-1R was activated. The patient was treated with an aromatase inhibitor+anti-IGF-1R antibodies to shut down all ER/IGF-1R-related activity. The patient responded and on re-biopsy had the protein profile as shown above. Thus, a patient with the above protein profile responds to aromatase inhibitor+anti-IGF-1R antibodies.

TABLE 19

Patient 4016: (ER+/PR+/ErbB2+)

| Receptor | Expression | Activation (+/−GF) (Level of Phosphorylation) | Treatment with AI + Herceptin® + Avastin® |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | High | | Low |
| IGF-1R | Low | Weak | Weak |
| ErbB1 | Medium | Weak | Weak |
| ErbB2 | High | High | Weak |
| P95 ErbB2 | Low | Low | Low |
| ErbB3 | Low | Weak | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |

Endothelial cells:

| Receptor | Expression | Activation (Level of Phosphorylation) | Activation with Avastin® |
|---|---|---|---|
| VEGFR2 | Medium | Strong | Weak |
| VEGFR1 | Medium | Strong | Weak |
| Tie 2 | Low | Weak | Weak |
| V-Cadherin-R2 complex | Null | Medium | Weak |
| Shc | | Strong | Weak |
| PI3K | | Strong | Weak |
| Erk | | Strong | Weak |
| Rsk | | Strong | Weak |
| Akt | | Strong | Weak |
| P70S6K | | Strong | Weak |

Patient (pre- or postmenopausal woman) with locally recurrent or metastatic breast cancer was biopsied or CTCs were isolated from blood. Analysis of the tumor cells and endothelial cells revealed high expression and activation of ER, PR, and ErbB2 along with VEGFR2 activation. The patient was treated with an aromatase inhibitor+Herceptin®+Avastin® to shut down all ER, ErbB2, and VEGFR2-related activity. The patient responded and on re-biopsy had the protein profile as shown above. Thus, a patient with the above protein profile responds to combination therapy with an aromatase inhibitor+Herceptin®+Avastin®.

TABLE 20

Patient 4017: (ER+/PR+/ErbB2+)

| Receptor | Expression | Activation (+/−GF) (Level of Phosphorylation) | Treatment with AI + Lapatinib + Avastin® |
|---|---|---|---|
| ER | High | | Medium |
| ER (Ser 118) | | High | Weak |
| ER (Ser 167) | | High | Weak |

TABLE 20-continued

| | | | |
|---|---|---|---|
| ER: AIB1 Complex | | Medium | Weak |
| ER: N-CoR Complex | | Weak | Medium |
| Progesterone Receptor | High | | Low |
| IGF-1R | Low | Weak | Weak |
| ErbB1 | Medium | Medium | Weak |
| ErbB2 | High | High | Weak |
| P95 ErbB2 | Medium | High | Weak |
| ErbB3 | Low | Medium | Weak |
| ErbB4 | Low | Weak | Weak |
| Shc | | Medium | Weak |
| PI3K | | High | Weak |
| Erk | | High | Weak |
| Rsk | | High | Weak |
| Akt | | High | Weak |
| P70S6K | | High | Weak |
| Ki67 | High | | Weak |

Endothelial cells:

| Receptor | Expression | Activation (Level of Phosphorylation) | Activation with Avastin ® |
|---|---|---|---|
| VEGFR2 | Medium | Strong | Weak |
| VEGFR1 | Medium | Strong | Weak |
| Tie 2 | Low | Weak | Weak |
| V-Cadherin--R2 complex | Null | Medium | Weak |
| Shc | | Strong | Weak |
| PI3K | | Strong | Weak |
| Erk | | Strong | Weak |
| Rsk | | Strong | Weak |
| Akt | | Strong | Weak |
| P70S6K | | Strong | Weak |

Patient (pre- or postmenopausal woman) with locally recurrent or metastatic breast cancer was biopsied or CTCs were isolated from blood. Analysis of the tumor cells and endothelial cells revealed high expression and activation of ER, ErbB2, and p95ErbB2, along with VEGFR2 activation. The patient was treated with an aromatase inhibitor+lapatinib+Avastin® to shut down all ER, ErbB1, ErbB2, ErbB3, p95ErbB2, and VEGFR2-related activity. The patient responded and on re-biopsy had the protein profile as shown above. Thus, a patient with the above protein profile responds to combination therapy with an aromatase inhibitor+lapatinib+Avastin®.

TABLE 21

Patient 4018: (ER+/PR−/ErbB2+)

| Receptor | Expression | Activation (+/−GF) (Level of Phosphorylation) | Treatment with AI + Herceptin ® + Taxanes + Avastin ® |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | Medium | Weak | Weak |
| ErbB2 | High | High | Weak |
| P95 ErbB2 | Low | Low | Low |
| ErbB3 | Low | Weak | Weak |
| ErbB4 | Low | Weak | Weak |
| Shc | | Medium | Weak |
| PI3K | | Medium | Weak |
| Erk | | Medium | Weak |

TABLE 21-continued

| | | | |
|---|---|---|---|
| Rsk | | Medium | Weak |
| Akt | | Medium | Weak |
| P70S6K | | Medium | Weak |
| Ki67 | High | | Weak |

Endothelial cells:

| Receptor | Expression | Activation (Level of Phosphorylation) | Activation with Avastin ® |
|---|---|---|---|
| VEGFR2 | Medium | Strong | Weak |
| VEGFR1 | Medium | Strong | Weak |
| Tie 2 | Low | Weak | Weak |
| V-Cadherin-R2 complex | Null | Medium | Weak |
| Shc | | Strong | Weak |
| PI3K | | Strong | Weak |
| Erk | | Strong | Weak |
| Rsk | | Strong | Weak |
| Akt | | Strong | Weak |
| P70S6K | | Strong | Weak |

Patient (pre- or postmenopausal woman) with locally recurrent or metastatic breast cancer was biopsied or CTCs were isolated from blood. Analysis of the tumor cells and endothelial cells revealed high expression and activation of ER and ErbB2, along with VEGFR2 activation. PR levels were low. The patient was treated with an aromatase inhibitor+Herceptin®+taxanes+Avastin® to shut down all ER, ErbB2, and VEGFR2-related activity. The patient responded and on re-biopsy had the protein profile as shown above. Thus, a patient with the above protein profile responds to the combination of an aromatase inhibitor+Herceptin®+Avastin®+chemotherapy.

TABLE 22

Patient 4019: (ER+/PR−/ErbB2+)

| Receptor | Expression | Activation (+/−GF) (Level of Phosphorylation) | Treatment with AI + Lapatinib + Avastin ® + Chemotherapy |
|---|---|---|---|
| ER | High | | Medium |
| ER (Ser 118) | | High | Weak |
| ER (Ser 167) | | High | Weak |
| ER: AIB1 Complex | | Medium | Weak |
| ER: N-CoR Complex | | Weak | Medium |
| Progesterone Receptor | Low | | Low |
| IGF-1R | Low | Weak | Weak |
| ErbB1 | Medium | Medium | Weak |
| ErbB2 | High | High | Weak |
| P95 ErbB2 | Medium | High | Weak |
| ErbB3 | Low | Medium | Weak |
| ErbB4 | Low | Weak | Weak |
| Shc | | Medium | Weak |
| PI3K | | High | Weak |
| Erk | | High | Weak |
| Rsk | | High | Weak |
| Akt | | High | Weak |
| P70S6K | | High | Weak |
| Ki67 | High | | Weak |

Endothelial cells:

| Receptor | Expression | Activation (Level of Phosphorylation) | Activation with Avastin ® |
|---|---|---|---|
| VEGFR2 | Medium | Strong | Weak |
| VEGFR1 | Medium | Strong | Weak |
| Tie 2 | Low | Weak | Weak |

TABLE 22-continued

| | | |
|---|---|---|
| V-Cadherin--R2 complex | Null | Medium | Weak |
| Shc | | Strong | Weak |
| PI3K | | Strong | Weak |
| Erk | | Strong | Weak |
| Rsk | | Strong | Weak |
| Akt | | Strong | Weak |
| P70S6K | | Strong | Weak |

Patient (pre- or postmenopausal woman) with locally recurrent or metastatic breast cancer was biopsied or CTCs were isolated from blood. Analysis of the tumor cells and endothelial cells revealed high expression and activation of ER, ErbB2, and p95ErbB2, along with VEGFR2 activation. PR level was low. The patient was treated with an aromatase inhibitor+lapatinib+Avastin®+chemotherapy to shut down all ER, ErbB1, ErbB2, ErbB3, p95ErbB2, and VEGFR2-related activity. The patient responded and on re-biopsy had the protein profile as shown above. Thus, a patient with the above protein profile responds to combination therapy with an aromatase inhibitor+lapatinib+Avastin®+chemotherapy.

Accordingly, in certain aspects, the present invention allows the intelligent selection of activation markers that will best predict survival. The most appropriate activation markers may vary between different drugs, and can be used as a guide to select between anticancer drug monotherapy versus combination therapy with a cocktail of anticancer drugs to provide personalized, targeted therapies.

Example 9

Selection of Patients for Treatment of Her2-Positive Breast Cancer

In the United States, there are approximately 200,000 cases of breast cancer each year. HER-2/ErbB2, a 185 kDa membrane receptor tyrosine kinase, is found in 18% to 20% of breast cancers and has been associated with an increased rate of relapse and death. ErbB2 is now an established predictive marker of benefit from therapies such as trastuzumab (Herceptin®).

During the last decade, major progress in the treatment of ErbB2+ breast cancer was achieved. Herceptin® has changed the natural history of the disease in the metastatic and adjuvant settings. Lapatinib, now commercially available as Tykerb® (GlaxoSmithKline), is an important addition and the first of what will likely be many agents that will be available in the post-Herceptin® setting.

Unfortunately, resistance to Herceptin® develops in many cases, and in almost all cases in the metastatic setting. Both de novo and acquired resistance to Herceptin® have also been observed.

Possible modes of resistance to Herceptin® are:
Altered target expression (change in ErbB2 status)
Signaling by alternate pathways (IGF-1R)
Preferential dimerization with other receptors (ErbB1 or ErbB3)
Sub-optimal drug delivery (CNS metastatic disease among women with ErbB2 breast cancer appears to be particularly common. The incidence of CNS metastatic disease in patients with ErbB2+ metastatic breast cancer can be as high as one-third of patients with ErbB2+ metastatic disease).
PTEN alteration
PI3K mutations
P95ErbB2 expression or ErbB2 truncation
Overexpression or amplification of cMET
Markers for selection/efficacy of therapy:
5-FU/capcitibine: Thymidylate synthetase (TS) expression
Dihydropyrimidine dehydrogenase (DPD) expression
HDACs decrease in TS expression
Taxanes: ErbB2
Anthracyclines: TOPO2 overexpression
ErbB2 Positive: (5-FU or taxanes or anthracyclines)
Multiple chemotherapy regimens have been tested in combination with Herceptin®. The preferred combination is treatment with paclitaxel, docetaxel, a taxane plus a platinum salt, in the metastatic setting. All targeted therapies can also be used in combination.

The exemplary patient profiles shown below in Tables 23-25 illustrate how an analysis of the pathways active in circulating tumor cells (CTCs) from blood or cancer cells obtained from a biopsy can be used to help physicians select patients who may be responsive to trastuzumab (Herceptin®) and therefore benefit from such therapy for the treatment of a breast tumor. The exemplary patient profiles shown below in Tables 26-31 illustrate how an analysis of the pathways active in CTCs from blood or cancer cells obtained from a biopsy can be used to help physicians select a suitable therapy for patients after Herceptin® relapse resulting from either de novo or acquired resistance. In brief, the activation levels of different components of signal transduction pathways such as the ErbB receptor pathways in CTCs or biopsy-derived cancer cells can be determined in the presence or absence of different combinations of test therapeutic agents.

TABLE 23

Patient 5001: (ErbB2+)

| Receptor | Expression | Activation (+/−GF) (Level of Phosphorylation) | Treatment with Herceptin ® + Avastin ® + Taxanes (Optional) |
|---|---|---|---|
| IGF-1R | Low | Weak | Weak |
| ErbB1 | Medium | Weak | Weak |
| ErbB2 | High | High | Weak |
| P95 ErbB2 | Low | Weak | Weak |
| ErbB3 | Low | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

Endothelial Cells:

| Receptor | Expression | Activation (+/−GF) (Level of Phosphorylation) | Activation with Avastin ® |
|---|---|---|---|
| VEGFR2 | Medium | Strong | Weak |
| VEGFR1 | Medium | Medium | Weak |
| Tie 2 | Low | Weak | Weak |
| V-Cadherin-R2 complex | Null | Medium | Weak |
| Shc | | Strong | Weak |
| PI3K | | Strong | Weak |
| Erk | | Strong | Weak |
| Rsk | | Strong | Weak |
| Akt | | Strong | Weak |
| P70S6K | | Strong | Weak |

Patient (pre- or postmenopausal woman) with locally recurrent or metastatic breast cancer was biopsied or CTCs were isolated from blood. Analysis of her tumor cells and endothelial cells revealed high expression and activation of ErbB2, along with VEGFR2 activation. The patient was treated with Herceptin®+taxane+Avastin® to shut down all ErbB2 and VEGFR2-related activity. The patient responded and on re-biopsy had the protein profile as shown above. Thus, a patient with the above protein profile responds to Herceptin®+Avastin®+chemotherapy.

TABLE 24

| | | | Treatment with Herceptin ® + Avastin ® + FEC: [fluorouracil, epirubicin (anthracyclin), and cyclophosphamide] |
|---|---|---|---|
| Receptor | Expression | Activation (+/−GF) (Level of Phosphorylation) | |

Patient 5002: (ErbB2+)

| Receptor | Expression | Activation (+/−GF) (Level of Phosphorylation) | Treatment with Herceptin ® + Avastin ® + FEC |
|---|---|---|---|
| IGF-1R | Low | Weak | Weak |
| ErbB1 | Medium | Weak | Weak |
| ErbB2 | High | High | Weak |
| P95 ErbB2 | Low | Weak | Weak |
| ErbB3 | Low | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | High | | High |

Endothelial Cells:

| Receptor | Expression | Activation (Level of Phosphorylation) | Activation with Avastin ® |
|---|---|---|---|
| VEGFR2 | Medium | Strong | Weak |
| VEGFR1 | Medium | Strong | Weak |
| Tie 2 | Low | Weak | Weak |
| V-Cadherin-R2 complex | Null | Medium | Weak |
| Shc | | Strong | Weak |
| PI3K | | Strong | Weak |
| Erk | | Strong | Weak |
| Rsk | | Strong | Weak |
| Akt | | Strong | Weak |
| P70S6K | | Strong | Weak |

Patient (pre- or postmenopausal woman) with locally recurrent or metastatic breast cancer was biopsied or CTCs were isolated from blood. Analysis of her tumor cells and endothelial cells revealed high expression and activation of ErbB2 and TOPO2, along with VEGFR2 activation. The patient was treated with Herceptin®+anthracyclin+chemotherapy+Avastin® to shut down all ErbB2, VEGFR2, and TOPO2-related activity. The patient responded and on re-biopsy had the protein profile as shown above. Thus, a patient with the above protein profile responds to combination therapy with Herceptin®+anthracyclin+chemotherapy+Avastin®.

TABLE 25

Patient 5003: (ErbB2+)

| Receptor | Expression | Activation (+/−GF) (Level of Phosphorylation) | Treatment with Herceptin ® + Sorafinib or Sunitinib or AZD2171 + Taxanes (Optional) |
|---|---|---|---|
| IGF-1R | Low | Weak | Weak |
| ErbB1 | Medium | Weak | Weak |
| ErbB2 | High | High | Weak |
| P95 ErbB2 | Low | Weak | Weak |
| ErbB3 | Low | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

TABLE 25-continued

| Endothelial Cells and Pericytes: | | | | |
|---|---|---|---|---|
| Receptor | Expression | Activation (Level of Phosphorylation) | Activation with AZD2171 or Sorafinib or Sunitinib | Activation with Avastin ® |
| VEGFR2 | Medium | Strong | Weak | Weak |
| VEGFR1 | Medium | Strong | Weak | Medium |
| Tie 2 | Low | Weak | Weak | Weak |
| V-Cadherin-R2 complex | Null | Medium | Weak | Weak |
| PDGFRa | Medium | High | Weak | High |
| PDGFRb | Medium | High | Weak | High |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs were isolated from blood. Analysis of her tumor cells and endothelial cells revealed high expression and activation of ErbB2 and PDGFR, along with VEGFR2 activation. The patient was treated with Herceptin®+sorafinib+Avastin® to shut down all ErbB2, PDGFR, and VEGFR2-related activity. Because PDGFR is overexpressed and activated in Avastin®-resistant patients, information such as that presented above indicates that AZD2171 or sorafinib, which inhibits PDGFR as well as VEGFR, may be agents of choice to treat such tumors. The patient responded and on re-biopsy had the protein profile as shown above. Thus, a patient with the above protein profile responds to Herceptin®+sorafinib+chemotherapy.

TABLE 26

| Patient 5004: (ErbB2+) | | | |
|---|---|---|---|
| Receptor | Expression | Activation (+/−GF) (Level of Phosphorylation) | Treatment with Lapatinib + Taxanes + Sorafinib or Sunitinib or AZD2171 |
| IGF-1R | Low | Weak | Weak |
| ErbB1 | High | High | Weak |
| ErbB2 | High | High | Weak |
| P95 ErbB2 | Low | Weak | Weak |
| ErbB3 | Medium | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

| Endothelial Cells and Pericytes: | | | | |
|---|---|---|---|---|
| Receptor | Expression | Activation (Level of Phosphorylation) | Activation with AZD2171 or Sorafinib or Sunitinib | Activation with Avastin ® |
| VEGFR2 | Medium | Strong | Weak | Weak |
| VEGFR1 | Medium | Strong | Weak | Medium |
| Tie 2 | Low | Weak | Weak | Weak |
| V-Cadherin-R2 complex | Null | Medium | Weak | Weak |
| PDGFRa | Medium | High | Weak | High |
| PDGFRb | Medium | High | Weak | High |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs were isolated from blood. Analysis of her tumor cells and endothelial cells revealed high expression and activation of ErbB1, ErbB2, and PDGFR, along with VEGFR2 activation. The patient was treated with lapatinib+sorafinib to shut down all ErbB1, ErbB2, PDGFR, and VEGFR2-related activity. Because ErbB1 and PDGFR is overexpressed and activated in Herceptin®- and Avastin®-resistant patients, information such as that presented above indicates that AZD2171 or sorafinib, which inhibits PDGFR as well as VEGFR, might be agents of choice to treat such tumors. Lapatinib was used instead of Herceptin® since lapatinib inhibits both ErbB1 and ErbB2. The patient responded and on re-biopsy had the protein profile as shown above. Thus, a patient with the above protein profile responds to lapatinib+sorafinib+chemotherapy.

Patient (pre- or postmenopausal woman) with locally recurrent or metastatic breast cancer was biopsied or CTCs were isolated from blood. Analysis of her tumor cells and endothelial cells revealed high expression and activation of IGF-1R, ErbB2, and PDGFR, along with VEGFR2 activation. The patient was treated with Herceptin®+sorafinib+Avastin®+IGF-1R antibody (Ab) to shut down all IGF-1R, ErbB2, PDGFR, and VEGFR2-related activity. Because IGF-1R and PDGFR is overexpressed and activated in Herceptin®- and Avastin®-resistant patients, information such as that presented above indicates that AZD2171 or sorafinib, which inhibits PDGFR as well as VEGFR, may be agents of choice to treat such tumors. IGF-1R Ab along with Herceptin® was used instead of Herceptin® alone to inhibit both IGF-1R and ErbB2. The patient responded and on re-biopsy had the protein profile as shown above. Thus, a patient with the above protein profile responds to Herceptin®+IGF-1R Ab+sorafinib+chemotherapy.

TABLE 27

Patient 5005: (ErbB2+)

| Receptor | Expression | Activation (+/−GF) (Level of Phosphorylation) | Treatment with Herceptin ® + Taxanes + Sorafinib or Sunitinib or AZD2171 + Anti-IGF-1R Ab |
|---|---|---|---|
| IGF-1R | High | High | Weak |
| ErbB1 | Medium | Medium | Weak |
| ErbB2 | High | High | Weak |
| P95 ErbB2 | Low | Weak | Weak |
| ErbB3 | Low | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

Endothelial Cells and Pericytes:

| Receptor | Expression | Activation (Level of Phosphorylation) | Activation with AZD2171 Sorafinib or Sunitinib | Activation with Avastin ® |
|---|---|---|---|---|
| VEGFR2 | Medium | Strong | Weak | Weak |
| VEGFR1 | Medium | Strong | Weak | Medium |
| Tie 2 | Low | Weak | Weak | Weak |
| V-Cadherin-R2 complex | Null | Medium | Weak | Weak |
| PDGFRa | Medium | High | Weak | High |
| PDGFRb | Medium | High | Weak | High |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs

TABLE 28

Patient 5006: (ErbB2+/PTEN deletion)

| Receptor | Expression | Activation (+/−GF) (Level of Phosphorylation) | Treatment with Lapatinib + Taxanes + Sorafinib or Sunitinib or AZD2171 + Rapamycin |
|---|---|---|---|
| IGF-1R | Low | Low | Weak |
| ErbB1 | Medium | Medium | Medium |
| ErbB2 | High | High | Weak |

TABLE 28-continued

| | | | |
|---|---|---|---|
| P95 ErbB2 | Medium | High | Weak |
| ErbB3 | Low | Medium | Medium |
| ErbB4 | Low | Weak | Weak |
| PTEN | Low | Low | Low |
| Shc | | Medium | Weak |
| PI3K | | Medium | Medium |
| Erk | | Medium | Weak |
| Rsk | | Medium | Weak |
| Akt | | Medium | High |
| P70S6K | | Medium | Weak |
| Ki67 | High | | Weak |
| TOPO2 | Low | | Weak |

Endothelial Cells and Pericytes:

| Receptor | Expression | Activation (Level of Phosphorylation) | Activation with AZD2171 or Sorafinib or Sunitinib | Activation with Avastin ® |
|---|---|---|---|---|
| VEGFR2 | Medium | Strong | Weak | Weak |
| VEGFR1 | Medium | Strong | Weak | Medium |
| Tie 2 | Low | Weak | Weak | Weak |
| V-Cadherin-R2 complex | Null | Medium | Weak | Weak |
| PDGFRa | Medium | High | Weak | High |
| PDGFRb | Medium | High | Weak | High |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs were isolated from blood. Analysis of her tumor cells and endothelial cells revealed high expression and activation of p95 ErbB2, ErbB2, and PDGFR, along with VEGFR2 activation. The patient also has a PTEN deletion. The patient was treated with lapatinib+sorafinib to shut down all ErbB2, PDGFR, and VEGFR2-related activity. Because p95 ErbB2 and PDGFR is overexpressed and activated in Herceptin®- and Avastin®-resistant patients, information such as that presented above indicates that AZD2171 or sorafinib, which inhibits PDGFR as well as VEGFR, may be agents of choice to treat such tumors. Lapatinib was used instead of Herceptin® to inhibit both p95 ErbB2 and ErbB2 and mTor inhibitor was used to shut down downstream signaling activity. The patient responded and on re-biopsy had the protein profile as shown above. Thus, a patient with the above protein profile responds to lapatinib+sorafinib+rapamycin+chemotherapy.

TABLE 29

Patient 5007: (ErbB2+/p95 ErbB2+)

| Receptor | Expression | Activation (+/−GF) (Level of Phosphorylation) | Treatment with Lapatinib + Taxanes + Sorafinib or Sunitinib or AZD2171 |
|---|---|---|---|
| IGF-1R | Low | Low | Weak |
| ErbB1 | Medium | Medium | Weak |
| ErbB2 | High | High | Weak |
| P95 ErbB2 | High | High | Weak |
| ErbB3 | Low | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | High | Weak |
| P70S6K | | Medium | Weak |
| Ki67 | High | | Weak |
| TOPO2 | Low | | Weak |

TABLE 29-continued

| | | | Endothelial Cells and Pericytes: | |
|---|---|---|---|---|
| Receptor | Expression | Activation (Level of Phosphorylation) | Activation with AZD2171 or Sorafinib or Sunitinib | Activation with Avastin ® |
| VEGFR2 | Medium | Strong | Weak | Weak |
| VEGFR1 | Medium | Strong | Weak | Medium |
| Tie 2 | Low | Weak | Weak | Weak |
| V-Cadherin-R2 complex | Null | Medium | Weak | Weak |
| PDGFRa | Medium | High | Weak | High |
| PDGFRb | Medium | High | Weak | High |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs were isolated from blood. Analysis of her tumor cells and endothelial cells revealed high expression and activation of p95 ErbB2, ErbB2, and PDGFR, along with VEGFR2 activation. The patient was treated with lapatinib+sorafinib to shut down all ErbB2, PDGFR, and VEGFR2-related activity. Because p95 ErbB2 and PDGFR is overexpressed and activated in Herceptin®- and Avastin®-resistant patients, information such as that presented above indicates that AZD2171 or sorafinib, which inhibits PDGFR as well as VEGFR, may be agents of choice to treat such tumors. Lapatinib was used instead of Herceptin® to inhibit both p95 ErbB2 and ErbB2. The patient responded and on re-biopsy had the protein profile as shown above. Thus, a patient with the above protein profile responds to the combination of lapatinib+sorafinib+chemotherapy.

TABLE 30

| | | Patient 5008: (ErbB2+) | |
|---|---|---|---|
| Receptor | Expression | Activation (+/−GF) (Level of Phosphorylation) | Treatment with Lapatinib + Taxanes + Sorafinib or Sunitinib or AZD2171 |
| IGF-1R | Low | Low | Weak |
| ErbB1 | Medium | Medium | Weak |
| ErbB2 | High | High | Weak |
| P95 ErbB2 | Low | Weak | Weak |
| ErbB3 | Low | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |
| | | Endothelial Cells and Pericytes: | |
| Receptor | Expression | Activation (Level of Phosphorylation) | Activation with AZD2171 or Sorafinib or Sunitinib | Activation with Avastin ® |
| VEGFR2 | Medium | Strong | Weak | Weak |
| VEGFR1 | Medium | Strong | Weak | Medium |
| Tie 2 | Low | Weak | Weak | Weak |
| V-Cadherin-R2 complex | Null | Medium | Weak | Weak |
| PDGFRa | Medium | High | Weak | High |
| PDGFRb | Medium | High | Weak | High |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with metastatic breast cancer was biopsied or CTCs were isolated from blood. Analysis of her tumor cells and endothelial cells revealed high expression and activation of ErbB2 and PDGFR, along with VEGFR2 activation. The patient had brain metastases. The patient was treated with lapatinib+sorafinib to shut down all ErbB2, PDGFR, and VEGFR2-related activity. Because PDGFR is overexpressed and activated in Avastin®-resistant patients, information such as that presented above indicates that AZD2171 or sorafinib, which inhibits PDGFR as well as VEGFR, may be agents of choice to treat such tumors. Lapatinib was used instead of Herceptin® as the patient had brain metastases. The patient responded and on re-biopsy had the protein profile as shown above. Thus, a patient with the above protein profile responds to lapatinib+sorafinib+chemotherapy.

TABLE 31

Patient 5009: (ErbB2+)

| Receptor | Expression | Activation (+/−GF) (Level of Phosphorylation) | Treatment with Herceptin ® + Taxanes + Avastin ® + Lapatinib |
|---|---|---|---|
| IGF-1R | Low | Weak | Weak |
| ErbB1 | Medium | Medium | Weak |
| ErbB2 | High | High | Weak |
| P95 ErbB2 | Medium | Medium | Weak |
| ErbB3 | Low | Medium | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

Endothelial Cells and Pericytes:

| Receptor | Expression | Activation (Level of Phosphorylation) | Activation with AZD2171 or Sorafinib or Sunitinib | Activation with Avastin ® |
|---|---|---|---|---|
| VEGFR2 | Medium | Strong | Weak | Weak |
| VEGFR1 | Medium | Strong | Weak | Weak |
| Tie 2 | Low | Weak | Weak | Weak |
| V-Cadherin-R2 complex | Null | Medium | Weak | Weak |
| PDGFRa | Medium | Low | Weak | Weak |
| PDGFRb | Medium | Low | Weak | Weak |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs were isolated from blood. Analysis of her tumor cells and endothelial cells revealed high expression and activation of ErbB1, ErbB2, ErbB3, and PDGFR, along with VEGFR2 activation. The patient was treated with Herceptin®+lapatinib+sorafinib to shut down all ErbB1, ErbB2, ErbB3, PDGFR, and VEGFR2-related activity. Because ErbB1 and PDGFR is overexpressed and activated in Herceptin®- and Avastin®-resistant patients, information such as that presented above indicates that AZD2171 or sorafinib, which inhibits PDGFR as well as VEGFR, may be agents of choice to treat such tumors. Lapatinib was used with Herceptin® to inhibit both ErbB1, ErbB2, and ErbB3. The patient responded and on re-biopsy had the protein profile as shown above. Thus, a patient with the above protein profile responds to the combination of lapatinib+Herceptin®+sorafinib+chemotherapy.

Example 10

Selection of Patients for Treatment of ER-, PR-, and ErbB2-Negative Breast Cancer Approximately 15-20% of women with breast cancer have the triple negative type of cancer. Patients with "triple receptor negative breast cancer" have a complete absence of hormone receptors ER, PR, and HER-2/ErbB2, with an aggressive clinical course and a paucity of treatment options. The only therapeutic option is chemotherapy and in this respect the choice of cytostatic agents is limited. The standard treatment for triple negative breast cancer is typically a combination of chemotherapy, surgery, and/or radiation therapy. When treated with standard therapy, women with triple negative breast cancer have a worse long-term outcome compared to women with non-triple negative breast cancer. Triple negative breast cancers cells usually have ErbB1 expressed on their cell surface. Women with ErbB1-positive breast cancer have worse long-term outcome compared to women whose tumors do not express ErbB1. As such, there is a need in the art for methods of profiling, selecting, and predicting treatment options for triple negative breast cancer patients.

TABLE 32

Patient 6001: (Triple negative with low ErbB1)

| Receptor | Expression | Activation (+/−GF) (Level of Phosphorylation) | Treatment with Taxanes + Avastin ® |
|---|---|---|---|
| ER | Low | | |
| PR | Low | | |
| IGF-1R | Low | Weak | Weak |
| ErbB1 | Low | Weak | Weak |
| ErbB2 | Low | Weak | Weak |
| P95 ErbB2 | Low | Weak | Weak |
| ErbB3 | Low | Weak | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

Endothelial Cells and Pericytes:

| Receptor | Expression | Activation (Level of Phosphorylation) | Activation with AZD2171 or Sorafinib or Sunitinib | Activation with Avastin ® |
|---|---|---|---|---|
| VEGFR2 | Medium | Strong | Weak | Weak |
| VEGFR1 | Medium | Strong | Weak | Weak |
| Tie 2 | Low | Weak | Weak | Weak |
| V-Cadherin-R2 complex | Null | Medium | Weak | Weak |
| PDGFRa | Medium | Low | Weak | Weak |
| PDGFRb | Medium | Low | Weak | Weak |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal women) with locally recurrent or metastatic breast cancer was biopsied or CTCs were isolated from blood. Analysis of her tumor cells and endothelial cells revealed low expression and no activation of ER, ErbB2, and p95 ErbB2, with only VEGFR2 activation. The patient was treated with Taxanes+Avastin® to shut down VEGFR2-related activity. The patient responded and on re-biopsy had the protein profile as shown above. Thus, a patient with the above protein profile responds to Avastin®+chemotherapy.

TABLE 33

Patient 6002: (Triple negative)

| Receptor | Expression | Activation (+/−GF) (Level of Phosphorylation) | Treatment with Tarceva ® + Taxanes + Avastin ® |
|---|---|---|---|
| ER | Low | | |
| PR | Low | | |
| IGF-1R | Low | Weak | Weak |
| ErbB1 | Medium | Medium | Weak |
| ErbB2 | Low | Weak | Weak |
| P95 ErbB2 | Low | Weak | Weak |
| ErbB3 | Low | Weak | Weak |
| ErbB4 | Low | Weak | Weak |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

TABLE 33-continued

| | | | Endothelial Cells and Pericytes: | |
|---|---|---|---|---|
| Receptor | Expression | Activation (Level of Phosphorylation) | Activation with AZD2171 or Sorafinib or Sunitinib | Activation with Avastin ® |
| VEGFR2 | Medium | Strong | Weak | Weak |
| VEGFR1 | Medium | Strong | Weak | Weak |
| Tie 2 | Low | Weak | Weak | Weak |
| V-Cadherin-R2 complex | Null | Medium | Weak | Weak |
| PDGFRa | Medium | Low | Weak | Weak |
| PDGFRb | Medium | Low | Weak | Weak |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs were isolated from blood. Analysis of her tumor cells and endothelial cells revealed medium expression and activation of ErbB1 and VEGFR2 activation. The patient was treated with Tarceva®+Avastin® to shut down all ErbB1 and VEGFR2-related activity. The patient responded and on re-biopsy had the protein profile as shown above. Thus, a patient with the above protein profile responds to Tarceva®+Avastin®+chemotherapy.

TABLE 34

| | | Patient 6003: (Triple negative) | |
|---|---|---|---|
| Receptor | Expression | Activation (+/−GF) (Level of Phosphorylation) | Treatment with Pan Her Inhibitor + Taxanes + Avastin ® |
| ER | Low | | |
| PR | Low | | |
| IGF-1R | Low | Weak | Weak |
| ErbB1 | Medium | Medium | Weak |
| ErbB2 | Low | Medium | Weak |
| P95 ErbB2 | Nil | Weak | Weak |
| ErbB3 | Low | Medium | Weak |
| ErbB4 | Low | Weak | Weak |
| PTEN | Medium | | |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

| | | Endothelial Cells and Pericytes: | |
|---|---|---|---|
| Receptor | Expression | Activation (Level of Phosphorylation) | Activation with AZD2171 or Sorafinib or Sunitinib | Activation with Avastin ® |
| VEGFR2 | Medium | Strong | Weak | Weak |
| VEGFR1 | Medium | Strong | Weak | Weak |
| Tie 2 | Low | Weak | Weak | Weak |
| V-Cadherin-R2 complex | Null | Medium | Weak | Weak |
| PDGFRa | Medium | Low | Weak | Weak |
| PDGFRb | Medium | Low | Weak | Weak |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs were isolated from blood. Analysis of her tumor cells and endothelial cells revealed medium expression and activation of ErbB1, ErbB2, and ErbB3, along with VEGFR2 activation. The patient was treated with a Pan Her inhibitor+Avastin® to shut down all ErbB1, ErbB2, ErbB3, and VEGFR2-related activity. The patient responded and on re-biopsy had the protein profile as shown above. Thus, a patient with the above protein profile responds to the combination of a Pan Her inhibitor+Avastin®+chemotherapy. Examples of Pan Her inhibitors include, but are not limited to, BMS-599626 and CI-1033.

TABLE 35

Patient 6004: (Triple negative)

| Receptor | Expression | Activation (+/−GF) (Level of Phosphorylation) | Treatment with Pan Her inhibitor + Taxanes + Avastin ® + Rapamycin |
|---|---|---|---|
| ER | Low | | |
| PR | Low | | |
| IGF-1R | Low | Weak | Weak |
| ErbB1 | Medium | Medium | Weak |
| ErbB2 | Low | Medium | Weak |
| P95 ErbB2 | Nil | Nil | Nil |
| ErbB3 | Low | Medium | Weak |
| ErbB4 | Low | Weak | Weak |
| PTEN | Nil | | |
| Shc | | Medium | Weak |
| PI3K | | Medium | Weak |
| Erk | | Medium | Weak |
| Rsk | | Medium | Weak |
| Akt | | Medium | Weak |
| P70S6K | | Medium | Weak |
| Ki67 | High | | Weak |
| TOPO2 | Low | | Weak |

Endothelial Cells and Pericytes:

| Receptor | Expression | Activation (Level of Phosphorylation) | Activation with AZD2171 or Sorafinib or Sunitinib | Activation with Avastin ® |
|---|---|---|---|---|
| VEGFR2 | Medium | Strong | Weak | Weak |
| VEGFR1 | Medium | Strong | Weak | Weak |
| Tie 2 | Low | Weak | Weak | Weak |
| V-Cadherin-R2 complex | Null | Medium | Weak | Weak |
| PDGFRa | Medium | Low | Weak | Weak |
| PDGFRb | Medium | Low | Weak | Weak |
| Shc | | Strong | Weak | Weak |
| PI3K | | Strong | Weak | Weak |
| Erk | | Strong | Weak | Weak |
| Rsk | | Strong | Weak | Weak |
| Akt | | Strong | Weak | Weak |
| P70S6K | | Strong | Weak | Weak |

Patient (pre- or postmenopausal woman) with locally recurrent or metastatic breast cancer was biopsied or CTCs were isolated from blood. Analysis of her tumor cells and endothelial cells revealed medium expression and activation of ErbB1, ErbB2, and ErbB3, along with VEGFR2 activation. PTEN was deleted. The patient was treated with a Pan Her inhibitor+Avastin®+mTOR inhibitor to shut down all ErbB1, ErbB2, ErbB3, and VEGFR2-related activity. The patient responded and on re-biopsy had the protein profile as shown above. Thus, a patient with the above protein profile responds to a Pan Her inhibitor+Avastin®+rapamycin+chemotherapy.

Example 11

Monitoring Breast Cancer Patients for EGFR and/or HER-2 Activation to Guide Treatment Selection Five breast cancer patients on therapy were examined for circulating tumor cell (CTC) number, EGFR expression on CTCs by staining, and EGFR and HER-2 (ErbB2) phosphorylation using the proximity assays described herein. Patient demographics, cancer history, and current medications are shown in Tables 36, 37, and 38, respectively. The results of tests on the primary tumor for estrogen receptor (ER), progesterone receptor (PR), and HER-2 are provided in Table 39.

Figure 10:
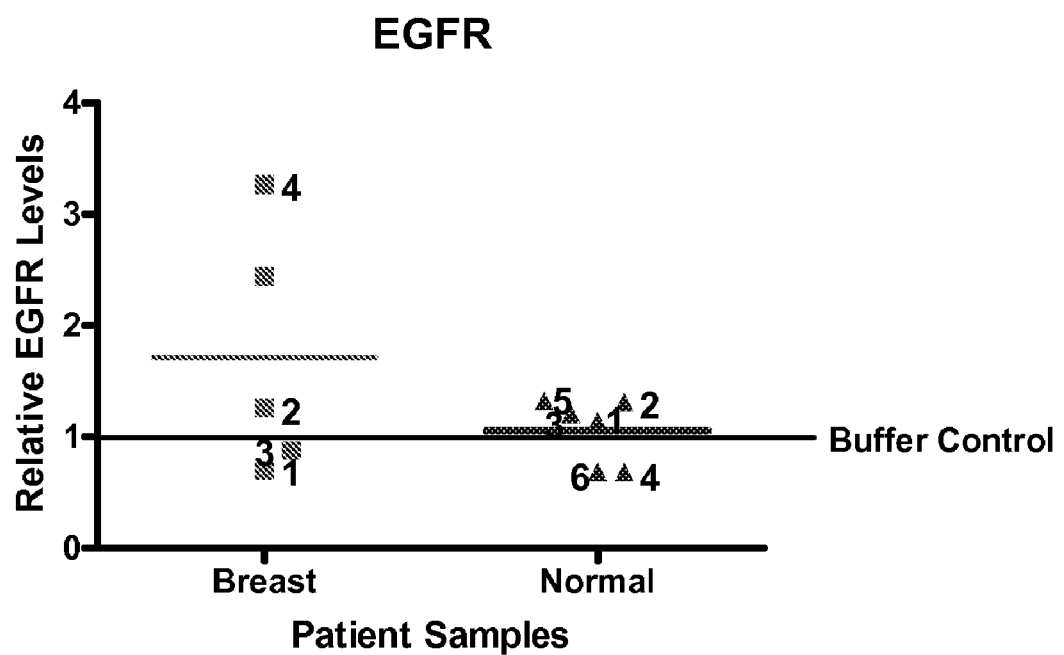
FIG. 10 shows the relative phosphorylation levels of EGFR for 5 breast cancer and 6 normal samples. Data is also shown in Table 40.
Figure 11:
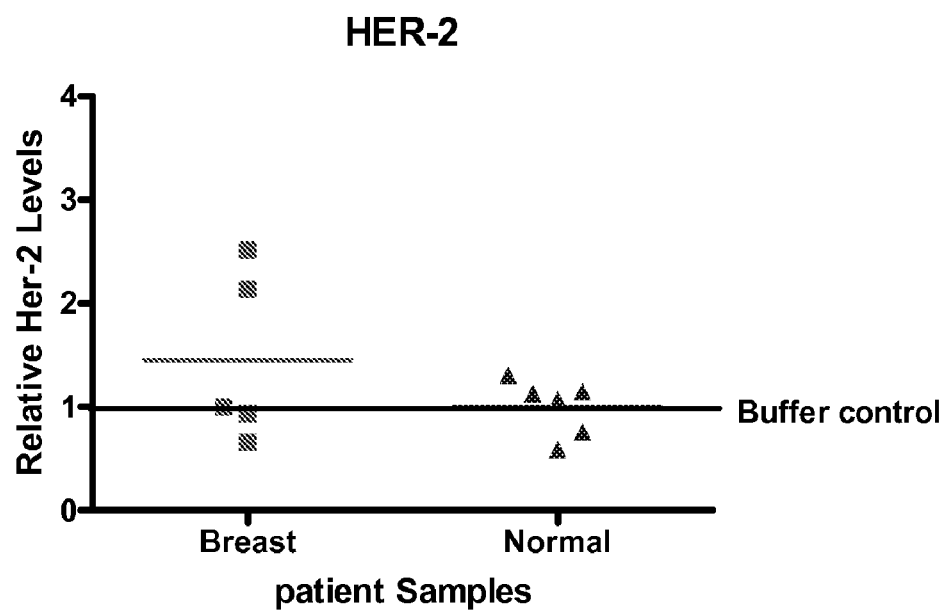
FIG. 11 shows the relative phosphorylation levels of HER-2 for 5 breast cancer and 6 normal samples. Data is also shown in Table 41.
Figure 12:
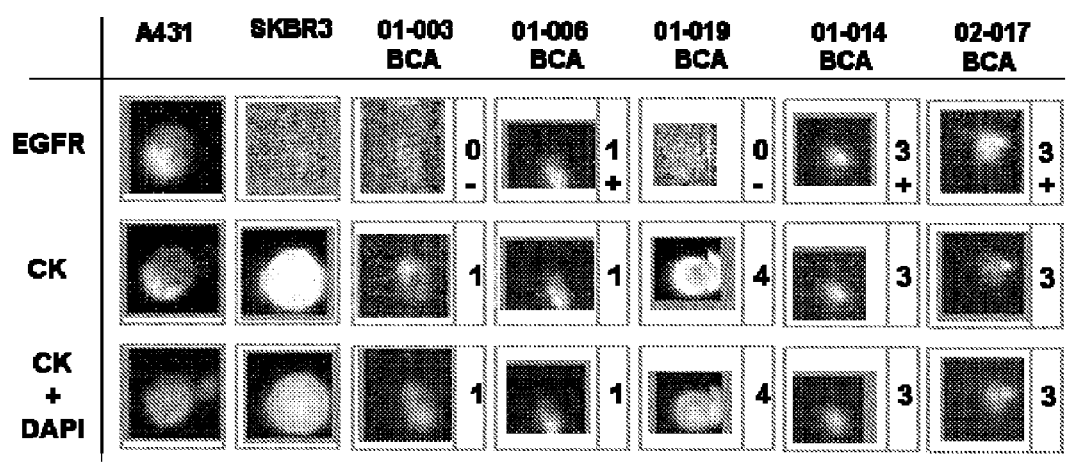
FIG. 12 shows images of CTC staining on the Veridex CellSearch™ System for 5 breast cancer patients. Cell lines controls are A431 (positive for EGFR) and SKBr3 (positive for HER-2).

Tables 40 and 41 show the numbers of CTCs detected in each sample and the relative phosphorylation levels for EGFR and HER-2. Relative phosphorylation levels were calculated using the mean of 4 buffer controls. The phosphorylation information is also plotted in FIGS. 10 and 11. FIG. 12 shows images of CTC staining for EGFR, cytokeratin (CK), and cytokeratin with DAPI. Cell line controls were SKBr3 and A431, which are positive for HER-2 and EGFR expression, respectively. Whole blood from 6 normal individuals was processed using the same protocol as controls. None of the normal samples showed EGFR or HER-2 phosphorylation above background.

TABLE 36

Demographics of the 5 breast cancer patients in the study.

| Patient Number | Date of Birth | Gender | Race/Ethnicity |
|---|---|---|---|
| 01-003 | 01/APR./1951 | Female | Hispanic/Latino |
| 01-006 | 15/OCT./1929 | Female | Asian |
| 01-014 | 29/SEP./1966 | Female | Hispanic/Latino |
| 01-019 | 08/JUN./1954 | Female | Asian |
| 02-017 | 03/OCT./1954 | Female | Caucasian |

TABLE 39

Diagnostic test results on ER, PR, and HER-2 for the 5 breast cancer patients in the study.

| Patient Number | Is the subject ER positive? | Is the subject PR positive? | Is the subject HER2 positive? |
|---|---|---|---|
| 01-003 | No | No | Yes |
| 01-006 | No | No | Unknown |
| 01-014 | No | No | Yes |
| 01-019 | Yes | No | No |
| 02-017 | No | No | No |

TABLE 37

Cancer history of the 5 breast cancer patients in the study.

| Patient Number | Cancer Type | Stage | Site of Metastasis | Check if Ongoing | Type of Treatment |
|---|---|---|---|---|---|
| 01-003 | BREAST | 3 C | LYMPH NODES LEFT CHEST WALL | Checked | CHEMOTHERAPY |
| 01-006 | BREAST | 4 | LYMPH NODES AND LIVER | Checked | CHEMOTHERAPY |
| 01-014 | BREAST | 4 | LYMPH NODES | Checked | CHEMOTHERAPY |
| 01-019 | BREAST | 4 | BONE LIVER | Checked | CHEMOTHERAPY |
| 02-017 | BREAST | 3 | LYMPH NODES | Not checked | RADIATION CHEMOTHERAPY |

TABLE 38

Current medications for the 5 breast cancer patients in the study.

| Patient Number | Drug name | Diagnosis associated with the treatment | Dose |
|---|---|---|---|
| 01-003 | BENADRYL | PRE-CHEMO MEDICATION | 25 MG Q 28 DAYS |
| 01-003 | DECADRON | PRE-CHEMO MEDICATION | 20 MG Q 28 DAYS |
| 01-003 | HERCEPTIN | BREAST CANCER CHEMO | 8 MG Q 28 DAYS |
| 01-003 | TAGAMET | PRE-CHEMO FOR BREAST CANCER | 300 MG Q 28 DAYS |
| 01-003 | TAXOTERE | BREAST CANCER CHEMO | 40 MG Q 28 DAYS |
| 01-003 | TYLENOL | PAIN | 1 GR Q 28 DAYS |
| 01-003 | ZOFRAN | PRE-CHEMO FOR BREAST CANCER | 32 MG Q 28 DAYS |
| 01-006 | DECADRON | PRE-MED FOR CHEMO | 20 MG Q 2 WEEKS |
| 01-006 | GEMZAR | CHEMO FOR BREAST CANCER | 1000 MG Q 2 WEEK |
| 01-006 | HERCEPTIN | CHEMO FOR BREAST CANCER | 100 MG Q WEEKS |
| 01-006 | KYTRIL | PRE-MED FOR CHEMO | 1 MG Q 2 WEEKS |
| 01-006 | TYLENOL | PRE MED | 1 GRAM Q 2 WEEKS |
| 01-014 | CARBOPLATIN | CHEMO FOR BREAST CANCER | 650 MG Q 21 DAYS |
| 01-014 | DECADRON | PRE-MED FOR CHEMO | 20 MG Q 21 DAYS |
| 01-014 | HERCEPTIN | CHEMO FOR BREAST CANCER | 270 MG Q 21 DAYS |
| 01-014 | ROCEPHIN | ANTIBIOTIC FOR FEVER | 1000 MG PRN |
| 01-014 | TAXOTERE | CHEMO FOR BREAST CANCER | 100 MG Q 21 DAYS |
| 01-014 | ZOFRAN | PRE-MED FOR CHEMO | 32 MG Q 21 DAYS |
| 01-019 | AREDIA | CHEMO FOR BREAST CANCER | 90 MG Q 21 DAYS |
| 01-019 | BENADRYL | PRE-MED FOR CHEMO | 25 MG Q 21 DAYS |
| 01-019 | CARBOPLATIN | CHEMO FOR BREAST CANCER | 580 MG Q 21 DAYS |
| 01-019 | DECADRON | PRE-MED FOR CHEMO | 20 MG Q 21 DAYS |
| 01-019 | KYTRIL | PRE-MED FOR CHEMO | 1 MG Q 21 DAYS |
| 01-019 | MORPHINE SULFATE | PRE-CHEMO | 2 MG PRN |
| 01-019 | TAGAMET | PRE-MED FOR CHEMO | 300 MG Q 21 DAYS |
| 01-019 | TAXOTERE | CHEMO FOR BREAST CANCER | 110 MG Q 21 DAYS |
| 01-019 | ZOCOR | HYPERCHOLESTEROLEMIA | 10 MG ONE QD |
| 02-017 | ADRIAMYCIN | BREAST CANCER | 79 MG QD 21 DAY |
| 02-017 | BENADRYL | ITCHING | 25 MG Q 21 DAYS |
| 02-017 | CYTOXEN | BREAST CANCER | 790 MG Q 21 DAY |
| 02-017 | DECADRON | NAUSEA | 20 MG Q 21 DAYS |
| 02-017 | VICODIN | CANCER PAIN | 325 MG TID PRN |
| 02-017 | ZOFRAN | NAUSEA & VOMITING | 32 MG Q 21 DAYS |

TABLE 40

Numbers of CTCs (per 7.5 ml) and relative EGFR phosphorylation levels for 5 breast cancer and 6 normal samples.

| Serial No. | Breast cancer Patient ID | CTC | Relative EGFR Level | Normal Patient ID | CTC | Relative EGFR Level |
|---|---|---|---|---|---|---|
| 1 | 01-014 | 3 | 0.7 | 02-007 | 0 | 1.14 |
| 2 | 01-003 | 1 | 1.26 | 01-013 | 0 | 1.31 |
| 3 | 01-019 | 4 | 0.88 | 01-011 | 0 | 1.2 |
| 4 | 01-006 | 1 | 3.27 | 01-015 | 1 | 0.68 |
| 5 | 02-017 | 3 | 2.44 | 02-012 | 0 | 1.32 |
| 6 |  |  |  | 02-013 | 0 | 0.68 |

TABLE 41

Numbers of CTCs (per 7.5 ml) and relative HER-2 phosphorylation levels for 5 breast cancer and 6 normal samples.

| Serial No. | Breast cancer Patient ID | CTC | Relative HER-2 Level | Normal Patient ID | CTC | Relative HER-2 Level |
|---|---|---|---|---|---|---|
| 1 | 01-014 | 3 | 0.66 | 02-007 | 0 | 1.13 |
| 2 | 01-003 | 1 | 1 | 01-013 | 0 | 1.15 |
| 3 | 01-019 | 4 | 0.94 | 01-011 | 0 | 1.31 |
| 4 | 01-006 | 1 | 2.52 | 01-015 | 1 | 0.76 |
| 5 | 02-017 | 3 | 2.14 | 02-012 | 0 | 1.07 |
| 6 |  |  |  | 02-013 | 0 | 0.59 |

Patient 01-019 tested positively for ER and negatively for PR and HER-2 overexpression in the primary tumor. This patient was not given Herceptin® and was being treated with Taxotere®+carboplatin at the time of the blood draw. Four CTCs were identified. None of these cells stained positively for EGFR expression by the Veridex CellSearch™ System. After stimulation of the isolated CTCs with ligand, there was no detectable phosphorylation of either EGFR or HER-2 in the proximity assays. These data inform the physician that the patient's tumor cells continue not to be driven by EGFR/HER-2 pathways, so there is no reason to change the current therapy.

There was no HER-2 test reported for patient 01-006, but she was presumably HER-2 positive since she was given Herceptin® therapy. The patient was negative for both ER and PR. Patient 01-006 had 1 CTC that was positive for EGFR expression by staining. There was significant activation of both EGFR and HER-2 detected. In spite of therapy that included Herceptin®, neither the EGFR and nor the HER-2 pathways were shut down. Activation may be resulting from formation of heterodimers between EFGR and HER-2, permitting evasion of Herceptin® inhibition. These data inform the physician that the therapy needs to be changed. Therapies that include agents targeting both EGFR and HER-2, such as lapatinib, Herceptin®+ZACTIMA™, Herceptin®+Erbitux®, Herceptin®+Iressa®, or Herceptin®+Tarceva®, would be indicated.

Patient 02-017 tested negatively for ER, PR, and HER-2 overexpression in the primary tumor. The patient had previously been treated with adriamycin+cytoxen, but at the time of blood collection was not on cancer therapy. The sample contained 3 CTCs, all of which stained positively for EGFR expression. There was significant activation of both EGFR and HER-2 detected in the proximity assays. Although the primary tumor of this patient was negative for HER-2 overexpression, the EGFR/HER-2 pathways were active. Treatment with Herceptin®, either alone or in combination with chemotherapeutics, or chemotherapeutics alone would not have been an adequate therapy for this patient. These data inform the physician that therapy including agents that target both EGFR and HER-2, such as lapatinib, Herceptin®+ZACTIMA™, Herceptin®+Erbitux®, Herceptin®+Iressa®, or Herceptin®+Tarceva®, are indicated.

The primary tumors of patients 01-003 and 01-014 were reported in the patient histories as positive for HER-2 overexpression. Both patients were negative for ER and PR. Patient 01-003 was being treated with Herceptin® and Taxotere®, and patient 01-014 was being treated with Herceptin®, carboplatin and Taxotere®. Patient 01-003 had 1 CTC which was negative for EGFR expression by staining. There was no phosphorylation of either EGFR or HER-2 detected. These data inform the physician that the HER-2 driven pathway detected originally in the primary tumor is no longer active. Given that the percentage of primary tumor actually staining with HER-2 antibody in a positively scored primary tumor is frequently ~10%, it is not unexpected that CTCs associated with recurrence may not be overexpressing HER-2. The EGFR pathway is not active. There is no reason to treat this patient with targeted therapies directed against either EGFR or HER-2. Patient 01-014 had 3 CTCs, all of which stained positively for EGFR expression. There was no phosphorylation of either EGFR or HER-2 detected for this patient. Despite the fact that CTCs showed EGFR expression, the EGFR pathways were not active. Lower levels of EGFR, in the absence of HER-2, may not be high enough to activate the cancer cells. Again, there is no reason to treat this patient with targeted therapies directed against either EGFR or HER-2.

Table 42 shows a summary of the diagnostic information for each patient and the recommendations for therapy.

TABLE 42

Summary of diagnostic information on the 5 breast cancer patients in the study with resultant therapy indications.

| Patient # | ER status | PR status | HER-2 status | CTC # | CTC EGFR | pEGFR | pHER-2 | Therapy indicated (chemotherapy may be added in combination) |
|---|---|---|---|---|---|---|---|---|
| 01-019 | Positive | Negative | Negative | 4 | Negative | Negative | Negative | hormonal therapy |
| 01-006 | Negative | Negative | Unknown | 1 | Positive | Positive | Positive | lapatinib, Herceptin ® + ZACTIMA ™, Herceptin ® + Erbitux ®, Herceptin ® + Iressa ®, Herceptin ® + Tarceva ® |
| 02-017 | Negative | Negative | Negative | 3 | Positive | Positive | Positive | lapatinib, Herceptin ® + ZACTIMA ™, Herceptin ® + Erbitux ®, Herceptin ® + Iressa ®, Herceptin ® + Tarceva ® |

TABLE 42-continued

Summary of diagnostic information on the 5 breast cancer patients in the study with resultant therapy indications.

| Patient # | ER status | PR status | HER-2 status | CTC # | CTC EGFR | pEGFR | pHER-2 | Therapy indicated (chemotherapy may be added in combination) |
|---|---|---|---|---|---|---|---|---|
| 01-003 | Negative | Negative | Positive | 1 | Negative | Negative | Negative | (no EGFR +/or HER-2 inhibitors) |
| 01-014 | Negative | Negative | Positive | 3 | Positive | Negative | Negative | (no EGFR +/or HER-2 inhibitors) |

Example 12

A Novel Assay to Quantitate p95ErbB2 and Other Truncated Receptor Tyrosine Kinases or Proteins from Clinical Samples HER-2, also known as ErbB2, is one of four members (HER-1, HER-2, HER-3, and HER-4) of the epidermal growth factor receptor or HER family. All HER receptors share a similar structure: an extracellular ligand-binding domain; a short hydrophobic transmembrane region; and a cytoplasmic tyrosine kinase domain. Hetero- or homodimerization of HER receptors, induced by ligand binding or receptor overexpression, leads to the activation of the receptor kinase and to the subsequent phosphorylation of several tyrosine residues. In turn, these phosphorylated tyrosine residues, located within the carboxyl terminus of the receptors, recruit mediator molecules and activate signaling pathways leading to modification of cell growth, differentiation, and survival. ErbB2 is overexpressed/amplified in approximately 15% to 25% of human breast cancers, and its overexpression/amplification is associated with an aggressive phenotype.

Trastuzumab (Herceptin®), a recombinant humanized monoclonal antibody that binds with high affinity to the extracellular domain of ErbB2, provides substantial clinical benefits in patients with ErbB2-overexpressing or ErbB2-gene-amplified advanced breast cancer and improves survival when it is combined with chemotherapy. In addition, Herceptin® has been recently shown to improve relapse-free survival and overall survival in patients with ErbB2-overexpressing early breast cancer.

However, 70% to 80% of patients with ErbB2-overexpressing breast cancer do not respond to Herceptin® when given as single agent therapy due to either primary or acquired resistance. There are several potential mechanisms for Herceptin® resistance, which include: inactivation or loss of phosphatase and tensin homolog deleted on chromosome 10 (PTEN); activation of other tyrosine kinase receptors, including the insulin-like growth factor receptor (IGF-1R); and accumulation of truncated forms of the ErbB2 receptor that lack the amino terminal extracellular Herceptin®-binding domain.

The truncated ErbB2 polypeptides containing only cytosolic carboxyl terminal fragments, collectively known as p95ErbB2 or C-terminal fragments, are frequently found in ErbB2-expressing breast cancer cell lines and tumors. In fact, these fragments are the predominant ErbB2 forms in some tumors. These fragments arise through the proteolytic processing of the extracellular domain of full-length ErbB2 or by alternative initiation of translation from two methionine residues (amino acids 611 or 687) that are located before and after the transmembrane domain, respectively.

The biological function of p95ErbB2 has not been fully characterized, although overexpression of p95ErbB2 has been shown to lead to growth of tumor xenografts in nude mice. The p95ErbB2 protein has kinase activity, and this activity is required for tumor growth. The fact that the truncated receptor p95ErbB2 has kinase activity in the absence of the Herceptin®-binding extracellular domain suggests that p95ErbB2-expressing tumors may be resistant to Herceptin® but sensitive to the inhibitory effects of pan-HER inhibitors such as, for example, lapatinib (a low molecular weight tyrosine kinase inhibitor of ErbB2 that has activity in patients with ErbB2-expressing tumors resistant to Herceptin®). Early clinical data indicates that 8 out of 9 patients expressing p95ErbB2 are resistant to Herceptin®. It has also been recently demonstrated that acquired resistance to pan-HER tyrosine kinase inhibitors and Herceptin® occurs through either a feedback mechanism leading to overexpression of ErbB3 or possible truncation of ErbB2, leading to formation of p95ErbB2.

Since Herceptin® inhibits ErbB2 truncation, a combination of Herceptin® with pan-HER tyrosine kinase inhibitors may be ideal to treat patients with acquired resistance to Herceptin® and/or pan-HER tyrosine kinase inhibitors.

With respect to current methods for the detection of p95ErbB2, the presence of p95ErbB2 in human breast tumors can be detected by Western blot analysis. However, this technique requires a large amount of fresh-frozen tumor tissue, a serious limitation because such tissue is rarely available from clinical samples. Immunoflourescence-based p95ErbB2 detection assays can be performed on routine formalin-fixed paraffin-embedded tissue sections from clinical samples. This technique builds from the observation that p95ErbB2, but not full-length ErbB2, is localized both to the cytoplasm and the cell membrane. The method uses an anti-ErbB2 antibody which targets the intracellular domain and relies on differential cytoplasmic staining However, immunofluorescence-based methods have limited sensitivity (~10,000 receptors per cell) and cannot detect the low levels of p95ErbB2 which drive tumor proliferation. In addition, the functional p95ErbB2 polypeptide is located on the cell membrane and not in the cytoplasm. Furthermore, it is difficult to differentiate between internalized ErbB2 in the cytoplasm and p95ErbB2 in the cytoplasm.

The novel, ultra-sensitive, and highly specific assay method described herein overcomes the limitations of current methods for the detection of p95ErbB2 and can be used on a wide variety of clinical samples such as fine needle aspirates, core biopsies, and circulating tumor cells (CTCs) obtained from blood. In addition to measuring p95ErbB2, the method of the invention is capable of detecting the activation of all four members of the ErbB family along with PTEN and IGF-1R from minute amounts of biological material.

Exemplary Methods

Figure 13:
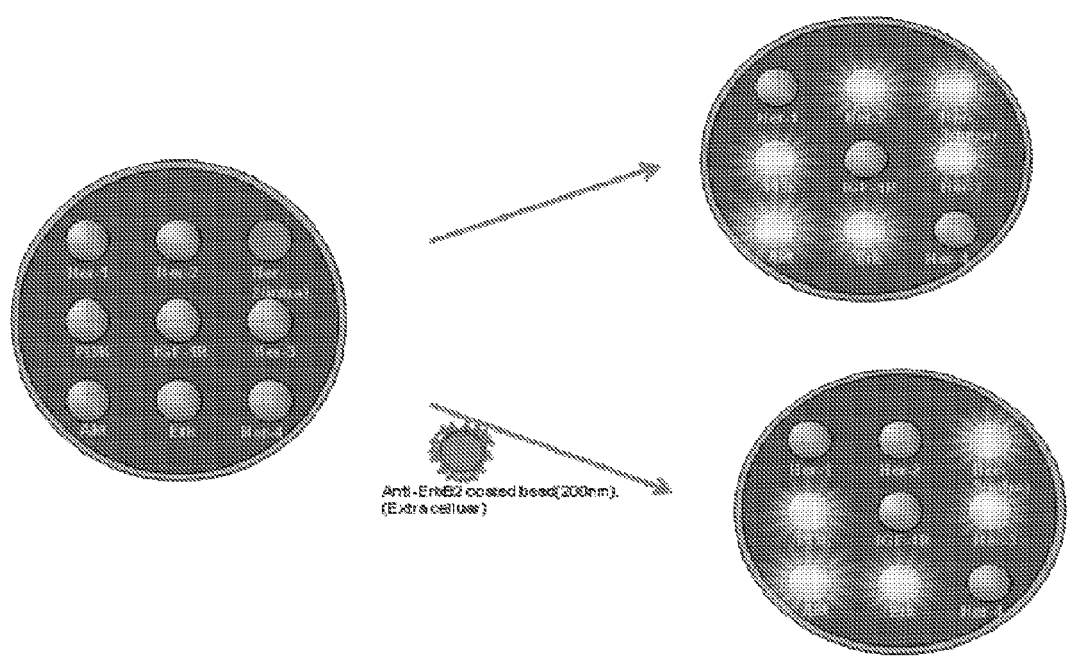
FIG. 13 shows that full-length HER-2 (ErbB2) can be removed from a patient sample using antibodies which bind to the extracellular domain of ErbB2 attached to a polystyrene bead or a polymeric dextran.

FIG. 13 shows that full-length ErbB2 can be removed from clinical samples using antibodies which bind to the extracellular domain of ErbB2 attached to a polystyrene bead or a polymeric dextran. The assay takes advantage of the rapid solution phase binding kinetics, the selective extraction of full-length protein by receptor antibodies bound to the beads, and the inability of bead-bound protein to bind to a planar array. Alternatively, magnetically charged beads can be used to retain full-length ErbB2 behind and only truncated p95ErbB2 would be applied to a microarray.

Assay method "A" below illustrates the detection of p95ErbB2 using a high sensitivity and specificity proximity assay. Assay method "B" below illustrates the detection of p95ErbB2 using a single antibody. These methods for detecting truncated proteins can be applied to a number of different proteins including, but not limited to, p95ErbB2, the EGFR V111 mutant (implicated in glioblastoma, colorectal cancer, etc.), other truncated receptor tyrosine kinases, caspases, and the like.

A. Proximity Dual Detection of Truncated Receptors Using Microarray ELISA with Tyramide Signal Amplification.

This example illustrates a multiplex, high-throughput, proximity dual detection microarray ELISA having superior dynamic range that is suitable for detecting truncated receptors such as p95ErbB2 in rare circulating cells:

1) Capture antibodies are printed on a 16-pad FAST slide (Whatman Inc.) with a serial dilution ranging from 1 mg/ml to 0.004 mg/ml.
2) After drying overnight, the slide is blocked with Whatman blocking buffer.
3) 80 µl of BT474 cell lysate with or without anti-ErbB2 (extracellular) antibody coated beads is added onto each pad with a 10-fold serial dilution. The slide is incubated for two hours at room temperature.
4) After six washes with TBS-Tween, 80 µl of detection antibodies for the proximity assay diluted in TBS-Tween/2% BSA/1% FBS is added to the slides. The detection antibodies used are: (1) an anti-ErbB2 antibody specific for the intracellular domain of ErbB2 that is directly conjugated to glucose oxidase (GO); and (2) a monoclonal antibody recognizing phosphorylated ErbB2 that is directly conjugated to horseradish peroxidase (HRP). The incubation is for 2 hours at room temperature.
5) For signal amplification, 80 µl of biotin-tyramide at 5 µg/ml is added and reacted for 15 minutes along with 50 mM glucose. The slide is washed six times with TBS-Tween, twice with 20% DMSO/TBS-Tween, and once with TBS. 80 µl of SA-Alexa 555 is added and incubated for 30 min. The slide is then washed twice, dried for 5 minutes, and scanned on a microarray scanner (Perkin-Elmer, Inc.).
6) As a non-limiting example, slide 1 can report on total ErbB2 activation while slide 2 can report on truncated ErbB2 activation. Based on the amount of activated or total truncated ErbB2 in the sample, appropriate therapy can be selected.

B. Detection of Truncated Receptors Using Microarray ELISA with Tyramide Signal Amplification.

This example illustrates a multiplex, high-throughput, single detection microarray ELISA having superior dynamic range that is suitable for detecting truncated receptors such as p95ErbB2 in rare circulating cells:

1) Capture antibodies are printed on a 16-pad FAST slide (Whatman Inc.) with a serial dilution ranging from 1 mg/ml to 0.004 mg/ml.
2) After drying overnight, the slide is blocked with Whatman blocking buffer.
3) 80 µl of BT474 cell lysate with or without anti-ErbB2 (extracellular) antibody coated beads is added onto each pad with a 10-fold serial dilution. The slide is incubated for two hours at room temperature.
4) After six washes with TBS-Tween, 80 µl of detection antibodies for the assay diluted in TBS-Tween/2% BSA/1% FBS is added to the slides. The detection antibody used is an anti-ErbB2 antibody specific for the intracellular domain of ErbB2 that is directly conjugated to HRP. The incubation is for 2 hours at room temperature.
5) For signal amplification, 80 µl of biotin-tyramide at 5 µg/ml is added and reacted for 15 minutes along with 1 mM hydrogen peroxide. The slide is washed six times with TBS-Tween, twice with 20% DMSO/TBS-Tween, and once with TBS.
6) 80 µl of SA-Alexa 555 is added and incubated for 30 min. The slide is then washed twice, dried for 5 minutes, and scanned on a microarray scanner (Perkin-Elmer, Inc.).
7) As a non-limiting example, slide 1 can report on total ErbB2 activation while slide 2 can report on truncated ErbB2 activation. Based on the amount of activated or total truncated ErbB2 in the sample, appropriate therapy can be selected.

One embodiment of the present invention for detecting a truncated receptor such as p95ErbB2 is shown in FIG. 14. FIG. 14A shows that beads coated with an antibody directed to the extracellular domain (ECD) of a receptor of interest binds the full-length receptor but not the truncated receptor to remove any full-length receptor from the assay. FIG. 14B shows that the truncated receptor, once bound to a capture antibody, may then be detected by a detection antibody that is specific for the intracellular domain (ICD) of the full-length receptor. The detection antibody may be directly conjugated to horseradish peroxidase (HRP). Tyramide signal amplification (TSA) may then be performed to generate a signal to be detected.

Figure 15:
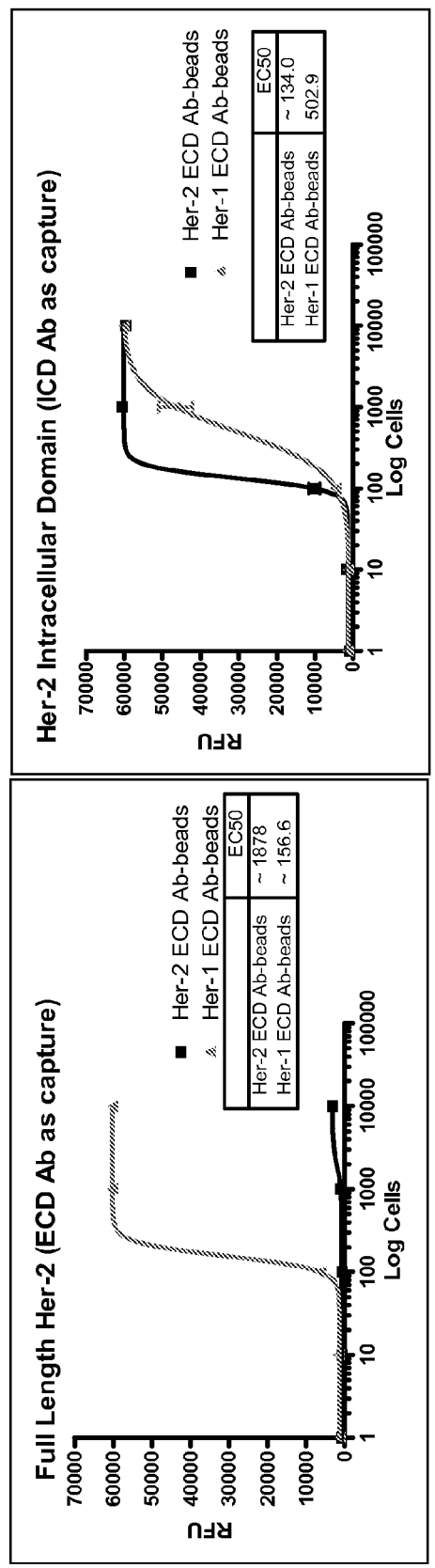
FIG. 15 shows that pretreatment with beads coated with an antibody directed to the extracellular domain (ECD) of ErbB2 (HER-2) almost completely removed the full-length ErbB2 signal without affecting the ErbB2 intracellular domain (ICD) signal.

With regard to p95ErbB2, FIG. 15 shows that pretreatment with beads coated with an antibody directed to the extracellular domain (ECD) of ErbB2 (HER-2) almost completely removed the full-length ErbB2 signal without affecting the ErbB2 intracellular domain (ICD) signal. The decrease of the full-length ErbB2 signal was dependent on the concentration of HER-2 ECD antibody-coupled beads that was used in the assay as increasing the amount of antibody-coupled beads from 4 µg/ml to 12 µg/ml decreased the full-length ErbB2 signal from 9.59% to 2.84%.

Figure 16:
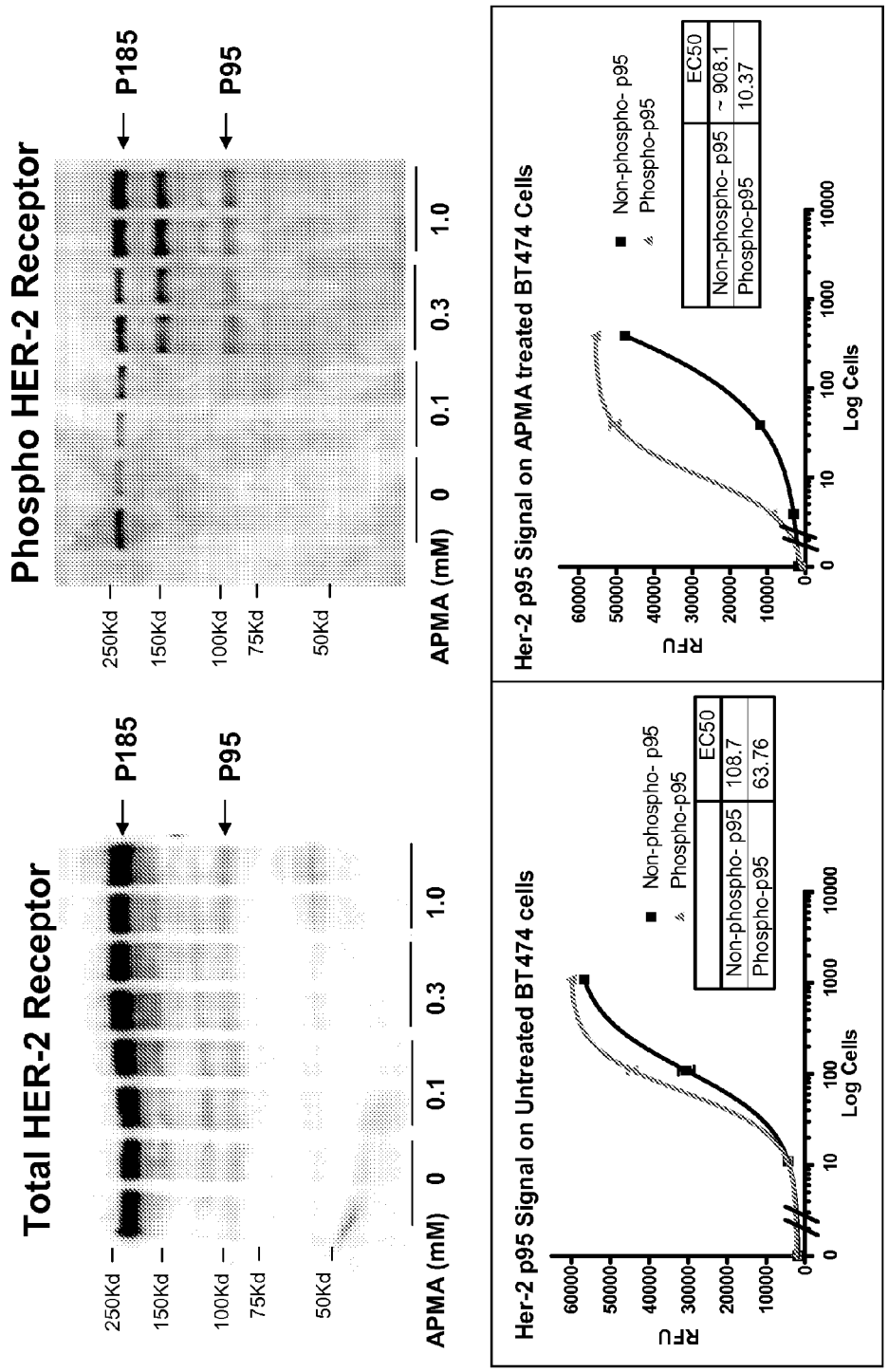
FIG. 16 shows that APMA ((4-aminophenyl)mercuric acetate) treatment increased p95ErbB2 phosphorylation in BT-474 cells.
Figure 17:
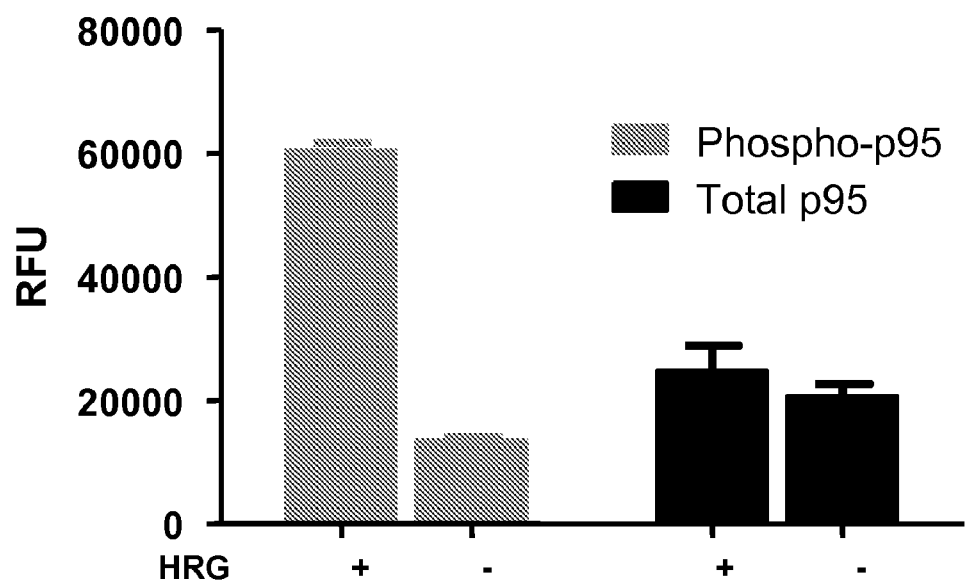
FIG. 17 shows that heregulin increased p95ErbB2 phosphorylation in T47D cells.

FIGS. 16 and 17 confirm that p95ErbB2 was specifically detected using the assay methods described above. As shown in FIG. 16, APMA ((4-aminophenyl)mercuric acetate) treatment increased p95ErbB2 phosphorylation in BT-474 cells. FIG. 17 shows that heregulin increased p95ErbB2 phosphorylation in T47D cells.

Accordingly, the methods described above for detecting truncated proteins such as p95ErbB2 in a patient sample provide at least the following advantages over methods that are currently available:

1) Higher sensitivity, providing the ability to detect truncated receptors from single cells.
2) Higher specificity.
3) The ability to report on an entire pathway using multiplexed microarrays instead of a single protein.
4) Scalability.

Example 13

Selection of Patients for Treatment Having Stage I or Stage II Lymph-Node-Negative Invasive Breast Cancer After Identification of Risk of Recurrence by a Gene Expression Panel Panels of gene expression markers have been developed that predict the likelihood of breast cancer prognosis and/or recurrence in various populations of women with, for example, node-negative disease. These gene panels can be useful for identifying women who are unlikely to experience recurrence and thus are unlikely to benefit from adjuvant chemotherapy. The expression panels can be used to identify women who can safely avoid adjuvant chemotherapy, without negatively affecting disease-free and overall survival outcomes. Suitable systems include, but are not limited to, Oncotype DX™, which is a 21-gene panel from Genomic Health, Inc. (Redwood City, Calif.); MammaPrint®, which is a 70-gene panel from Agendia (Amsterdam, Netherlands); and a 76-gene panel from Veridex (Warren, N.J.). These panels can be used in conjunction with the analysis of pathway activation to determine the need to include chemotherapy with the appropriate targeted therapies selected using the methods described in previous Examples.

The following protocol provides an exemplary embodiment of the present invention wherein gene expression profiling is used in conjunction with activation state profiling to select the appropriate targeted therapy or combination of targeted therapies for the treatment of breast cancer:

1) A tumor sample with a minimum thickness of 3 mm and a maximum thickness of 5 mm is collected using a biopsy punch. The biopsy is placed directed into the sample tube containing RNARetain™ preservative. The tube is shipped immediately to Agendia for testing using the MammaPrint® assay.
2) The test report from Agendia assigns the patient to either a "good" signature/low-risk group or a "poor" signature/high-risk group. If the patient is in the low-risk group, she can safely avoid adjuvant chemotherapy without negatively affecting disease-free and overall survival.
3) The MammaPrint assay is applicable for patients who are either ER positive or ER negative. Once the ER and ErbB2 status is determined, the patient is assigned to one of the subclasses of breast cancer described in Example 8. The four major subclasses are as follows:
    1. ER+/PR+/ErbB2−
    2. ER+/ErbB2+
    3. ER−/ErbB2+
    4. ER−/PR−/ErbB2
4) Tumor cells (e.g., CTCs) are isolated from blood and prepared for analysis as described in Example 1. Alternatively, a portion of the biopsy can be used to prepare a tumor cell extract as described in Example 2. The cell preparations are assayed as described in either Example 3 or Example 4. The activation profile is evaluated in a similar manner as described in Example 8 (Tables 4-22), Example 9 (Tables 23-31), and Example 10 (Tables 32-35). The appropriate targeted therapy or combination of targeted therapies is selected. If the patient is in the low-risk group, no chemotherapy is added. If the patient is in the high-risk group, chemotherapy selected by the physician based on clinical information is added to the targeted therapies.

Example 14

Selection of Patients for Treatment After Determination of Primary Tissue of Origin by a Gene Expression Panel Approximately 3% to 5% of all metastatic tumors are classified into the category of cancer of unknown primary (CUP). Correct diagnosis of the tissue of origin is important in treatment decisions because current therapies are based largely on anatomical site. Gene expression panels can be useful in identifying women with metastatic cancer who would benefit from therapy consistent with that given to women diagnosed initially with breast cancer. Suitable systems include, but are not limited to, the Rosetta Genomics CUP assay, which classifies cancers and tissues of origin through the analysis of the expression patterns of microRNAs (see, e.g., PCT Publication No. WO 08/117278); the Aviara DX (Carlsbad, Calif.) CancerTYPE ID™ assay, an RT-PCR-based expression assay that measures 92 genes to identify the primary site of origin for 39 tumor types; and the Pathwork™ Tissue of Origin Test (Sunnyvale, Calif.), which measures the expression of more than 1600 genes on a microarray and compares a tumor's gene expression "signature" against those of 15 known tissue types. Once the patient has been identified with breast as the tissue of primary cancer, pathway activation profiles can be used to select the appropriate targeted therapies to include in the treatment schedule.

The following protocol provides an exemplary embodiment of the present invention wherein gene expression profiling is used in conjunction with activation state profiling to select the appropriate targeted therapy or combination of targeted therapies for the treatment of breast cancer:

1) Two or more glass slides with 7 μm thick sections of a tissue removed, either surgically or by fine needle biopsy, from a metastatic tumor are obtained from the patient. These cells are fixed in formalin and embedded in paraffin (FFPE). One additional H&E stained slide of the same tumor is stained with H&E.
2) A pathologist reviews the H&E slide and indicates the area to be collected for the CancerTYPE ID™ assay. The slides are sent to Aviara DX for analysis.
3) The test report from Aviara DX indicates the top 5 most probable sites of origin as determined from a k-nearest neighbor analysis and a prediction is derived. If the prediction for the patient is for breast as the tumor of unknown origin, the patient's tumor cells can be assessed for pathway activation.
4) Tumor cells (e.g., CTCs) are isolated from blood and prepared for analysis as described in Example 1. Alternatively, a fine needle biopsy can be used to prepare a tumor cell extract as described in Example 2. The cell preparations are assayed as described in either Example 3 or Example 4. The activation profile is evaluated in a similar manner as described in Example 8 (Tables 4-22), Example 9 (Tables 23-31), and Example 10 (Tables 32-35). The appropriate targeted therapy or combination of targeted therapies is selected.

Example 15

Novel Set of Breast Cancer Tests Using Proximity Assays

Background:
In 2008, an estimated 182,460 new cases of invasive breast cancer will be identified among women in the U.S. Approximately 20% of women with breast cancer have an overexpression of HER-2 at the time of diagnosis. HER-2-overexpressed (HER-2-positive) breast cancers are associated with more aggressive forms of cancer and therefore result in poorer survival rates and higher recurrence rates. HER-2-positive patients are often treated with the monoclonal antibody drug trastazumab (Herceptin®). However, Herceptin® is an expensive and potentially cardio-toxic treatment; therefore, accurate identification of candidates is imperative to optimize clinical outcomes. Herceptin® works by blocking HER-2 and therefore reduces tumor cell growth. Lapatinib (Tykerb®) is a small molecule kinase inhibitor often used for patients who have failed Herceptin® therapy.

Current HER-2 Testing Options:

HER-2 status is typically assessed by either or both: (1) receptor protein testing using an immunohistochemistry assay (IHC); or (2) gene amplification using a fluorescence in situ hybridization (FISH) test technique. However, there is widespread recognition that current testing methods lack accuracy and can be highly variable from lab to lab and can vary according to differences in specimen handling before it is received in the lab. In fact, available evidence suggests that about 20% of current HER-2 testing may be inaccurate (ASCO/CAP Guidelines for HER-2 Testing in Breast Cancer, *J. Clin. Oncology* (2007)).

Proximity Assay-Based Breast Cancer Tests:

The novel set of breast cancer tests described in this example takes advantage of the multiplex, high-throughput proximity (i.e., three-antibody) assays described herein. Such diagnostic testing will be particularly useful in determining the expression and activation of HER-2 in circulating tumor cells (CTCs) or fine needle aspirate (FNA) collected from patients with breast cancer, and will aid in therapy selection for breast cancer patients.

The following protocol describes the standard format used for all the tests set forth in this example:

1. Collect blood sample:
    a. Collect two 7.5 mL tubes of blood.
    b. Use the Veridex Epithelial Cell Adhesion Molecule (EpCAM) magnetic beads with binding proteins specific to epithelial cells to separate circulating tumor cells (CTCs) from other blood components.
    c. Wash the sample.
2. Activate one sample (only live cells will be activated) and lyse those cells.
3. Lyse the other sample's cells.
4. (This is the step that is variable between each of the tests) Use of proximity microarray assays to detect two proteins (e.g., signal transduction proteins) and cytokeratin in the activated sample to quantify total activated proteins and cytokeratin:
    a. Three monoclonal antibodies, specific to the two proteins and cytokeratin (CK), are fixed to the microarray.
    b. The sample is poured over the microarray chip, allowing for the analytes to bind to the monoclonal antibodies specific for them.
    c. A mixture of six additional monoclonal antibodies is poured over the microarray chip (two monoclonal antibodies per analyte). In order for fluorescence to occur at the site of an analyte, all three specific monoclonal antibodies (the one fixed antibody and the two poured antibodies) must bind to that analyte.
5. Protein microarray analysis of the two proteins in the inactivated sample to quantify total protein.
6. Each activated protein result is calibrated with the inactivated sample. This will yield quantitative protein results with a "+" or "−" result for each of the three analytes.

Product A [Herceptin®]: This test is a baseline ErbB activation assay to detect HER-2 activation/phosphorylation. This test is also an enhanced ErbB activation assay for use in Stage III and IV patients to determine HER-2 discordance. Proximity microarray assays are performed to detect ErbB1/HER-1, ErbB2/HER-2, and cytokeratin in the activated sample to quantify total activated proteins and cytokeratin. Monoclonal antibodies against ErbB1/HER-1 and ErbB2/HER-2 are used, while a pancytokeratin antibody for epithelial cells is used. The quantitative signal describes levels of HER-2 and HER-1 protein activation and expression. The relative activation score is derived from a ratio of phosphorylation to expression. The test quantifies: HER-2 activation (phosphorylation); HER-2 expression; HER-1 activation (phosphorylation); HER-1 expression; and pancytokeratin (for cell number normalization). The test has high sensitivity since HER-2 activation is detected in single circulating tumor cells. The test also has a specificity of ≧99% as measured by cross-reactivity of less than 1% with other markers. Reproducibility (intra assay): CV=5-15%. Reproducibility (inter assay): CV=10-20%. The test report provides the following: (1) HER-2 and HER-1 phosphorylation, reported as a quantitative amount and as positive or negative; (2) HER-2 and HER-1 expression, reported as a quantitative amount and as positive or negative; and (3) cytokeratin quantitation. If HER-1 or HER-2 levels are normal but cytokeratin levels are high, this would diagnose breast cancer but not indicate the use of HER-1 or HER-2 targeted therapies.

Product B [Tykerb® Rule-in Test]: This test is an enhanced ErbB activation assay that includes detection of p95HER-2 and EGFR. In particular, this is a rule-in test for lapatinib (Tykerb®) therapy for HER-2-positive patients failing treatment with Herceptin®. This test aids in the selection and monitoring of Herceptin® patients, and in switching patients from Herceptin® to Tykerb® therapy. Proximity microarray assays are performed to detect ErbB1/HER-1, p95HER-2, and cytokeratin in the activated sample to quantify total activated proteins and cytokeratin. Monoclonal antibodies against ErbB1/HER-1 and p95HER-2 are used, while a pancytokeratin antibody for epithelial cells is used. The test quantifies: p95-HER-2 activation (phosphorylation); p95-HER-2 expression; HER-1 activation (phosphorylation); HER-1 expression; and pancytokeratin (for cell number normalization). This test may be validated in a clinical trial of metastatic patients with p95-HER-2 disease who were previously assigned as HER-2-positive based on IHC or FISH and who failed Herceptin®. Patients who demonstrate activation of p95-HER-2 and HER-1 based on the proximity assay can be treated with Tykerb®. The trial will show a benefit in overall survival among p95-HER-2-positive patients treated with Tykerb®. Because p95HER-2 lacks the Herceptin®-binding extracellular domain of HER-2, high p95HER-2 levels would rule out Herceptin® and indicate the use of Tykerb® instead. However, if HER-1 or HER-2 levels are normal but cytokeratin levels are high, this would diagnose breast cancer but not indicate the use of HER-1 or HER-2 targeted therapies.

Figure 18:
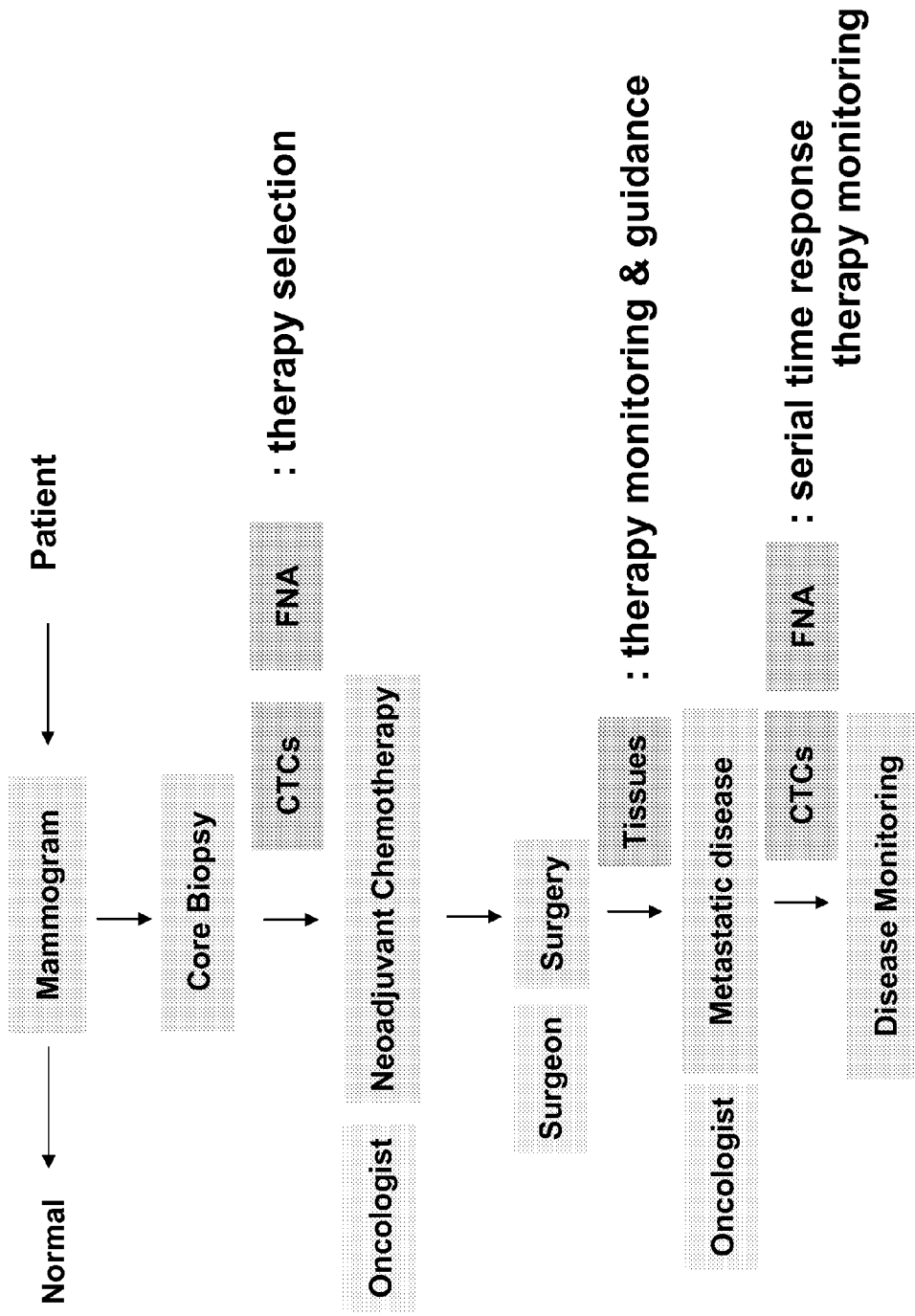
FIG. 18 shows multiple points in which the methods of the present invention may be used to influence clinical practice with respect to selecting the appropriate breast cancer therapy for a particular patient.

FIG. 18 illustrates multiple points in which the methods of the present invention may be used to influence clinical practice with respect to selecting the appropriate breast cancer therapy for a particular patient.

Example 16

Preparation of Sulfhydryl-Activated Dextran

This example describes a protocol to incorporate free sulfhydryl groups into a dextran molecule. As illustrated in Example 17, the sulfhydryl-modified dextran molecules may be used to prepare conjugates with an antibody and glucose oxidase (GO) for use in the single detection and proximity assays described herein. In some embodiments, a sulfhydryl-activated 500 kDa dextran molecule may be conjugated to an antibody and GO such that the ratio of antibody:GO:dextran is 2:12:1. The conjugation of a sulfhydryl-activated 500 kDa dextran molecule to the antibody and GO advantageously enhances sensitivity of the assay about 10-fold. In other embodiments, a sulfhydryl-activated 70 kDa dextran molecule may be conjugated to an antibody and horseradish peroxidase (HRP).

Definitions and Acronyms:
1. Dextran=a glucose polymer
2. Hydrochloric Acid=HCl
3. N-(3-Dimethylaminopropyl)N'-ethylcarbodiimide Hydrochloride=EDC
4. Phosphate Buffered Saline=PBS
5. Sodium Hydroxide=NaOH
6. 2-Morpholinoethanesulfonic Acid=MES
7. Ethylenediaminetetraacetic Acid=EDTA Instruments and Equipment:
1. Water Bath (Fisher, Isotemp 210)
2. ELISA Plate Reader (Molecular Devices, SpectraMAX1900)
3. ELISA Plate Washer (Nunc, Nunc-Immuno Wash 8)
4. Vortex Mixer (Fisher, Vortex Mixer)
5. Lyophilizer (Virtis, Freezemobile 12)
6. Centrifuge (Beckman, GS-6R)
7. Magnetic Stirrer (Corning, PC-410D)
8. Equipment to generate NANOpure Water (Barnstead, NANOpure DIamond)
9. Dialysis Cassette (Pierce, 66380)

Reagents, Chemicals, and Supplies:
1. 500 kDa Dextran (Fisher, BP1580-100)
2. Bromoacetic Acid (Sigma, 259357)
3. Sodium Hydroxide (Fisher, S318-500)
4. Isopropanol (Fisherr, A451-4)
5. 12N Hydrochloric Acid (Fisher, A144-500)
6. Cysteamine (Sigma, M9768)
7. N-(3-Dimethylaminopropyl)N'-ethylcarbodiimide Hydrochloride (Pierce, 22980)
8. Phosphate Buffered Saline (Cellgro, 21-040-CV)
9. 0.5M Ethylenediaminetetraacetic Acid solution (GIBCO, 15575-038)
10. 2-Morpholinoethanesulfonic Acid (Fluka, 69892)
11. 10× Phosphate Buffered Saline (Fisher, BP399-500)

Buffers and Solutions:
1. 2.9M NaOH: Dissolve 5.8 g sodium hydroxide in 50 mL Nanopure water.
2. 50 mM MES buffer solution: Dissolve 5.33 g 2-Morpholinoethanesulfonic Acid in 500 mL NANOpure water and adjust the pH to 4.5 using 12N HCL.
3. Dialysis Buffer: Add 10 mL 0.5M EDTA solution and 100 mL of 10×PBS to 890 mL Nanopure water to make final concentration of 5 mM EDTA in PBS.

Procedure:

Incorporation of Carboxyl Groups to Dextran:
1. To one gram of 500 kDa dextran (2 μmol) dissolved in 8.5 mL of 2.9M NaOH in a 50 mL polypropylene screw capped test tube is added 850 mg of bromoacetic acid. After thorough mixing by vortexing, the tube is incubated in a 50° C. water bath overnight.
2. After incubation, isopropanol is added to the reaction mixture to a final concentration of 70% (vol/vol) to precipitate the carboxylated dextran. After mixing with a vortex mixer, the solution is spun at 3000 rpm in a Beckman centrifuge at room temperature for 15 min and the supernatant discarded.
3. The precipitate is re-dissolved in 10 mL Nanopure water and the precipitation with isopropanol repeated two to three more times until no precipitation with added isopropanol is obtained. The clear 70% isopropanol solution is then adjusted to pH 4 with 12N HCl with vortexing to re-generate the precipitate and the mixture is again spun at 3000 rpm in the Beckman centrifuge for 15 min to precipitate the carboxylated dextran and the supernatant discarded.
4. To remove the residual bromoacetic acid, the precipitate is re-dissolved in 10 mL Nanopure water and the pH of the solution adjusted to 4 with HCL. Isopropanol is then added to 70% by volume to precipitate the carboxylated dextran. After mixing in a vortex mixer, the solution is spun at 3000 rpm in a Beckman centrifuge for 15 min and the supernatant discarded. This washing process was repeated for a total of three times.
5. After the last washing, the precipitate is dissolved again in 10 mL Nanopure water and the solution lyophilized to dryness in the lyophilizer to remove the HCl.
6. The lyophilized carboxylated dextran is stored at −70° C.

Conversion of the Carboxyl Groups on the Carboxylated Dextran to Sulfhydryl Groups:
1. Dissolve 10 mg of the lyophilized carboxylated dextran in 0.5 mL of 50 mM MES buffer, pH 4.5 in a 2 mL brown glass tube.
2. To the carboxylated dextran solution is added 1.42 mg of EDC and the mixture stirred at 40 C for 30 min.
3. Ten milligram of cysteamine is then added to the mixture and the resulting solution stirred for one more hour at 4° C.
4. After stirring, the mixture is transferred to a 0.5-3.0 mL dialysis cassette with a molecular weight cut-off of 10,000 and dialyzed against 500 mL of PBS, pH 7.4, at 4° C. overnight.
5. The dialysis buffer is then changed to 5 mM EDTA/PBS and dialyzed for another two hours. The dialysis process is repeated one more time.
6. The total number of sulfhydryl groups incorporated into each 500 kDa dextran molecule is determined by Ellman's Assay.
7. Fifty microliter aliquots of the sulhydryl-incorporated dextran solution are prepared in 1 mL Eppendorf tubes and the aliquots lyophilized. The lyophilized aliquots are kept at −70° C. for storage.

Example 17

Preparation of a HER-2 Antibody-Glucose Oxidase-Dextran Conjugate

This example describes a procedure to conjugate an extracellular domain-directed HER-2 antibody and glucose oxidase (GO) to a sulfhydryl-activated 500 kDa dextran molecule. The HER-2 antibody-GO-dextran conjugate may be used in the single detection and proximity assays described herein.

Definitions and Acronyms:
1. Succinimidyl-4-(N-Maleimidomethyl)cyclohexane-1-carboxyl-(6-amidocaproate)=LC-SMCC
2. Dimethyl Sulfoxide=DMSO
3. Sodium Hydroxide=NaOH
4. Concentrated Hydrochloric Acid=HCl
5. Phosphate Buffer Saline=PBS
6. Ethylenediaminetetraacetic Acid=EDTA
7. 2-(Ethylmercuriomercapto)benzoic Acid Sodium Salt=Thimerosal
8. HPLC=High Performance Liquid Chromatography Instruments and Equipment:
1. HPLC System (Agilent Technologies; Series 1100)
2. Size Exclusion Chromatography Column (Phenomenex; BioSep-SEC-S 3000)
3. Spectrophotometer (Hitachi; U-200)
4. Centrifuge (Beckman; GS-6R)
5. Magnetic Stirrer (Corning; PC-410D)
6. ELISA Plate Reader (Molecular Devices; Spectra MAX 190)
7. Vortex Mixer (Fisher Scientific; 02-215-365.)
8. Desalting Column (Pierce, 43230)
9. Centricon YM-10 Apparatus (Millipore, 4205)
10. 1 mL Pipette (Rainin, L-1000)
11. 200 µL Pipette (Rainin, L-200)
12. 20 µL Pipette (Rainin, L-20)
13. 2 µL Pipette (Rainin, L-2)
14. Multichannel Pipette (Rainin, L8-200)

Reagents, Chemicals, and Supplies:
1. Mouse Anti-human HER-2 Monoclonal Antibody at 1 mg/mL in PBS (Lab Vision; MS-301-PABX)
2. Dialized Glucose Oxidase (Prometheus)
3. Sulfhydryl-activated Dextran (Prometheus)
4. LC-SMCC=Succinimidyl-4-(N-Maleimidomethyl)cyclohexane-1-carboxyl-(6-amidocaproate) (Fisher; 22362)
5. DMSO=Dimethyl Sulfoxide (Sigma; D2650)
6. Bovine Serum Albumin (Sigma; A3294)
7. Sodium Hydroxide (Fisher, 5318)
8. Concentrated Hydrochloric Acid (Fisher, A144-500)
9. PBS=Phosphate Buffer Saline (Cellgro, 21-040-CV)
10. 0.5M Ethylenediaminetetraacetic Acid (EDTA) Solution (Invitrogen; 1758)
11. Thimerosal (Sigma, T8784)

Buffers and Solutions:
1. Degassed 5 mM EDTA/PBS Buffer, pH 7.2: Add 2 mL 0.5M EDTA solution to 200 mL PBS and then bubble argon gas into the resulting solution for 5 min to remove all the other gases in the solution.
2. 10% BSA/PBS Solution: Dissolve 100 mg BSA in 10 mL PBS and filter the solution through a 0.2 µm filter. The solution is kept in the −20° C. freezer.
3. 10% Thimerosal/PBS Solution: Dissolve 100 mg Thimerosal in 10 mL PBS and filter the solution through a 0.2 µm filter. The solution is kept in the −20° C. freezer.
4. 0.1M PB (Phosphate Buffer), pH 6.8.

Procedure:
Preparation of the LC-SMCC Solution for Immediate Usage in the Activation Reaction:
1. Take out a bottle of LC-SMCC from the −20° C. freezer and let it warm up to room temperature.
2. Weigh out between 1-2 mg of LC-SMCC in a 1.5 mL Eppendorf tube and add the proper volume of DMSO to make a 4.5 mg/mL (10 mM LC-SMCC) solution. Store the remaining LC-SMCC back in the freezer.

LC-SMCC Activation of the HER-2 Antibody:
1. Add 2.3 µL of the 10 mM LC-SMCC solution to 0.5 mL of the HER-2 antibody solution, which contains 500 µg of the antibody, and vortex immediately to start the reaction. After vortexing, keep the mixture at room temperature to continue the reaction for 30 min.
2. Meanwhile pre-equilibrate a desalting column by washing it with 50 mL degassed 5 mM EDTA/PBS buffer.
3. After activation of the HER-2 antibody with LC-SMCC is completed, the activation mixture is loaded onto the desalting column and the column eluted with degassed 5 mM EDTA/PBS buffer at room temperature. The eluted solution is collected at 0.5 mL fractions and monitored by UV absorbance at 280 nm with a spectrophotometer.
4. The fractions containing the activated antibody based on the UV absorbance are pooled and kept on ice for the next reaction.

LC-SMCC Activation of Glucose Oxidase:
1. Take 0.16 mL of dialyzed glucose oxidase, which contains 4 mg of the enzyme, and adjust its volume to 0.5 mL with the degassed 5 mM EDTA/PBS buffer.
2. Add 12.4 µL of the 10 mM LC-SMCC solution to the 0.5 mL glucose oxidase solution and vortex immediately to start the reaction. After vortexing, keep the mixture at room temperature to continue the reaction for 30 min.
3. Meanwhile pre-equilibrate a desalting column by washing it with 50 mL degassed 5 mM EDTA/PBS buffer.
4. After activation of the glucose oxidase with LC-SMCC is completed, the activation mixture is loaded onto the desalting column and the column eluted with degassed 5 mM EDTA/PBS buffer at room temperature. The eluted solution is collected at 0.5 mL fractions and monitored by UV absorbance at 280 nm with a spectrophotometer.
5. The fractions containing the activated glucose oxidase based on the UV absorbance are pooled and kept on ice for the next reaction.

Conjugation of the Activated HER-2 Antibody and the Activated Glucose Oxidase to Sulfhydryl-Activated Dextran:
1 To a lyophilized 1 mg aliquot of sulfhydryl-activated dextran is add 50 µL of Nanopure water to make a solution of 20 mg/mL of sulfhydryl-activated dextran.
2 To the pooled activated antibody solution is added a volume of the combined activated glucose oxidase solution that corresponds to 3 mg of glucose oxidase, followed by 34.3 µL of the sulfhydryl-modified dextran solution to give an approximate molar ratio of antibody: glucose oxidase:dextran as 2:12:1. After vortexing, the mixture is kept at 4° C. overnight.
3 The excess sulfhydryl groups remaining on the modified dextran are blocked by the addition of 56.4 µL of a 1 mg/mL N-Ethylmaleimide in degassed 0.5 mM EDTA/PBS buffer and the blocking reaction continued for 3 hours at 4° C.

Purification of the HER-2 Antibody-Glucose Oxidase-Dextran Conjugate:
1. After the blocking reaction, the HER-2 antibody-glucose oxidase-dextran conjugate solution is concentrated to ~300 µL in a Centricon Apparatus equipped with a 10,000 molecular weight cut-off YM-10 membrane.
2. The concentrated solution is transferred to a 1.5 mL Eppendorf tube and the tube spun at 16,000 g for 3 min to remove the small amount of precipitate.
3. The supernatant is transferred to a HPLC sample vial and the volume of the solution adjusted to 320 µL with the degassed 5 mM EDTA/PBS buffer for purification by HPLC.

4. One hundred microliter of the conjugated solution is injected onto a BioSep-SE-S 300 size exclusion column in an Agilent HPLC System and the conjugated protein separated by elution with 0.1M PB, pH 6.8 at a flow-rate of 0.5 mL/min for 40 min and the eluted solution monitored by UV absorbance at 280 nm.
5. The first UV absorption peak from the elution fractions is pooled and kept on ice.
6. The remaining 200 μL of the conjugated solution are also purified likewise and all of the first UV absorption peaks from the three HPLC runs are pooled together. The pooled conjugated solution is adjusted to 0.1% BSA with the 10% BSA/PBS solution and 0.02% Thimerosal with the 10% Thimerosal/PBS solution for long term storage at −70° C.
7. The glucose oxidase enzymatic activity present in the HER-2 antibody-glucose oxidase-dextran conjugate is determined by a glucose oxidase functional assay.
8. The antibody activity present in the HER-2 antibody-glucose oxidase-dextran conjugate is determined by a competition ELISA assay.

Example 18

Novel Multiplexed Assay to Detect Activation of ErbB Family Receptor Tyrosine Kinases in a Circulating Tumor Cell Abstract:

The expression/activation profiling of kinases and other signal transduction pathway molecules on a serial sampling of tumor tissues provides valuable information on changes occurring in tumor cells as a function of time and therapies. This temporal profiling of tumor progression enables clinicians to monitor rapidly evolving cancer signatures in each patient. This example illustrates a novel and robust assay to detect the level of expression and the degree of phosphorylation of the ErbB family of receptor tyrosine kinases (RTKs) and demonstrates the advantages of using such a therapy-guiding diagnostic system with single cell level sensitivity. The assay generally relies on samples such as fine needle aspirates (FNAs) and blood and achieves high sensitivity and specificity for interrogating the limited amount of cancer cells obtained from such samples.

Figure 19:
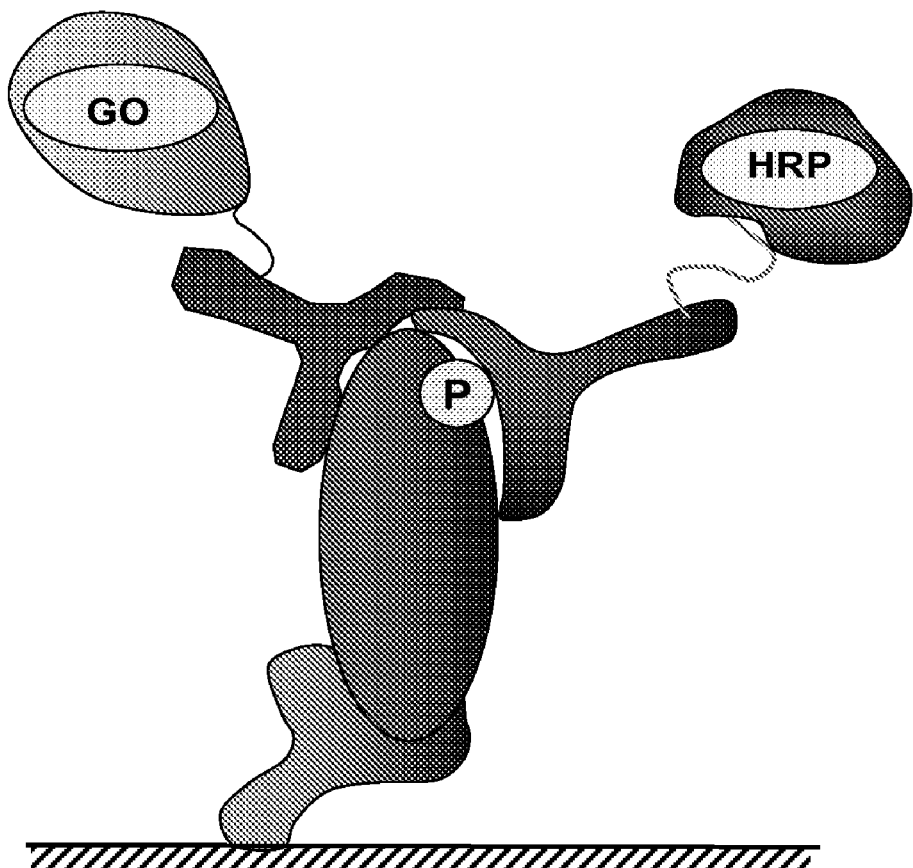
FIG. 19 shows one embodiment of the assay format of the present invention, which relies on the co-localization of two additional detector antibodies linked with enzymes for subsequent channeling events per each target protein bound.

Introduction:

Cancer onset and progression can be associated with abnormally regulated expression and activation of receptors and other components of the signal transduction pathway. The abnormal activation of HER-1 and HER-2 has been linked to various types of cancer progression. Methods for profiling HER-1 and HER-2 phosphorylation patterns may provide valuable insight into the overall disease pathogenesis, and therefore lead to a better therapy selection by identifying relevant disease causing molecules. The assay described herein is based on (1) a multiplexed protein microarray platform combined with (2) a triple-antibody-enzyme channeling signal amplification process. The microarray platform offers the expandability needed to accommodate multiple markers as well as the scalability required for commercial deployment. The unique and novel design of the assay described herein is provided by the triple-antibody enzyme approach that confers ultra-high sensitivity while preserving specificity. In embodiments where the assay is used to detect and quantify those targets that are phosphorylated, and therefore activated, the assay may be performed as follows:

1. The selected target is captured by target-specific antibodies printed in serial dilutions on a microarray surface. FIG. 19 illustrates one embodiment of the assay of the present invention, which relies on the co-localization of two additional detector antibodies linked with enzymes for subsequent channeling events per each target protein bound.
2. In the embodiment shown in FIG. 19, the immunocomplex formed by the initial target binding by capture antibodies and the secondary binding of glucose oxidase (GO)-conjugated antibodies that recognize an alternate epitope on the captured target molecules produces $H_2O_2$ in the presence of a GO substrate such as glucose. GO is one of the fastest enzymes known with a turnover number (TON) of $10^5$/min.
3. In the embodiment shown in FIG. 19, the target-specific local influx of $H_2O_2$ is then utilized by phospho-peptide-specific antibodies conjugated to horseradish peroxidase (HRP, with a TON of $10^4$/min.) that bind to the phosphorylated site on the captured targets, thereby amplifying the target-specific signal. Specificity for the detection of phosphorylated targets is greatly increased through the collaborative immuno-detection and amplification process given the requirement for simultaneous binding of three different types of antibodies.

The detection and quantification of as few as approximately $2-3\times10^4$ phosphorylation events is routinely achieved by the assay described herein, bringing its detection to a single cell level. This collaborative immunoassay configuration can be further applied to investigate protein interactions and activation states.

Methods:

Tissue Culture: SKBR3, MDA-MB-468, T47D, and BT474 cell lines were obtained from ATCC. Cells were grown in the following growth media in 100 mm tissue culture plates at 37° C. in 5% $CO_2$: SKBR3-MacCoy's 5A medium with 10% FBS; MDA-MB-468-DMEM, 10% FBS; BT474-DMEM, 10% FBS; T47D-RPMI 1640, 10% FBS, 0.2 U/ml bovine insulin. Cells were harvested at 70-80% confluency with gentle detachment process (trypsin treatment+subsequent inactivation) and were subsequently counted and washed with 1×PBS. Cell stimulation was performed with 100 μM EGF or 20 μM heregulin β or both in serum-free growth media for 5 min. Subsequently, stimulated cells were washed with 1×PBS and then were lysed and kept on ice for 30 min.

Slide Printing: Capture antibodies were diluted in 1×PBS with detergent. A contact microarray printer (Genetix) was utilized to print on 16 pad nitrocellulose FAST slides (Whatman). The spot diameter was approximately 175 μm and printed slides were kept in a desiccated chamber at 4° C.

Multiplexed Proximity Assay: Slides were incubated with blocking buffer for 1 hr and then washed 3× with TBST buffer. Cell lysates were then added onto each pad for overnight incubation at room temperature (RT). Upon the completion of the primary binding, lysates were aspirated and then each pad was washed several times with TBST. Then, secondary detector antibodies (conjugated with GO or HRP) were added to each pad for 2 hr at RT. Unbound secondary detector antibodies were removed by washing with TBST, and signal amplification buffer containing glucose and biotinylated tyramide was added to each pad for 15 min. After removing excess biotinylated tyramide, Alexa-647 conjugated strepavidin was added for the signal detection.

Data Analysis: Quantitation was performed using Perkin Elmer ScanArray Express software and the data obtained was corrected for local and global background intensities. A GenePixArray List (GAL) file was used to provide descriptive name and identifier information and was incorporated into the image analysis output file. Signals from triplicate spots were averaged and data were normalized to correct for pad to pad variability. A nonlinear regression model was used for the quantitation of cell-equivalent amount for corresponding relative fluorescence unit (RFU) values. The data were fit to a five parameter Hill equation to generate the standard curves. Each curve was validated against known controls. A known number of cells was predicted for the appropriate dilution, corresponding to the curve with the highest slope at the intensity of the unknown sample.

Western Blot: After roughly equal numbers of cell lysates for each cell line were obtained, they were aliquoted into single use vials. The protein concentration was determined using a bicinchoninic acid (BCA) protein assay. Samples were prepared with sample buffer containing β-mercaptoethanol, and after boiling for 5 min. and cooling to RT, the samples were loaded onto a NuPage 4-12% gel alongside a protein ladder. Upon completion of electrophoresis, the separated proteins in the gel were transferred to a nitrocellulose membrane. The membrane was washed, blocked with 5% milk blotto and incubated first with primary and then with secondary antibodies before the detection process using NBT/BCIP.

Figure 20:
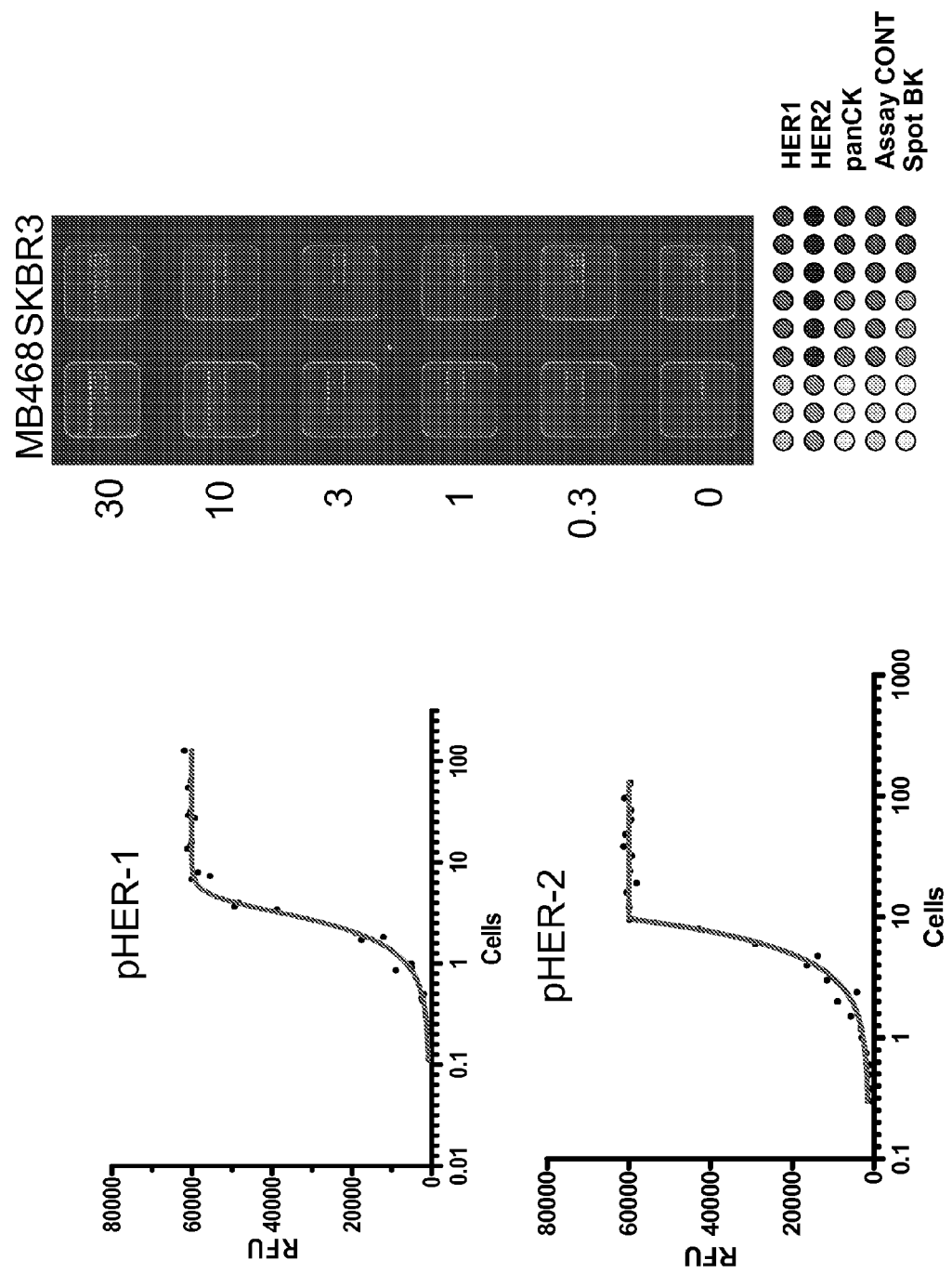
FIG. 20 shows single cell sensitivity for pHER-1 and pHER-2 assays.

Results:

Sensitivity: The activation and expression of HER-1 and HER-2 at a sensitivity level of a single cell were detected in multiple cell lines (MDA-MB-468, A431, BT-474, and SKBr-3 cell lines). These cell lines express approximately $1 \times 10^6$ total RTKs on their cell membrane per cell, although only subsets of the total RTKs get phosphorylated and such phosphorylation is required for pathway activation. The SKBR-3 cells have spontaneous HER-2 activation due to its amplification and therefore they provide a positive control reference. MDA-MB-468 cells need to be stimulated with EGF (TGF-a) to induce HER-1 phosphorylation and their signature before and after stimulation can be used as negative and positive controls. MDA-MB-468 has marginal HER-1 activation before stimulation, while both cell lines peak at approximately 2-5% of their RTKs activated (~0.5 to $1 \times 10^5$ phosphorylation events per cell). FIG. 20 shows that the assay format described herein enables detection of less than $10^5$ activation events with single cell sensitivity.

Figure 22:
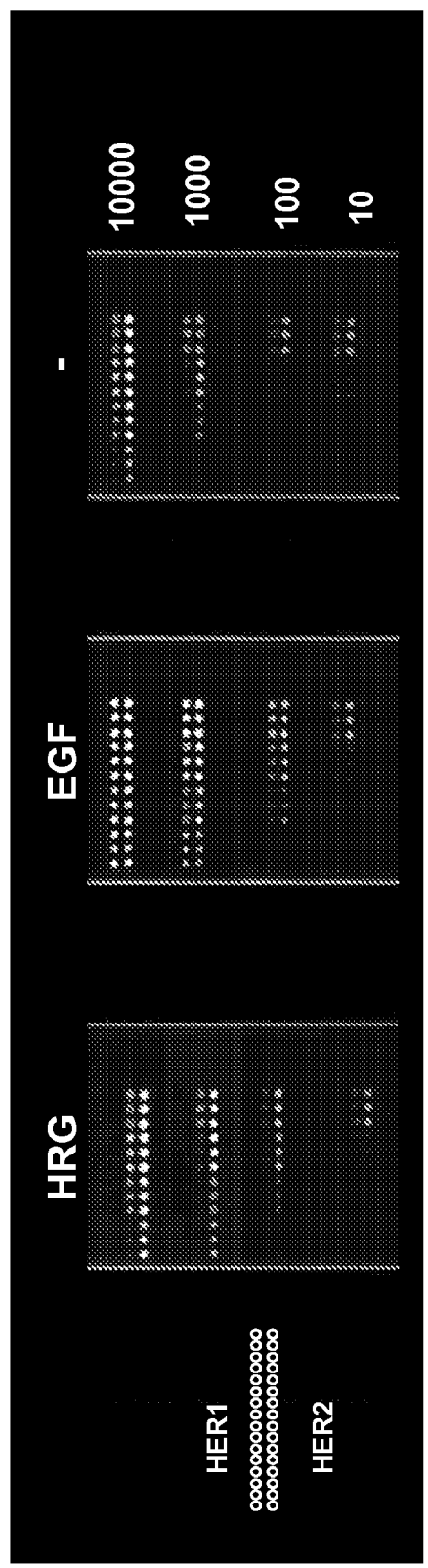
FIG. 22 shows the T47D ErbB RTK profile with EGF or HRG β stimulation.

Specificity: Analytical specificity of the collaborative immunoassay format described herein was >99.99% based on a comparative study performed on multiple cell lines with various RTK levels. Cell lines used and their dominant ErbB expression and the RTK activation upon EGF or HRG β stimulation is shown in the Western blot in FIG. 21. The RTK activation profile for T47D cells, which express some level of ErbB2 and ErbB3 but an extremely low amount of ErbB1, is shown in FIG. 22. The number of cells required to detect EC20 (12000 RFU) pHER-1 or pHER-2 were used to calculate per-cell RTK activation (RFU/cell) as shown in Table 43. When MB468 cells expressing an extremely low amount of HER-2 were used, having ~1000 cells per reaction pad was not sufficient to achieve EC20, and this type of low or non-detectable signal in other cell lines was indicated as "ND" in Table 43. MDA MB 468 cells have ~4000 RFU/cell level of pHER-1 when stimulated with EGF, yet do not show any detectable pHER-2. This collaborative immunoassay format ensures ultra-specificity while maintaining its sub-single cell level ($10^4$ to $10^5$) molecular level assay sensitivity.

TABLE 43

| | Relative Level of ErbB Expression | | | Per Cell-RTK Activation (RFU/cell) | | | |
|---|---|---|---|---|---|---|---|
| | | | | EGF | | HRG | |
| | ErbB1 | ErbB2 | ErbB3 | pHER1 | pHER2 | pHER1 | pHER2 |
| MDA MB 468 | 10 | — | 2 | 4000 | ND | 4000 | ND |
| BT 474 | — | 10 | 3 | 96 | 1200 | ND | 1200 |
| T47D | — | 2 | 4 | 60 | 80 | ND | 165 |
| SKBR3 | 3 | 10 | 2 | 360 | 1334 | 105 | 353 |

Figure 23:
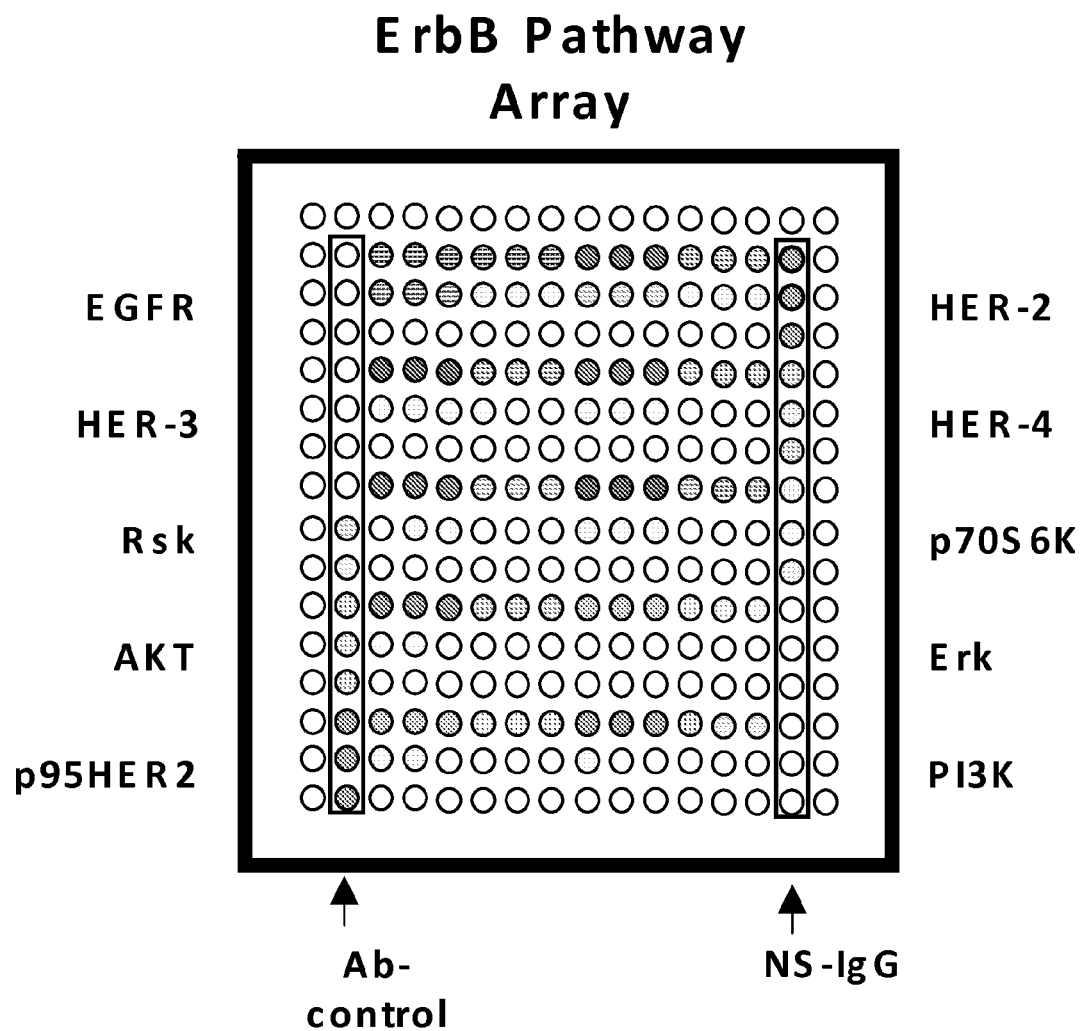
FIG. 23 shows an exemplary embodiment of an ErbB pathway array.

Conclusion:

This example illustrates a novel assay capable of specifically detecting the state of phosphorylation of ErbB family receptor members with sensitivity that enables its use with rare circulating tumor cells (CTCs). By identifying HER-1 and HER-2 activation in CTCs, this assay platform can provide guidance, not only for initial selection of targeted therapeutics, but also in subsequent monitoring for therapy progression. The expression/activation profiling of kinases and other signal transduction pathway molecules (shown in FIG. 23) on a serial sampling of CTCs will provide valuable information on changes occurring in tumor cells as a function of time and therapies. This therapy-guiding diagnostic approach can enter at various stages of the disease management, as shown in FIG. 18. The temporal and spatial profiling of tumor progression provided by the assay format described herein will enable clinicians to monitor rapidly evolving cancer signatures in each patient. Because of its unparallel sensitivity and specificity, the assay format described in this example can be applied to detect phosphorylation events in ErbB family receptor members present in rare CTCs. As such, this method can provide guidance, not only for the initial selection of targeted therapeutics, but also in subsequent monitoring for therapy progression.

In sum, the multiplexed proximity-based collaborative-immunoassay platform described herein provides valuable clinical information on limited samples with ultra-sensitivity and specificity to assist oncologists in maintaining or adjusting their disease treatment options for each patient according to a "personal" cancer profile shift.

Example 19

Method to Detect Activation of ErbB Family Receptor Tyrosine Kinases

The application presents technology capable of specifically detecting phosphorylation events in ErbB family receptor tyrosine kinases (RTKs) at a single-cell level sensitivity. In certain aspects, this multiplexed protein microarray platform utilizes the formation of a unique "triple-antibody-enzyme-channeling" immuno-complex. In one embodiment, this complex requires co-localization of two detector-antibodies conjugated with corresponding channeling-enzymes once target proteins are bound by the capture antibodies. The channeling events between two detector enzymes in proximity, glucose oxidase (GO, conjugated to anti-RTK antibodies) and horseradish peroxidase (HRP, conjugated to anti-phosphorylated sites in RTKs) enabled the profiling of the RTK with extreme sensitivity. This principle was applied to two breast cancer model systems with a limited number of target cells: cancer cells found in a patient's whole blood (circulating tumor cells, CTCs) and in a fine needle aspirate (FNA) sample.

Here we report the successful detection of activation (phosphorylation) of HER1 and HER2 (pHER1 and pHER2) in a CTC model system, at a sensitivity level of a single cell for the MDA-MB 468 and SKBr-3 cell lines. The analytical specificity of the "proximity-immunoassay" format was >99.99% based on comparative studies performed on multiple cell lines with various RTK levels. In addition, also presented herein are xenograft models for different types of breast cancer using cell lines with varying degrees of ErbB-RTK expression (MDA-MB-231, MDA-MB-468, and MDA-MB-435) to demonstrate its potential application with FNA (and metastatic FNA) samples. While it was possible to detect moderate levels of pHER2 and pHER1 in MD-MB-231 xenograft-FNA and significant pHER1 in FNA obtained from MDA-MB-468 xenografts, no HER1 or HER2 activation was detected in FNA obtained from MDA-MB-435 xenografts. These findings from the xenograft-FNA model system are concordant with the driver cell-line profile, demonstrating that this method can be used to detect activation of ErbB receptors in any type of sample obtained from minimally invasive procedures (e.g., from CTCs to FNAs).

This assay's ability to monitor activation status of the targeted-RTKs with a limited amount of sample is extremely useful as the success of the targeted therapies relies on the drug's ability to switch off (or dephosphorylate) targeted-RTKs. Furthermore, this principle can be applied to investigate other signal transduction pathway molecules for better therapy selection and effective disease monitoring among available breast cancer treatment options. As the disease profile often shifts in recurrent breast cancer, this unique assay format can be utilized to provide valuable clinical information on limited samples obtained from an "evolving disease" to help oncologists adjust their disease treatment options for each patient according to a "personal" cancer profile shift.

Example 20

Method to Detect Activation of Receptor Tyrosine Kinases in Circulating Tumor Cells Using a Proximity-Mediated Microarray Immunoassay Background: The abnormal activation of HER1 and HER2 has been linked to various types of cancer progression, and the changes in their expression status between primary tumor and circulating tumor cells (CTCs) have been reported to occur at a significant frequency. Methods for detecting HER1 and HER2 phosphorylation in serially collected CTCs may provide valuable insight into the overall disease profile shift, and therefore lead to better therapy selections/adjustments.

Methods: A triple-antibody-enzyme-channeling multiplexed protein microarray platform has been developed to detect the phosphorylation of target molecules. This multiplexed protein microarray platform utilizes a unique immuno-complex formation via co-localization of two detector enzyme-conjugated-antibodies once target proteins are captured on the microarray surface. The channeling events between the two detector enzymes in proximity enables the profiling of the receptor tyrosine kinases (RTKs) with a single-cell level sensitivity. Specificity for the detection of phosphorylated targets is greatly increased given the requirement for simultaneous binding of three antibodies. In order to validate the method on clinical samples, assays were performed on activated CTCs from 75 cancer patients on various therapy regimens.

Results: We identified 6 patients (8%) with activated HER1, 6 patients (8%) with activated HER2, and 14 (18.5%) patients with dual RTK activation in their CTCs. 25 normal samples showed no detectable HER1/HER2 activation. We also observed discrepancies between HER2 activation status between CTCs and their corresponding primary HER2-IHC status among breast cancer patients. CTCs with activated HER2 were found in 6 patients out of 16 (38%) HER2-negative primary breast cancers. In addition, 2 out of 5 (40%) HER2-positive patients had CTCs with no apparent HER2 activation.

Conclusion: The multiplexed proximity-mediated platform advantageously provides single-cell level sensitivity for detecting the activation of RTKs in a limited amount of sample. As such, CTCs found in metastatic stage cancers can be obtained and profiled to provide valuable information to impact clinical practice.

Example 21

Method to Detect Activation of Receptor Tyrosine Kinases on Metastatic Lesions Using a Proximity-Mediated Microarray Immunoassay Background: The changes in tumor receptor expression status between primary site and metastatic lesions are known to occur at a significant frequency (~15 to 20%). As a result, methods for profiling receptor tyrosine kinase (RTK) activation patterns on metastatic tumors may provide valuable insight into the shifting disease pathogenesis.

Methods: A novel technology capable of specifically detecting phosphorylation events in ErbB family RTKs has been developed. This multiplexed protein microarray platform utilizes the formation of a unique immuno-complex requiring the co-localization of two detector enzyme-conjugated-antibodies once target proteins are captured on the microarray-surface. The channeling events between the two detector enzymes (e.g., glucose oxidase and horseradish peroxidase) in proximity enables the profiling of RTKs with extreme sensitivity. In fact, the analytical specificity is greatly enhanced given the requirement for simultaneous binding of three different antibodies. We used 29 frozen breast cancer tissues (stage II to IV) as a model system for metastatic fine needle aspirate (mFNA) RTK profiling.

Results: The tumor tissue samples collected using G23 gauge needles were lysed in 100 µl lysis buffer, and the soluble samples (containing ~100 to 200 µg protein) were analyzed for RTK activation status. Out of 29 FNA samples, 27% (8/29) showed highly activated HER2, and 2 samples (6%) showed an intermediate level of activated HER2. One of the samples with intermediate HER2 activation also showed an intermediate level of HER1 activation. Two of the 8 HER2 activated samples also showed a significant level of HER1 activation. Among the 19 activated HER2-negative samples, 3 showed a moderate level of HER1 activation.

Conclusion: The multiplexed proximity-mediated platform advantageously provides single-cell level sensitivity of target phosphorylation events for detecting the activation of RTKs in a limited amount of mFNA tissue sample. The ability to profile tumors at different metastatic sites therefore provides valuable information on their differential metastatic potentials. As such, minimally-invasive single-passage mFNA samples may be utilized to tailor therapy options as the disease profile changes.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for selecting a suitable anticancer drug for the treatment of a breast tumor, the method comprising:
   (a) isolating cells of a breast tumor after administration of an anticancer drug, or prior to incubation with an anticancer drug;
   (b) lysing the isolated cells to produce a cellular extract;
   (c) detecting an activation state of one or more analytes in the cellular extract using an assay comprising a plurality of dilution series of capture antibodies specific for the one or more analytes, wherein the capture antibodies are restrained on a solid support, and wherein the assay comprises:
      (i) incubating the cellular extract with the plurality of dilution series of capture antibodies to form a plurality of captured analytes;
      (ii) incubating the plurality of captured analytes with detection antibodies comprising a plurality of activation state-independent antibodies and a plurality of activation state-dependent antibodies specific for the corresponding analytes to form a plurality of detectable captured analytes,
   wherein the activation state-independent antibodies are labeled with glucose oxidase, wherein the glucose oxidase and the activation state-independent antibodies are conjugated to a sulfhydryl-activated dextran molecule, wherein the activation state-dependent antibodies are labeled with a first member of a signal amplification pair, and wherein the glucose oxidase generates an oxidizing agent which channels to and reacts with the first member of the signal amplification pair;
      (iii) incubating the plurality of detectable captured analytes with a second member of the signal amplification pair to generate an amplified signal; and
      (iv) detecting the amplified signal generated from the first and second members of the signal amplification pair; and
   (d) determining whether the anticancer drug is suitable or unsuitable for the treatment of the breast tumor by comparing the activation state detected for the one or more analytes with a reference activation profile generated in the absence of the anticancer drug.

2. The method of claim 1, wherein the breast tumor is derived from a subject with ductal carcinoma or lobular carcinoma.

3. The method of claim 2, wherein the ductal carcinoma is invasive ductal carcinoma or ductal carcinoma in situ.

4. The method of claim 2, wherein the lobular carcinoma is invasive lobular carcinoma or lobular carcinoma in situ.

5. The method of claim 1, wherein the cells comprise circulating cells of the breast tumor.

6. The method of claim 5, wherein the circulating cells are isolated from a sample by immunomagnetic separation.

7. The method of claim 6, wherein the sample is selected from the group consisting of whole blood, serum, plasma, ductal lavage fluid, nipple aspirate, lymph, bone marrow aspirate, urine, saliva, fine needle aspirate, and combinations thereof.

8. The method of claim 5, wherein the circulating cells are selected from the group consisting of circulating tumor cells, circulating endothelial cells, circulating endothelial progenitor cells, cancer stem cells, disseminated tumor cells, and combinations thereof.

9. The method of claim 1, wherein the cells are isolated from tumor tissue.

10. The method of claim 9, wherein the tumor tissue is primary tumor tissue or metastatic tumor tissue.

11. The method of claim 9, wherein the cells are isolated from tumor tissue as a fine needle aspirate sample.

12. The method of claim 1, wherein the isolated cells are stimulated in vitro with growth factors.

13. The method of claim 1, wherein the anticancer drug is selected from the group consisting of a monoclonal antibody, tyrosine kinase inhibitor, chemotherapeutic agent, hormonal therapeutic agent, radiotherapeutic agent, vaccine, and combinations thereof.

14. The method of claim 13, wherein the monoclonal antibody is selected from the group consisting of trastuzumab (Herceptin®), alemtuzumab (Campath®), bevacizumab (Avastin®), cetuximab (Erbitux®), gemtuzumab (Mylotarg®), panitumumab (Vectibix™), rituximab (Rituxan®), tositumomab (BEXXAR®), and combinations thereof.

15. The method of claim 13, wherein the tyrosine kinase inhibitor is selected from the group consisting of gefitinib (Iressa®), sunitinib (Sutent®), erlotinib (Tarceva®), lapatinib (Tykerb®), canertinib (CI 1033), semaxinib (SU5416), vatalanib (PTK787/ZK222584), sorafenib (BAY 43-9006), imatinib mesylate (Gleevec®), leflunomide (SU101), vandetanib (ZACTIMA™; ZD6474), and combinations thereof.

16. The method of claim 13, wherein the chemotherapeutic agent is selected from the group consisting of pemetrexed (ALIMTA®), gemcitabine (Gemzar®), sirolimus (rapamycin), rapamycin analogs, platinum compounds, carboplatin, cisplatin, satraplatin, paclitaxel (Taxol®), docetaxel (Taxotere®), temsirolimus (CCI-779), everolimus (RAD001), and combinations thereof.

17. The method of claim 13, wherein the hormonal therapeutic agent is selected from the group consisting of aromatase inhibitors, selective estrogen receptor modulators, steroids, finasteride, gonadotropin-releasing hormone agonists, pharmaceutically acceptable salts thereof, stereoisomers thereof, derivatives thereof, analogs thereof, and combinations thereof.

18. The method of claim 13, wherein the radiotherapeutic agent is selected from the group consisting of $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$Sn, $^{149}$Pm, $^{153}$Sm, $^{166}$Ho, $^{177}$Lu, $^{186}$Re, $^{188}$Re, $^{211}$At, $^{212}$Bi, and combinations thereof.

19. The method of claim 1, wherein the one or more analytes comprise a plurality of signal transduction molecules.

20. The method of claim 19, wherein the plurality of signal transduction molecules is selected from the group consisting of receptor tyrosine kinases, non-receptor tyrosine kinases, tyrosine kinase signaling cascade components, nuclear hormone receptors, nuclear receptor coactivators, nuclear receptor repressors, and combinations thereof.

21. The method of claim 19, wherein the plurality of signal transduction molecules is selected from the group consisting of EGFR (ErbB1), HER-2 (ErbB2), p95ErbB2, HER-3 (ErbB3), HER-4 (ErbB4), Raf, SRC, Mek, NFkB-IkB, mTor, PI3K, VEGF, VEGFR-1, VEGFR-2, VEGFR-3, Eph-a, Eph-b, Eph-c, Eph-d, cMet, FGFR, cKit, Flt-3, Tie-1, Tie-2, Flt-3, cFMS, PDGFRA, PDGFRB, Abl, FTL 3, RET, Kit, HGFR, FGFR1, FGFR2, FGFR3, FGFR4, IGF-1R, ER, PR, NCOR, AIB1, and combinations thereof.

22. The method of claim 19, wherein the plurality of signal transduction molecules is selected from the group consisting of ErbB1, ErbB2, p95ErbB2, ErbB3, ErbB4, VEGFR-1, VEGFR-2, VEGFR-3, ER, PR, and combinations thereof.

23. The method of claim 1, wherein the activation state is selected from the group consisting of a phosphorylation state, ubiquitination state, complexation state, and combinations thereof.

24. The method of claim 1, wherein the solid support is selected from the group consisting of glass, plastic, chips, pins, filters, beads, paper, membrane, fiber bundles, and combinations thereof.

25. The method of claim 1, wherein the capture antibodies are restrained on the solid support in an addressable array.

26. The method of claim 1, wherein the activation state-dependent antibodies are directly labeled with the first member of the signal amplification pair.

27. The method of claim 1, wherein the activation state-dependent antibodies are labeled with the first member of the signal amplification pair via binding between a first member of a binding pair conjugated to the activation state-dependent antibodies and a second member of the binding pair conjugated to the first member of the signal amplification pair.

28. The method of claim 27, wherein the first member of the binding pair is biotin.

29. The method of claim 27, wherein the second member of the binding pair is streptavidin.

30. The method of claim 1, wherein the sulfhydryl-activated dextran molecule has a molecular weight of 500 kDa.

31. The method of claim 1, wherein the oxidizing agent is hydrogen peroxide ($H_2O_2$).

32. The method of claim 31, wherein the first member of the signal amplification pair is a peroxidase.

33. The method of claim 32, wherein the peroxidase is horseradish peroxidase (HRP).

34. The method of claim 32, wherein the second member of the signal amplification pair is a tyramide reagent.

35. The method of claim 34, wherein the tyramide reagent is biotin-tyramide.

36. The method of claim 35, wherein the amplified signal is generated by peroxidase oxidization of the biotin-tyramide to produce an activated tyramide.

37. The method of claim 36, wherein the activated tyramide is directly detected.

38. The method of claim 36, wherein the activated tyramide is detected upon the addition of a signal-detecting reagent.

39. The method of claim 38, wherein the signal-detecting reagent is a streptavidin-labeled fluorophore.

40. The method of claim 38, wherein the signal-detecting reagent is a combination of a streptavidin-labeled peroxidase and a chromogenic reagent.

41. The method of claim 40, wherein the chromogenic reagent is 3,3',5,5'-tetramethylbenzidine (TMB).

42. A method for identifying the response of a breast tumor to treatment with an anticancer drug, the method comprising:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support, and wherein the assay comprises:
(i) incubating the cellular extract with the plurality of dilution series of capture antibodies to form a plurality of captured analytes;
(ii) incubating the plurality of captured analytes with detection antibodies comprising a plurality of activation state-independent antibodies and a plurality of activation state-dependent antibodies specific for the corresponding analytes to form a plurality of detectable captured analytes,
wherein the activation state-independent antibodies are labeled with glucose oxidase, wherein the glucose oxidase and the activation state-independent antibodies are conjugated to a sulfhydryl-activated dextran molecule, wherein the activation state-dependent antibodies are labeled with a first member of a signal amplification pair, and wherein the glucose oxidase generates an oxidizing agent which channels to and reacts with the first member of the signal amplification pair;
(iii) incubating the plurality of detectable captured analytes with a second member of the signal amplification pair to generate an amplified signal; and
(iv) detecting the amplified signal generated from the first and second members of the signal amplification pair; and
(d) identifying the breast tumor as responsive or non-responsive to treatment with the anticancer drug by comparing the activation state detected for the one or more analytes with a reference activation profile generated in the absence of the anticancer drug.

43. The method of claim 42, wherein the breast tumor is derived from a subject with ductal carcinoma or lobular carcinoma.

44. The method of claim 42, wherein the cells comprise circulating cells of the breast tumor.

45. The method of claim 42, wherein the cells are isolated from tumor tissue.

46. The method of claim 42, wherein the tumor tissue is primary tumor tissue or metastatic tumor tissue.

47. The method of claim 45, wherein the cells are isolated from tumor tissue as a fine needle aspirate sample.

48. The method of claim 42, wherein the anticancer drug is selected from the group consisting of a monoclonal antibody, tyrosine kinase inhibitor, chemotherapeutic agent, hormonal therapeutic agent, radiotherapeutic agent, vaccine, and combinations thereof.

49. The method of claim 42, wherein the one or more analytes comprise a plurality of signal transduction molecules.

50. The method of claim 49, wherein the plurality of signal transduction molecules is selected from the group consisting of receptor tyrosine kinases, non-receptor tyrosine kinases, tyrosine kinase signaling cascade components, nuclear hormone receptors, nuclear receptor coactivators, nuclear receptor repressors, and combinations thereof.

51. The method of claim 49, wherein the plurality of signal transduction molecules is selected from the group consisting of EGFR (ErbB1), HER-2 (ErbB2), p95ErbB2, HER-3 (ErbB3), HER-4 (ErbB4), Raf, SRC, Mek, NFkB-IkB, mTor, PI3K, VEGF, VEGFR-1, VEGFR-2, VEGFR-3, Eph-a, Eph-b, Eph-c, Eph-d, cMet, FGFR, cKit, Flt-3, Tie-1, Tie-2, Flt-3, cFMS, PDGFRA, PDGFRB, Abl, FTL 3, RET, Kit, HGFR, FGFR1, FGFR2, FGFR3, FGFR4, IGF-1R, ER, PR, NCOR, AIB1, and combinations thereof.

52. The method of claim 49, wherein the plurality of signal transduction molecules is selected from the group consisting of ErbB1, ErbB2, p95ErbB2, ErbB3, ErbB4, VEGFR-1, VEGFR-2, VEGFR-3, ER, PR, and combinations thereof.

53. The method of claim 42, wherein the activation state is selected from the group consisting of a phosphorylation state, ubiquitination state, complexation state, and combinations thereof.

54. A method for predicting the response of a subject having a breast tumor to treatment with an anticancer drug, the method comprising:
(a) isolating cells of a breast tumor after administration of an anticancer drug, or prior to incubation with an anticancer drug;
(b) lysing the isolated cells to produce a cellular extract;
(c) detecting an activation state of one or more analytes in the cellular extract using an assay comprising a plurality of dilution series of capture antibodies specific for the one or more analytes, wherein the capture antibodies are restrained on a solid support, and wherein the assay comprises:
(i) incubating the cellular extract with the plurality of dilution series of capture antibodies to form a plurality of captured analytes;
(ii) incubating the plurality of captured analytes with detection antibodies comprising a plurality of activation state-independent antibodies and a plurality of activation state-dependent antibodies specific for the corresponding analytes to form a plurality of detectable captured analytes,
wherein the activation state-independent antibodies are labeled with glucose oxidase, wherein the glucose oxidase and the activation state-independent antibodies are conjugated to a sulfhydryl-activated dextran molecule, wherein the activation state-dependent antibodies are labeled with a first member of a signal amplification pair, and wherein the glucose oxidase generates an oxidizing agent which channels to and reacts with the first member of the signal amplification pair;
(iii) incubating the plurality of detectable captured analytes with a second member of the signal amplification pair to generate an amplified signal; and
(iv) detecting the amplified signal generated from the first and second members of the signal amplification pair; and
(d) predicting the likelihood that the subject will respond to treatment with the anticancer drug by comparing the activation state detected for the one or more analytes with a reference activation profile generated in the absence of the anticancer drug.

55. The method of claim 54, wherein the breast tumor is derived from a subject with ductal carcinoma or lobular carcinoma.

56. The method of claim 54, wherein the cells comprise circulating cells of the breast tumor.

57. The method of claim 54, wherein the cells are isolated from tumor tissue.

58. The method of claim 57, wherein the tumor tissue is primary tumor tissue or metastatic tumor tissue.

59. The method of claim 57, wherein the cells are isolated from tumor tissue as a fine needle aspirate sample.

60. The method of claim 54, wherein the anticancer drug is selected from the group consisting of a monoclonal antibody, tyrosine kinase inhibitor, chemotherapeutic agent, hormonal therapeutic agent, radiotherapeutic agent, vaccine, and combinations thereof.

61. The method of claim 54, wherein the one or more analytes comprise a plurality of signal transduction molecules.

62. The method of claim 61, wherein the plurality of signal transduction molecules is selected from the group consisting of receptor tyrosine kinases, non-receptor tyrosine kinases, tyrosine kinase signaling cascade components, nuclear hormone receptors, nuclear receptor coactivators, nuclear receptor repressors, and combinations thereof.

63. The method of claim 61, wherein the plurality of signal transduction molecules is selected from the group consisting of EGFR (ErbB1), HER-2 (ErbB2), p95ErbB2, HER-3 (ErbB3), HER-4 (ErbB4), Raf, SRC, Mek, NFkB-IkB, mTor, PI3K, VEGF, VEGFR-1, VEGFR-2, VEGFR-3, Eph-a, Eph-b, Eph-c, Eph-d, cMet, FGFR, cKit, Flt-3, Tie-1, Tie-2, Flt-3, cFMS, PDGFRA, PDGFRB, Abl, FTL 3, RET, Kit, HGFR, FGFR1, FGFR2, FGFR3, FGFR4, IGF-1R, ER, PR, NCOR, AIB1, and combinations thereof.

64. The method of claim 61, wherein the plurality of signal transduction molecules is selected from the group consisting of ErbB1, ErbB2, p95ErbB2, ErbB3, ErbB4, VEGFR-1, VEGFR-2, VEGFR-3, ER, PR, and combinations thereof.

65. The method of claim 54, wherein the activation state is selected from the group consisting of a phosphorylation state, ubiquitination state, complexation state, and combinations thereof.

66. A method for detecting the presence of a truncated receptor, said method comprising:
(a) incubating a cellular extract with a plurality of beads specific for an extracellular domain (ECD) binding region of a full-length receptor;
(b) removing said plurality of beads from said cellular extract, thereby removing said full-length receptor to form a cellular extract devoid of said full-length receptor;
(c) incubating said cellular extract devoid of said full-length receptor with a plurality of capture antibodies, wherein said plurality of capture antibodies is specific for an intracellular domain (ICD) binding region of said truncated receptor and wherein said plurality of capture antibodies is restrained on a solid support to form a plurality of captured truncated receptors;
(d) incubating the plurality of captured truncated receptors with detection antibodies specific for the corresponding truncated receptors to form a plurality of detectable captured truncated receptors;
(e) incubating the plurality of detectable captured truncated receptors with first and second members of a signal amplification pair to generate an amplified signal; and
(f) detecting an amplified signal generated from the first and second members of the signal amplification pair.

67. The method of claim 66, wherein said truncated receptor is p95ErbB2.

68. The method of claim 66, wherein said full-length receptor is ErbB2 (HER-2).

69. The method of claim 66, wherein said plurality of beads specific for an extracellular domain (ECD) binding region comprise a streptavidin-biotin pair, wherein the streptavidin is attached to the bead and the biotin is attached to an antibody.

70. The method of claim 69, wherein said antibody is specific for said ECD binding region of said full-length receptor.

71. The method of claim 66, wherein the cellular extract is produced by lysing circulating cells of a breast tumor.

72. The method of claim 66, wherein the cellular extract is produced by lysing cells isolated from tumor tissue.

73. The method of claim 72, wherein the tumor tissue is primary tumor tissue or metastatic tumor tissue.

74. The method of claim 72, wherein the cells are isolated from tumor tissue as a fine needle aspirate sample.

75. The method of claim 66, wherein an activation state of said plurality of detectable captured truncated receptors is interrogated.

76. The method of claim 75, wherein said activation state is selected from the group consisting of a phosphorylation state, ubiquitination state, complexation state, and combinations thereof.

77. A method for detecting the presence of a truncated receptor, said method comprising:
   (a) incubating a cellular extract with a plurality of beads specific for an extracellular domain (ECD) binding region of a full-length receptor;
   (b) removing said plurality of beads from said cellular extract, thereby removing said full-length receptor to form a cellular extract devoid of said full-length receptor;
   (c) incubating said cellular extract devoid of said full-length receptor with a plurality of capture antibodies, wherein said plurality of capture antibodies is specific for an intracellular domain (ICD) binding region of said truncated receptor and wherein said plurality of capture antibodies is restrained on a solid support to form a plurality of captured truncated receptors;
   (d) incubating the plurality of captured truncated receptors with detection antibodies comprising a plurality of activation state-independent antibodies and a plurality of activation state-dependent antibodies specific for the corresponding truncated receptors to form a plurality of detectable captured truncated receptors, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
   (e) incubating the plurality of detectable captured truncated receptors with a second member of the signal amplification pair to generate an amplified signal; and
   (f) detecting the amplified signal generated from the first and second members of the signal amplification pair.

78. The method of claim 77, wherein said truncated receptor is p95ErbB2.

79. The method of claim 77, wherein said full-length receptor is ErbB2 (HER-2).

80. The method of claim 77, wherein said plurality of beads specific for an extracellular domain (ECD) binding region comprise a streptavidin-biotin pair, wherein the streptavidin is attached to the bead and the biotin is attached to an antibody.

81. The method of claim 80, wherein said antibody is specific for said ECD binding region of said full-length receptor.

82. The method of claim 77, wherein the cellular extract is produced by lysing circulating cells of a breast tumor.

83. The method of claim 77, wherein the cellular extract is produced by lysing cells isolated from tumor tissue.

84. The method of claim 83, wherein the tumor tissue is primary tumor tissue or metastatic tumor tissue.

85. The method of claim 83, wherein the cells are isolated from tumor tissue as a fine needle aspirate sample.

86. The method of claim 77, wherein the facilitating moiety is glucose oxidase.

87. The method of claim 86, wherein the glucose oxidase and the activation state-independent antibodies are conjugated to a sulfhydryl-activated dextran molecule.

88. The method of claim 87, wherein the sulfhydryl-activated dextran molecule has a molecular weight of 500 kDa.

* * * * *